US012054541B2

(12) United States Patent
Muir et al.

(10) Patent No.: US 12,054,541 B2
(45) Date of Patent: Aug. 6, 2024

(54) SPLIT INTEINS, CONJUGATES AND USES THEREOF

(71) Applicant: THE TRUSTEES OF PRINCETON UNIVERSITY, Princeton, NJ (US)

(72) Inventors: Tom W. Muir, Princeton, NJ (US); Miquel Vila-Perello, Princeton, NJ (US); Zhihua Liu, Plainsborough, NJ (US); Neel H. Shah, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 17/491,729

(22) Filed: Oct. 1, 2021

(65) Prior Publication Data
US 2022/0098293 A1    Mar. 31, 2022

Related U.S. Application Data

(60) Continuation of application No. 16/690,213, filed on Nov. 21, 2019, now Pat. No. 11,161,899, which is a continuation of application No. 15/809,440, filed on Nov. 10, 2017, now Pat. No. 10,526,401, which is a division of application No. 14/411,702, filed as application No. PCT/US2013/047235 on Jun. 24, 2013, now abandoned.

(60) Provisional application No. 61/665,215, filed on Jun. 27, 2012.

(51) Int. Cl.
| | |
|---|---|
| C07K 14/195 | (2006.01) |
| C07K 16/18 | (2006.01) |
| C12N 9/00 | (2006.01) |
| C12N 15/62 | (2006.01) |
| C12P 21/02 | (2006.01) |
| C12P 21/06 | (2006.01) |

(52) U.S. Cl.
CPC ............ *C07K 16/18* (2013.01); *C07K 14/195* (2013.01); *C12N 9/93* (2013.01); *C12N 15/62* (2013.01); *C12P 21/02* (2013.01); *C12P 21/06* (2013.01); *C07K 2319/50* (2013.01); *C07K 2319/92* (2013.01)

(58) Field of Classification Search
CPC .. C07K 16/18; C07K 14/195; C07K 2319/50; C07K 2319/92; C12N 9/93; C12N 15/62; C12P 21/02; C12P 21/06
See application file for complete search history.

(56) References Cited

U.S. PATENT DOCUMENTS

| | | | |
|---|---|---|---|
| 4,179,337 A | 12/1979 | Davis et al. | |
| 4,289,872 A | 9/1981 | Denkewalter et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,229,490 A | 7/1993 | Tam | |
| 2004/0077842 A1 | 4/2004 | Himawan | |
| 2007/0207502 A1 | 9/2007 | Benkovic et al. | |

FOREIGN PATENT DOCUMENTS

| | | |
|---|---|---|
| CN | 101281201 A | 10/2008 |
| CN | 101333555 A | 12/2008 |
| WO | WO-89/02439 | 3/1989 |
| WO | WO-1993/21259 | 10/1993 |
| WO | WO-1995/06731 | 3/1995 |
| WO | WO-1995/11910 | 5/1995 |
| WO | WO-2009132455 A1 | 11/2009 |
| WO | WO-2011057163 A2 | 5/2011 |
| WO | WO-2013/045632 A1 | 4/2013 |

OTHER PUBLICATIONS

Chu et al., Journal of Peptide Science 16:582-588, published on line Apr. 6, 2010.*
Amitai et al., Modulation of intein activity by its neighboring extein substrates. *Proc. Natl. Acad. Sci. USA*, 106: 11005-10 (2009).
Appleby-Tagoe et al., Highly efficient and more general cis- and trans-splicing inteins through sequential directed evolution. *J. Biol. Chem.* 286: 34440-7 (2011).
Bryksin et al., Overlap extension PCR cloning: A simple and reliable way to create recombinant plasmids. *BioTechniques*, 48: 463-5 (2010).
Busche et al., Segmental isotopic labeling of a central domain in a multidomain protein by protein trans-splicing using only one robust DnaE intein. *Angew. Chem. Int. Ed. Engl.* 48: 6128-31 (2009).
Carter, Introduction to current and future protein therapeutics: a protein engineering perspective. *Exp. Cell Res.* 317: 1261-9 (2011).
Caspi et al., Distribution of split DnaE inteins in cyanobacteria. *Mol. Microbiol.* 50: 1569-77 (2003).
Chen et al., Functional characterization of a naturally occurring trans-splicing intein from Synechococcus elongatus in a mammalian cell system. *Anal. Biochem.* 407: 180-7 (2010).
Cheriyan et al., Protein splicing: A versatile tool for drug discovery. *Adv. Drug Deliv. Rev.* 61(11): 899-907 (2009).
Cload et al., Polyether tethered oligonucleotide probes. *J. Am. Chem. Soc.* 113: 6324-6 (1991).
Crooks et al., WebLogo: a sequence logo generator. *Genome Res.* 14: 1188-90 (2004).
Dassa et al., Trans protein splicing of cyanobacterial split inteins in endogenous and exogenous combinations. *Biochemistry*, 46: 322-30 (2007).

(Continued)

*Primary Examiner* — Delia M Ramirez
(74) *Attorney, Agent, or Firm* — MARSHALL, GERSTEIN & BORUN LLP

(57) ABSTRACT

Disclosed herein are split inteins, fused proteins of split inteins, and methods of using split inteins to efficiently purify and modify proteins of interest.

19 Claims, 18 Drawing Sheets
Specification includes a Sequence Listing.

(56) References Cited

OTHER PUBLICATIONS

Database Geneseq (online), Accession No. ATS48105, Beta-glucuronidse (gusA)-DnaE fusion protein sequence No. 1, (2009).
Database Geneseq (online), Accession No. AVB21461, Nostoc punctiforme DnaE fragment protein sequence SEQ 20, (2009).
Database Geneseq (online), Accession No. AZI18530, Intein protein sequence, Seq ID No. 2347, Jul. 7, 2011.
Database Geneseq (online), Accession No. AZY15692, *Nostoc* sp. PCC 7120 derived DnaE intein (INT), Seq ID No. 68, Sep. 13, 2012.
Database Geneseq (online), Accession No. BAM89830, DnaE protein N-Terminal split intein, Seq ID No. 28, May 23, 2013.
Dawson et al., Synthesis of proteins by native chemical ligation. *Science*, 266: 776-9 (1994).
Dhar et al., Modification of transmembrane and GPI-anchored proteins on living cells by efficient protein trans-splicing using the Npu DnaE intein. *Chem. Commun. (Camb)*, 47: 3063-5 (2011).
Du et al., Backbone dynamics and global effects of an activating mutation in minimized Mtu RecA inteins. *J. Mol. Biol.* 400: 755-67 (2010).
Durand et al., Circular dichroism studies of an oligodeoxyribonucleotide containing a hairpin loop made of a hexaethylene glycol chain: conformation and stability. *Nucl. Acids Res.* 18: 6353-9 (1990).
Evans et al., Mechanistic and kinetic considerations of protein splicing. *Chem. Rev.* 102: 4869-84 (2002).
Ferentz et al., Disulfide-crosslinked oligonucleotides. *J. Am. Chem. Soc.* 113: 4000-2 (1991).
Frutos et al., Branched intermediate formation stimulates peptide bond cleavage in protein splicing. *Nat. Chem. Biol.* 6: 527-33 (2010).
Hao et al., Computational Discovery of Picomolar Qo Site Inhibitors of Cytochrome bc1 Complex. *J. Am. Chem. Soc.* 134(27): 11168-76 (2012).
Iwai et al., Highly efficient protein trans-splicing by a naturally split DnaE intein from Nostoc punctiforme. *FEBS Lett.* 580: 1853-8 (2006).
Jschke et al., Automated incorporation of polyethylene glycol into synthetic oligonucleotides. *Tetrahedron Lett.* 34: 301-4 (1993).
Lockless et al., Traceless protein splicing utilizing evolved split inteins. *Proc. Natl. Acad. Sci. USA*, 106: 10999-1004 (2009).
Lu et al., Split intein facilitated tag affinity purification for recombinant proteins with controllable tag removal by inducible auto-cleavage. *J. Chromatography*, 1218: 2553-60 (2011).
Ma et al., Design and synthesis of RNA miniduplexes via a synthetic linker approach. 2. Generation of covalently closed, double-stranded cyclic HIV-1 TAR RNA analogs with high Tat-binding affinity. *Nucl. Acids Res.* 21: 2585-9 (1993).
Ma et al., Design and synthesis of RNA miniduplexes via a synthetic linker approach. *Biochemistry*, 32: 1751-8 (1993).
Martin et al., Characterization of a naturally occurring trans-splicing intein from *Synechocystis* sp. PCC6803. *Biochemistry*, 40: 1393-402 (2001).
McCurdy et al., Deoxyoligonucleotides with inverted polarity: Synthesis and use in triple-helix formation. *Nucleosides & Nucleotides*, 10(1-3): 287-90 (1991).
Mills et al., The mechanism of intein-mediated protein splicing: variations on a theme. *Protein Pept. Lett.* 12: 751-5 (2005).
Mohlmann et al., Site-specific modification of ED-B-targeting antibody using intein-fusion technology. *BMC Biotechnol.* 11: 76-85 (2011).
Mootz, Split inteins as versatile tools for protein semisynthesis, *Chembiochem*, 10(16):2579-89 (2009).
Muir et al., Expressed protein ligation: a general method for protein engineering. *Proc. Natl. Acad. Sci. USA*, 95: 6705-10 (1998).
Oeemig et al., Solution structure of DnaE intein from Nostoc punctiforme: structural basis for the design of a new split intein suitable for site-specific chemical modification. *FEBS Lett.* 583: 1451-6 (2009).
Olsen et al., Active site remodelling accompanies thioester bond formation in the SUMO E1. *Nature*, 463: 906-12 (2010).
Ono et al., DNA triplex formation of oligonucleotide analogues consisting of linker groups and octamer segments that have opposite sugar-phosphate backbone polarities. *Biochemistry*, 30: 9914-21 (1991).
Pellois et al., Semisynthetic proteins in mechanistic studies: Using chemistry to go where nature can't. *Curr. Opin. Chem. Biol.* 10: 487-91 (2006).
Perler et al., InBase: the Intein Database. *Nucl. Acids Res.* 30: 383-4 (2002).
Richardson et al., Tethered oligonucleotide probes. A strategy for the recognition of structured RNA. *J. Am. Chem. Soc.* 113: 5109-11 (1991).
Schwarzer et al., Probing intein-catalyzed thioester formation by unnatural amino acid substitutions in the active site. *Biochemistry*, 51: 233-42 (2012).
Seela et al., Oligodeoxyribonucleotides containing 1,3-propanediol as nucleoside substitute. *Nucl. Acids Res.* 15: 3113-29 (1987).
Shah et al., Extein Residues Play an Intimate Role in the Rate-Limiting Step of Protein Trans-Splicing, *J. Amer. Chem. Soc.*, 135(15):5839-47 (2013).
Shah et al., Inteins: nature's gift to protein chemists, *Chem. Sci.*, 5(2):446-461 (2014).
Shah et al., Kinetic control of one-pot trans-splicing reactions by using a wild-type and designed split intein. *Angew. Chem. Int. Ed.* 50: 6511-5 (2011).
Shah et al., Ultrafast protein splicing is common among cyanobacterial split inteins: Implications for protein engineering. *J. Am. Chem. Soc.* 134(28): 11338-41 (2012).
Shah et al., Ultrafast protein splicing is common among cyanobacterial split inteins: Implications for protein engineering. *J. Am. Chem. Soc.* A-D (2012).
Southworth et al., Purification of proteins fused to either the amino or carboxy terminus of the *Mycobacterium xenopi* gyrase A intein. *Biotechniques*, 27: 110-4, 116, 118-20 (1999).
Stothard et al., The sequence manipulation suite: JavaScript programs for analyzing and formatting protein and DNA sequences. *BioTechniques*, 28: 1102, 1104 (2000).
Sun et al., Crystal structures of an intein from the split dnaE gene of *Synechocystis* sp. PCC6803 reveal the catalytic model without the penultimate histidine and the mechanism of zinc ion inhibition of protein splicing. *J. Mol. Biol.* 353: 1093-105 (2005).
Vila-Perelló et al., Biological applications of protein splicing. *Cell*, 143: 191-200 (2010).
Vila-Perelló et al., Streamlined Expressed Protein Ligation Using Split Interins, *J. Amer. Chem. Soc.*, 135(1):286-92 (2013).
Volkmann et al., Recent Progress in intein research: from mechanism to directed evolution and applications, *Cell. Molec. Life Sci.*, 70(7):1182-206 (2012).
Waterhouse et al., Jalview Version 2—a multiple sequence alignment editor and analysis workbench. *Bioinformatics*, 25: 1189-91 (2009).
Wu et al., Conserved residues that modulate protein trans-splicing of Npu DnaE split intein, Biochem. J. 461:247-55 (2014).
Wu et al., Membrane targeting mechanism of Rab GTPases elucidated by semisynthetic protein probes. *Nat. Chem. Biol.* 6: 534-40 (2010).
Yang et al., Intein-mediated assembly of a functional β-glucuronidase in transgenic plants, *PNAS*, 100(6):3513-8 (2002).
Zettler et al., The naturally split Npu DnaE intein exhibits an extraordinarily high rate in the protein trans-splicing reaction. *FEBS Lett.* 583: 909-14 (2009).
Thom et al., "Recobinant Protein Hydrazides: Application to Site-Specific Protein PEFylation", Bioconjugate Chemistry. 22, 1017-1020 (2011).
Kalia et al., "Reactivity of Intein Thioesters: Appending a Functional Group to a Protein", ChemBioChem, 7, 1375-1383 (2006).

* cited by examiner

NAME    N-INTEIN SEQUENCE

SEQ ID NOs: 776 and 777

SEQUENCE LISTING

<160> NUMBER OF SEQ ID NOS: 777

<210> SEQ ID NO 1
<211> LENGTH: 102
<212> TYPE: PRT
<213> ORGANISM: Nostoc punctiforme

<400> SEQUENCE: 1

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 2
<211> LENGTH: 123
<212> TYPE: PRT
<213> ORGANISM: Synechocystis PCC6803

<400> SEQUENCE: 2

Cys Leu Ser Phe Gly Thr Glu Ile Leu Thr Val Glu Tyr Gly Pro Leu
1               5                   10                  15

Pro Ile Gly Lys Ile Val Ser Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 3
<211> LENGTH: 110
<212> TYPE: PRT
<213> ORGANISM: Aphanothece halophytica

<400> SEQUENCE: 3

Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Cys Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
            50                  55                  60

Lys Ile Arg Ala Thr Lys Asp His Lys Met Met Thr Glu Ser Gly Glu
 65                  70                  75                  80

Met Leu Pro Ile Glu Glu Ile Phe Gln Arg Glu Leu Asp Leu Lys Val
                 85                  90                  95

Glu Thr Phe His Glu Met Ser Leu Leu Arg Arg Gly Ala Lys
            100                 105                 110

<210> SEQ ID NO 4
<211> LENGTH: 101
<212> TYPE: PRT
<213> ORGANISM: Aphanizomenon ovalisporum

<400> SEQUENCE: 4

Cys Leu Ser Ala Asp Thr Glu Ile Leu Thr Val Glu Tyr Gly Phe Leu
 1               5                  10                  15

Pro Ile Gly Glu Ile Val Gly Lys Ala Ile Glu Cys Arg Val Tyr Ser
                 20                  25                  30

Val Asp Gly Asn Gly Asn Ile Tyr Thr Gln Ser Ile Ala Gln Trp His
            35                  40                  45

Asn Arg Gly Glu Gln Glu Val Phe Glu Tyr Thr Leu Glu Asp Gly Ser
         50                  55                  60

Ile Ile Arg Ala Thr Lys Asp His Lys Phe Met Thr Asp Gly Glu
 65                  70                  75                  80

Met Leu Pro Ile Asp Glu Ile Phe Ala Arg Gln Leu Asp Leu Met Gln
                 85                  90                  95

Val Gln Gly Leu His
            100

<210> SEQ ID NO 5
<211> LENGTH: 102
<212> TYPE: PRT
<213> ORGANISM: Anabaena PCC7120

<400> SEQUENCE: 5

Cys Leu Ser Tyr Asp Thr Glu Val Leu Thr Val Glu Tyr Gly Phe Val
 1               5                  10                  15

Pro Ile Gly Glu Ile Val Glu Lys Gly Ile Glu Cys Ser Val Phe Ser
                 20                  25                  30

Ile Asn Asn Asn Gly Ile Val Tyr Thr Gln Pro Ile Ala Gln Trp His
            35                  40                  45

His Arg Gly Lys Gln Glu Val Phe Glu Tyr Cys Leu Glu Asp Gly Ser
         50                  55                  60

Ile Ile Lys Ala Thr Lys Asp His Lys Phe Met Thr Gln Asp Gly Lys
 65                  70                  75                  80

Met Leu Pro Ile Asp Glu Ile Phe Glu Gln Glu Leu Asp Leu Leu Gln
                 85                  90                  95

Val Lys Gly Leu Pro Glu
            100

<210> SEQ ID NO 6
<211> LENGTH: 102
<212> TYPE: PRT
<213> ORGANISM: Anabaenavariabilis

<400> SEQUENCE: 6

```
Cys Leu Ser Tyr Asp Thr Glu Val Leu Thr Val Glu Tyr Gly Phe Val
1               5                   10                  15

Pro Ile Gly Glu Ile Val Asp Lys Gly Ile Glu Cys Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
            85                  90                  95

Val Lys Gly Leu Pro Glu
            100
```

<210> SEQ ID NO 7
<211> LENGTH: 118
<212> TYPE: PRT
<213> ORGANISM: Cylindrospermopsis raciborskii

<400> SEQUENCE: 7

```
Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Cys Thr Val Phe Ser
            20                  25                  30

Leu Asn Asp Ser Gly Asn Val Tyr Thr Gln Pro Ile Gly Gln Trp His
        35                  40                  45

Asp Arg Gly Val Gln Asp Leu Tyr Glu Tyr Cys Leu Asp Asp Gly Ser
    50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
            85                  90                  95

Val Ser Gly Ile Ser Lys Leu Val Gln Gln Arg Thr Leu Pro Phe Ile
            100                 105                 110

Ile Val Asp Arg Lys Leu
            115
```

<210> SEQ ID NO 8
<211> LENGTH: 99
<212> TYPE: PRT
<213> ORGANISM: Cyanothece CCY0110

<400> SEQUENCE: 8

```
Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Cys Ser Val Tyr Thr
            20                  25                  30

Val Asn Lys Asn Gly Phe Val Tyr Thr Gln Ser Ile Ala Gln Trp His
        35                  40                  45

His Arg Gly Glu Gln Glu Val Phe Glu Tyr Tyr Leu Glu Asp Gly Glu
    50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
            85                  90                  95
```

-continued

Leu Thr Val

<210> SEQ ID NO 9
<211> LENGTH: 99
<212> TYPE: PRT
<213> ORGANISM: Cyanothece PCC8801

<400> SEQUENCE: 9

```
Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Cys Thr Val Tyr Thr
            20                  25                  30

Val Asp Lys Asn Gly Phe Val Tyr Thr Gln Asn Ile Ala Gln Trp His
        35                  40                  45

Leu Arg Gly Gln Gln Glu Val Phe Glu Tyr Tyr Leu Asp Asp Gly Ser
    50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile
```

<210> SEQ ID NO 10
<211> LENGTH: 106
<212> TYPE: PRT
<213> ORGANISM: Crocosphaera watsonii

<400> SEQUENCE: 10

```
Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Cys Thr Val Tyr Thr
            20                  25                  30

Val Asp Lys Asn Gly Phe Val Tyr Thr Gln Thr Ile Ala Gln Trp His
        35                  40                  45

Asn Arg Gly Glu Gln Glu Ile Phe Glu Tyr Asp Leu Glu Asp Gly Ser
    50                  55                  60

Lys Ile Lys Ala Thr Lys Asp His Lys Phe Met Thr Ile Asp Gly Glu
65                  70                  75                  80

Met Leu Pro Ile Asp Glu Ile Phe Glu Lys Asn Leu Asp Leu Lys Gln
                85                  90                  95

Val Val Ser His Pro Asp Asp Tyr Leu Val
                100                 105
```

<210> SEQ ID NO 11
<211> LENGTH: 100
<212> TYPE: PRT
<213> ORGANISM: Microcystis aeruginosa

<400> SEQUENCE: 11

```
Cys Leu Gly Gly Glu Thr Leu Ile Leu Thr Glu Glu Tyr Gly Leu Leu
1               5                   10                  15

Pro Ile Ala Lys Ile Val Ser Glu Ile Asn Cys Thr Val Tyr Thr
            20                  25                  30

Val Asp Gln Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60
```

```
Thr Ile Gln Ala Thr Lys Asp His Lys Phe Met Thr Ser Asp Gly Glu
 65                  70                  75                  80

Met Leu Ala Ile Asp Thr Ile Phe Glu Arg Gly Leu Asp Leu Lys Ser
                 85                  90                  95

Ser Asp Phe Ser
            100

<210> SEQ ID NO 12
<211> LENGTH: 104
<212> TYPE: PRT
<213> ORGANISM: Microcoleus chthonoplastes

<400> SEQUENCE: 12

Cys Leu Ser Tyr Asp Thr Gln Ile Leu Thr Val Glu Tyr Gly Ala Val
  1               5                  10                  15

Ala Ile Gly Glu Ile Val Glu Lys Gln Ile Glu Cys Thr Val Tyr Ser
                 20                  25                  30

Val Asp Glu Asn Gly Tyr Val Tyr Thr Gln Pro Ile Ala Gln Trp His
             35                  40                  45

Asn Arg Gly Glu Gln Glu Val Phe Glu Tyr Leu Leu Glu Asp Gly Ala
         50                  55                  60

Thr Ile Arg Ala Thr Lys Asp His Lys Phe Met Thr Asp Glu Asp Gln
 65                  70                  75                  80

Met Leu Pro Ile Asp Gln Ile Phe Glu Gln Gly Leu Glu Leu Lys Gln
                 85                  90                  95

Val Glu Val Leu Gln Pro Val Phe
            100

<210> SEQ ID NO 13
<211> LENGTH: 112
<212> TYPE: PRT
<213> ORGANISM: Oscillatoria limnetica

<400> SEQUENCE: 13

Cys Leu Ser Tyr Asn Thr Glu Val Leu Thr Val Glu Tyr Gly Pro Leu
  1               5                  10                  15

Pro Ile Gly Lys Ile Val Asp Glu Gln Ile His Cys Arg Val Tyr Ser
                 20                  25                  30

Val Asp Glu Asn Gly Phe Val Tyr Thr Gln Ala Ile Ala Gln Trp His
             35                  40                  45

Asp Arg Gly Tyr Gln Glu Ile Phe Ala Tyr Glu Leu Ala Asp Gly Ser
         50                  55                  60

Val Ile Arg Ala Thr Lys Asp His Gln Phe Met Thr Glu Asp Gly Gln
 65                  70                  75                  80

Met Phe Pro Ile Asp Glu Ile Trp Glu Lys Gly Leu Asp Leu Lys Lys
                 85                  90                  95

Leu Pro Thr Val Gln Asp Leu Pro Ala Ala Val Gly Tyr Thr Val Ser
            100                 105                 110

<210> SEQ ID NO 14
<211> LENGTH: 113
<212> TYPE: PRT
<213> ORGANISM: Synechococcus elongatus

<400> SEQUENCE: 14

Cys Leu Ala Ala Asp Thr Glu Val Leu Thr Val Glu Tyr Gly Pro Ile
  1               5                  10                  15

Ala Ile Gly Lys Leu Val Glu Glu Asn Ile Arg Cys Gln Val Tyr Cys
```

```
                20                  25                  30
Cys Asn Pro Asp Gly Tyr Ile Tyr Ser Gln Pro Ile Gly Gln Trp His
            35                  40                  45

Gln Arg Gly Glu Gln Glu Val Ile Glu Tyr Glu Leu Ser Asp Gly Arg
        50                  55                  60

Ile Ile Arg Ala Thr Ala Asp His Arg Phe Met Thr Glu Glu Gly Glu
65                  70                  75                  80

Met Leu Ser Leu Asp Glu Ile Phe Glu Arg Ser Leu Glu Leu Lys Gln
                85                  90                  95

Ile Pro Thr Pro Leu Leu Ala Ile Ala Gln Pro Ser Pro Leu Ala Thr
            100                 105                 110

Ala

<210> SEQ ID NO 15
<211> LENGTH: 107
<212> TYPE: PRT
<213> ORGANISM: Synechococcus PCC7002

<400> SEQUENCE: 15

Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala
            100                 105

<210> SEQ ID NO 16
<211> LENGTH: 117
<212> TYPE: PRT
<213> ORGANISM: Thermosynechococcus elongatus

<400> SEQUENCE: 16

Cys Leu Ser Gly Glu Thr Ala Val Met Thr Val Glu Tyr Gly Ala Val
1               5                   10                  15

Pro Ile Arg Arg Leu Val Gln Glu Arg Leu Ser Cys His Val Tyr Ser
            20                  25                  30

Leu Asp Gly Gln Gly His Leu Tyr Thr Gln Pro Ile Ala Gln Trp His
        35                  40                  45

Phe Gln Gly Phe Arg Pro Val Tyr Glu Tyr Gln Leu Glu Asp Gly Ser
    50                  55                  60

Thr Ile Cys Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Val Ala Ile Ala Pro Arg Gln Ala Leu Leu Gln Gly Leu Lys Pro Ala
            100                 105                 110

Val Gln Met Ser Gly
            115
```

```
<210> SEQ ID NO 17
<211> LENGTH: 101
<212> TYPE: PRT
<213> ORGANISM: Trichodesmium erythraeum

<400> SEQUENCE: 17

Cys Leu Thr Tyr Glu Thr Glu Ile Met Thr Val Glu Tyr Gly Pro Leu
1               5                   10                  15

Pro Ile Gly Lys Ile Val Glu Tyr Arg Ile Glu Cys Thr Val Tyr Thr
            20                  25                  30

Val Asp Lys Asn Gly Tyr Ile Tyr Thr Gln Pro Ile Ala Gln Trp His
        35                  40                  45

Asn Arg Gly Met Gln Glu Val Tyr Glu Tyr Ser Leu Glu Asp Gly Thr
    50                  55                  60

Val Ile Arg Ala Thr Pro Glu His Lys Phe Met Thr Glu Asp Gly Gln
65                  70                  75                  80

Met Leu Pro Ile Asp Glu Ile Phe Glu Arg Asn Leu Asp Leu Lys Cys
                85                  90                  95

Leu Gly Thr Leu Glu
            100

<210> SEQ ID NO 18
<211> LENGTH: 117
<212> TYPE: PRT
<213> ORGANISM: Thermosynechococcusvulcanus

<400> SEQUENCE: 18

Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Gly Ala Leu Ala Gln Gly Leu Lys Pro Ala
            100                 105                 110

Val Gln Met Ser Cys
        115

<210> SEQ ID NO 19
<211> LENGTH: 102
<212> TYPE: PRT
<213> ORGANISM: Artificial Sequence
<220> FEATURE:
<223> OTHER INFORMATION: Peptide consensus sequence

<400> SEQUENCE: 19

Cys Leu Ser Tyr Asp Thr Glu Ile Leu Thr Val Glu Tyr Gly Ala Val
1               5                   10                  15

Pro Ile Gly Lys Ile Val Glu Glu Asn Ile Glu Cys Thr Val Tyr Ser
            20                  25                  30

Val Asp Glu Asn Gly Phe Val Tyr Thr Gln Pro Ile Ala Gln Trp His
```

```
                35                  40                  45
Asp Arg Gly Glu Gln Glu Val Phe Glu Tyr Cys Leu Glu Asp Gly Ser
             50                  55                  60

Thr Ile Arg Ala Thr Lys Asp His Lys Phe Met Thr Glu Asp Gly Glu
 65                  70                  75                  80

Met Leu Pro Ile Asp Glu Ile Phe Glu Gln Gly Leu Asp Leu Lys Gln
                 85                  90                  95

Val Lys Gly Leu Pro Asp
            100

<210> SEQ ID NO 20
<211> LENGTH: 102
<212> TYPE: PRT
<213> ORGANISM: Artificial Sequence
<220> FEATURE:
<223> OTHER INFORMATION: Peptide consensus sequence

<400> SEQUENCE: 20

Cys Leu Ser Tyr Glu Thr Glu Ile Leu Thr Val Glu Tyr Gly Leu Leu
 1               5                  10                  15

Pro Ile Gly Lys Ile Val Glu Lys Arg Ile Glu Ser Thr Val Tyr Ser
                20                  25                  30

Val Asp Asn Asn Gly Asn Ile Tyr Thr Gln Pro Val Ala Gln Trp His
             35                  40                  45

Asp Arg Gly Glu Gln Glu Val Phe Glu Tyr Ser Leu Glu Asp Gly Ser
             50                  55                  60

Leu Ile Arg Ala Thr Lys Asp His Lys Phe Met Thr Val Asp Gly Gln
 65                  70                  75                  80

Met Leu Pro Ile Asp Glu Ile Phe Glu Arg Glu Leu Asp Leu Met Arg
                 85                  90                  95

Val Asp Asn Leu Pro Asn
            100

<210> SEQ ID NO 21
<211> LENGTH: 102
<212> TYPE: PRT
<213> ORGANISM: Nostoc punctiforme
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (59)..(59)
<223> OTHER INFORMATION: Xaa is Ala or Ser

<400> SEQUENCE: 21

Cys Leu Ser Tyr Glu Thr Glu Ile Leu Thr Val Glu Tyr Gly Leu Leu
 1               5                  10                  15

Pro Ile Gly Lys Ile Val Glu Lys Arg Ile Glu Xaa Thr Val Tyr Ser
                20                  25                  30

Val Asp Asn Asn Gly Asn Ile Tyr Thr Gln Pro Val Ala Gln Trp His
             35                  40                  45

Asp Arg Gly Glu Gln Glu Val Phe Glu Tyr Xaa Leu Glu Asp Gly Ser
             50                  55                  60

Leu Ile Arg Ala Thr Lys Asp His Lys Phe Met Thr Val Asp Gly Gln
 65                  70                  75                  80

Met Leu Pro Ile Asp Glu Ile Phe Glu Arg Glu Leu Asp Leu Met Arg
                 85                  90                  95
```

```
Val Asp Asn Leu Pro Asn
            100
```

<210> SEQ ID NO 22
<211> LENGTH: 123
<212> TYPE: PRT
<213> ORGANISM: Synechocystis PCC6803
<220> FEATURE:
<221> NAME/KEY: MISC_FEATURE
<222> LOCATION: (28)..(28)
<223> OTHER INFORMATION: Xaa is Ala or Ser

<400> SEQUENCE: 22

```
Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Xaa Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120
```

<210> SEQ ID NO 23
<211> LENGTH: 110
<212> TYPE: PRT
<213> ORGANISM: Aphanothece halophytica
<220> FEATURE:
<221> NAME/KEY: MISC_FEATURE
<222> LOCATION: (28)..(28)
<223> OTHER INFORMATION: Xaa is Ala or Ser

<400> SEQUENCE: 23

```
Cys Leu Ser Tyr Asp Thr Glu Ile Trp Thr Val Glu Tyr Gly Ala Met
1               5                   10                  15

Pro Ile Gly Lys Ile Val Glu Glu Lys Ile Glu Xaa Ser Val Tyr Thr
            20                  25                  30

Val Asp Glu Asn Gly Phe Val Tyr Thr Gln Pro Ile Ala Gln Trp His
        35                  40                  45

Pro Arg Gly Gln Gln Glu Ile Ile Glu Tyr Thr Leu Glu Asp Gly Arg
    50                  55                  60

Lys Ile Arg Ala Thr Lys Asp His Lys Met Met Thr Glu Ser Gly Glu
65                  70                  75                  80

Met Leu Pro Ile Glu Glu Ile Phe Gln Arg Gly Leu Asp Leu Lys Val
                85                  90                  95

Glu Thr Phe His Glu Met Ser Leu Leu Arg Arg Gly Ala Lys
            100                 105                 110
```

<210> SEQ ID NO 24
<211> LENGTH: 101
<212> TYPE: PRT
<213> ORGANISM: Aphanizomenon ovalisporum
<220> FEATURE:
<221> NAME/KEY: MISC_FEATURE -continued
<222> LOCATION: (28)..(28)
<223> OTHER INFORMATION: Xaa is Ala or Ser

<400> SEQUENCE: 24

Cys Leu Ser Ala Asp Thr Glu Ile Leu Thr Val Glu Tyr Gly Phe Leu
1               5                   10                  15

Pro Ile Gly Glu Ile Val Gly Lys Ala Ile Glu Xaa Arg Val Tyr Ser
            20                  25                  30

Val Asp Gly Asn Gly Asn Ile Tyr Thr Gln Ser Ile Ala Gln Trp His
        35                  40                  45

Asn Arg Gly Glu Gln Glu Val Phe Gly Tyr Thr Leu Glu Asp Gly Ser
    50                  55                  60

Ile Ile Arg Ala Thr Lys Asp His Lys Phe Met Thr Thr Asp Gly Glu
65                  70                  75                  80

Met Leu Pro Ile Asp Glu Ile Phe Ala Arg Gln Leu Asp Leu Met Gln
                85                  90                  95

Val Gln Gly Leu His
            100

<210> SEQ ID NO 25
<211> LENGTH: 102
<212> TYPE: PRT
<213> ORGANISM: Anabaena PCC7120
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (59)..(59)
<223> OTHER INFORMATION: Xaa is Ala or Ser

<400> SEQUENCE: 25

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Xaa Ser Val Phe Ser
            20                  25                  30

Ile Asn Asn Gly Ile Val Tyr Thr Gln Pro Ile Ala Gln Trp His
        35                  40                  45

His Arg Gly Lys Gln Glu Val Phe Gly Tyr Xaa Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 26
<211> LENGTH: 102
<212> TYPE: PRT
<213> ORGANISM: Anabaena variabilis
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (59)..(59)
<223> OTHER INFORMATION: Xaa is Ala or Ser

<400> SEQUENCE: 26

```
Cys Leu Ser Tyr Asp Thr Glu Val Leu Thr Val Glu Tyr Gly Phe Val
1               5                   10                  15

Pro Ile Gly Glu Ile Val Asp Lys Gly Ile Xaa Ser Val Phe Ser
            20                  25                  30

Ile Asp Ser Asn Gly Ile Val Tyr Thr Gln Pro Ile Ala Gln Trp His
        35                  40                  45

His Arg Gly Lys Gln Glu Val Phe Glu Tyr Xaa Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100
```

```
<210> SEQ ID NO 27
<211> LENGTH: 118
<212> TYPE: PRT
<213> ORGANISM: Cylindrospermopsis raciborskii
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (59)..(59)
<223> OTHER INFORMATION: Xaa is Ala or Ser

<400> SEQUENCE: 27

Cys Leu Ser Tyr Glu Thr Glu Val Leu Thr Leu Glu Tyr Gly Phe Val
1               5                   10                  15

Pro Ile Gly Glu Ile Val Asn Lys Gln Met Val Xaa Thr Val Phe Ser
            20                  25                  30

Leu Asn Asp Ser Gly Asn Val Tyr Thr Gln Pro Ile Gly Gln Trp His
        35                  40                  45

Asp Arg Gly Val Gln Asp Leu Tyr Glu Tyr Xaa Leu Asp Asp Gly Ser
    50                  55                  60

Thr Ile Arg Ala Thr Lys Asp His Lys Phe Met Thr Thr Gln Gly Glu
65                  70                  75                  80

Met Val Pro Ile Asp Glu Ile Phe His Gln Gly Trp Glu Leu Val Gln
                85                  90                  95

Val Ser Gly Ile Ser Lys Leu Val Gln Gln Arg Thr Leu Pro Phe Ile
            100                 105                 110

Ile Val Asp Arg Lys Leu
            115
```

```
<210> SEQ ID NO 28
<211> LENGTH: 99
<212> TYPE: PRT
<213> ORGANISM: Cyanothece CCY0110
<220> FEATURE:
<221> NAME/KEY: MISC_FEATURE
<222> LOCATION: (28)..(28)
<223> OTHER INFORMATION: Xaa is Ala or Ser

<400> SEQUENCE: 28

Cys Leu Ser Tyr Asp Thr Glu Ile Leu Thr Val Glu Tyr Gly Pro Met
1               5                   10                  15

Pro Ile Gly Lys Ile Val Glu Glu Asn Ile Asn Xaa Ser Val Tyr Thr
            20                  25                  30
```

Val Asn Lys Asn Gly Phe Val Tyr Thr Gln Ser Ile Ala Gln Trp His
         35                  40                  45

His Arg Gly Glu Gln Glu Val Phe Glu Tyr Tyr Leu Glu Asp Gly Glu
 50                  55                  60

Thr Ile Arg Ala Thr Lys Asp His Lys Phe Met Thr Thr Glu Gly Lys
65                  70                  75                  80

Met Leu Pro Ile Asp Glu Ile Phe Glu Asn Asn Leu Asp Leu Lys Lys
                85                  90                  95

Leu Thr Val

<210> SEQ ID NO 29
<211> LENGTH: 99
<212> TYPE: PRT
<213> ORGANISM: Cyanothece PCC8801
<220> FEATURE:
<221> NAME/KEY: MISC_FEATURE
<222> LOCATION: (28)..(28)
<223> OTHER INFORMATION: Xaa is Ala or Ser

<400> SEQUENCE: 29

Cys Leu Ser Tyr Asp Thr Glu Ile Leu Thr Val Glu Tyr Gly Ala Ile
1               5                   10                  15

Pro Ile Gly Lys Val Val Glu Glu Asn Ile Asp Xaa Thr Val Tyr Thr
                20                  25                  30

Val Asp Lys Asn Gly Phe Val Tyr Thr Gln Asn Ile Ala Gln Trp His
         35                  40                  45

Leu Arg Gly Gln Gln Glu Val Phe Glu Tyr Tyr Leu Asp Asp Gly Ser
 50                  55                  60

Ile Leu Arg Ala Thr Lys Asp His Gln Phe Met Thr Leu Glu Gly Glu
65                  70                  75                  80

Met Leu Pro Ile His Glu Ile Phe Glu Arg Gly Leu Glu Leu Lys Lys
                85                  90                  95

Ile Lys Ile

<210> SEQ ID NO 30
<211> LENGTH: 106
<212> TYPE: PRT
<213> ORGANISM: Crocosphaera watsonii
<220> FEATURE:
<221> NAME/KEY: MISC_FEATURE
<222> LOCATION: (28)..(28)
<223> OTHER INFORMATION: Xaa is Ala or Ser

<400> SEQUENCE: 30

Cys Leu Ser Tyr Asp Thr Glu Ile Leu Thr Val Glu Tyr Gly Ala Met
1               5                   10                  15

Tyr Ile Gly Lys Ile Val Glu Glu Asn Ile Asn Xaa Thr Val Tyr Thr
                20                  25                  30

Val Asp Lys Asn Gly Phe Val Tyr Thr Gln Thr Ile Ala Gln Trp His
         35                  40                  45

Asn Arg Gly Glu Gln Glu Ile Phe Glu Tyr Asp Leu Glu Asp Gly Ser
 50                  55                  60

Lys Ile Lys Ala Thr Lys Asp His Lys Phe Met Thr Ile Asp Gly Glu
65                  70                  75                  80

Met Leu Pro Ile Asp Glu Ile Phe Glu Lys Asn Leu Asp Leu Lys Gln
                85                  90                  95

Val Val Ser His Pro Asp Asp Tyr Leu Val
                100                 105

<210> SEQ ID NO 31
<211> LENGTH: 100
<212> TYPE: PRT
<213> ORGANISM: Microcystis aeruginosa
<220> FEATURE:
<221> NAME/KEY: MISC_FEATURE
<222> LOCATION: (28)..(28)
<223> OTHER INFORMATION: Xaa is Ala or Ser

<400> SEQUENCE: 31

```
Cys Leu Gly Gly Glu Thr Leu Ile Leu Thr Glu Glu Tyr Gly Leu Leu
1               5                   10                  15

Pro Ile Ala Lys Ile Val Ser Glu Glu Ile Asn Xaa Thr Val Tyr Thr
            20                  25                  30

Val Asp Gln Asn Gly Phe Val Tyr Ser Gln Pro Ile Ser Gln Trp His
        35                  40                  45

Glu Arg Gly Leu Gln Glu Val Phe Glu Tyr Thr Leu Glu Asn Gly Gln
    50                  55                  60

Thr Ile Gln Ala Thr Lys Asp His Lys Phe Met Thr Ser Asp Gly Glu
65                  70                  75                  80

Met Leu Ala Ile Asp Thr Ile Phe Glu Arg Gly Leu Asp Leu Lys Ser
                85                  90                  95

Ser Asp Phe Ser
            100
```

<210> SEQ ID NO 32
<211> LENGTH: 104
<212> TYPE: PRT
<213> ORGANISM: Microcoleus chthonoplastes
<220> FEATURE:
<221> NAME/KEY: MISC_FEATURE
<222> LOCATION: (28)..(28)
<223> OTHER INFORMATION: Xaa is Ala or Ser

<400> SEQUENCE: 32

```
Cys Leu Ser Tyr Asp Thr Gln Ile Leu Thr Val Glu Tyr Gly Ala Val
1               5                   10                  15

Ala Ile Gly Glu Ile Val Glu Lys Gln Ile Glu Xaa Thr Val Tyr Ser
            20                  25                  30

Val Asp Glu Asn Gly Tyr Val Tyr Thr Gln Pro Ile Ala Gln Trp His
        35                  40                  45

Asn Arg Gly Glu Gln Glu Val Phe Glu Tyr Leu Leu Glu Asp Gly Ala
    50                  55                  60

Thr Ile Arg Ala Thr Lys Asp His Lys Phe Met Thr Asp Glu Asp Gln
65                  70                  75                  80

Met Leu Pro Ile Asp Gln Ile Phe Glu Gln Gly Leu Glu Leu Lys Gln
                85                  90                  95

Val Glu Val Leu Gln Pro Val Phe
            100
```

<210> SEQ ID NO 33
<211> LENGTH: 112
<212> TYPE: PRT
<213> ORGANISM: Oscillatoria limnetica
<220> FEATURE:
<221> NAME/KEY: MISC_FEATURE
<222> LOCATION: (28)..(28)
<223> OTHER INFORMATION: Xaa is Ala or Ser

<400> SEQUENCE: 33

```
Cys Leu Ser Tyr Asn Thr Glu Val Leu Thr Val Glu Tyr Gly Pro Leu
```

```
                1               5                  10                  15
         Pro Ile Gly Lys Ile Val Asp Glu Gln Ile His Xaa Arg Val Tyr Ser
                        20                  25                  30

Val Asp Glu Asn Gly Phe Val Tyr Thr Gln Ala Ile Ala Gln Trp His
                        35                  40                  45

Asp Arg Gly Tyr Gln Glu Ile Phe Ala Tyr Glu Leu Ala Asp Gly Ser
                        50                  55                  60

Val Ile Arg Ala Thr Lys Asp His Gln Phe Met Thr Glu Asp Gly Gln
         65                  70                  75                  80

Met Phe Pro Ile Asp Glu Ile Trp Glu Lys Gly Leu Asp Leu Lys Lys
                        85                  90                  95

Leu Pro Thr Val Gln Asp Leu Pro Ala Ala Val Gly Tyr Thr Val Ser
                        100                 105                 110
```

<210> SEQ ID NO 34
<211> LENGTH: 113
<212> TYPE: PRT
<213> ORGANISM: Synechococcus elongatus
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (32)..(32)
<223> OTHER INFORMATION: Xaa is Ala or Ser
<220> FEATURE:
<221> NAME/KEY: MISC_FEATURE
<222> LOCATION: (33)..(33)
<223> OTHER INFORMATION: Xaa is Ala or Ser

<400> SEQUENCE: 34

```
         Cys Leu Ala Ala Asp Thr Glu Val Leu Thr Val Glu Tyr Gly Pro Ile
         1               5                  10                  15

Ala Ile Gly Lys Leu Val Glu Glu Asn Ile Arg Xaa Gln Val Tyr Xaa
                        20                  25                  30

Xaa Asn Pro Asp Gly Tyr Ile Tyr Ser Gln Pro Ile Gly Gln Trp His
                        35                  40                  45

Gln Arg Gly Glu Gln Val Ile Glu Tyr Glu Leu Ser Asp Gly Arg
                        50                  55                  60

Ile Ile Arg Ala Thr Ala Asp His Arg Phe Met Thr Glu Glu Gly Glu
         65                  70                  75                  80

Met Leu Ser Leu Asp Glu Ile Phe Glu Arg Ser Leu Glu Leu Lys Gln
                        85                  90                  95

Ile Pro Thr Pro Leu Leu Ala Ile Ala Gln Pro Ser Pro Leu Ala Thr
                        100                 105                 110

Ala
```

<210> SEQ ID NO 35
<211> LENGTH: 107
<212> TYPE: PRT
<213> ORGANISM: Synechococcus PCC7002
<220> FEATURE:
<221> NAME/KEY: MISC_FEATURE
<222> LOCATION: (28)..(28)
<223> OTHER INFORMATION: Xaa is Ala or Ser

<400> SEQUENCE: 35

```
         Cys Leu Ala Gly Gly Thr Pro Val Val Thr Val Glu Tyr Gly Val Leu
         1               5                  10                  15

Pro Ile Gln Thr Ile Val Glu Gln Glu Leu Leu Xaa His Val Tyr Ser
```

```
                20                  25                  30

Val Asp Ala Gln Gly Leu Ile Tyr Ala Gln Leu Ile Glu Gln Trp His
            35                  40                  45

Gln Arg Gly Asp Arg Leu Leu Tyr Glu Tyr Glu Leu Glu Asn Gly Gln
        50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala
            100                 105

<210> SEQ ID NO 36
<211> LENGTH: 117
<212> TYPE: PRT
<213> ORGANISM: Thermosynechococcus elongatus
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (67)..(67)
<223> OTHER INFORMATION: Xaa is Ala or Ser

<400> SEQUENCE: 36

Cys Leu Ser Gly Glu Thr Ala Val Met Thr Val Glu Tyr Gly Ala Val
1               5                   10                  15

Pro Ile Arg Arg Leu Val Gln Glu Arg Leu Ser Xaa His Val Tyr Ser
            20                  25                  30

Leu Asp Gly Gln Gly His Leu Tyr Thr Gln Pro Ile Ala Gln Trp His
            35                  40                  45

Phe Gln Gly Phe Arg Pro Val Tyr Glu Tyr Gln Leu Glu Asp Gly Ser
        50                  55                  60

Thr Ile Xaa Ala Thr Pro Asp His Arg Phe Met Thr Thr Arg Gly Gln
65                  70                  75                  80

Met Leu Pro Ile Glu Gln Ile Phe Gln Glu Gly Leu Glu Leu Trp Gln
                85                  90                  95

Val Ala Ile Ala Pro Arg Gln Ala Leu Leu Gln Gly Leu Lys Pro Ala
            100                 105                 110

Val Gln Met Ser Gly
        115

<210> SEQ ID NO 37
<211> LENGTH: 101
<212> TYPE: PRT
<213> ORGANISM: Trichodesmium erythraeum
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (96)..(96)
<223> OTHER INFORMATION: Xaa is Ala or Ser

<400> SEQUENCE: 37

Cys Leu Thr Tyr Glu Thr Glu Ile Met Thr Val Glu Tyr Gly Pro Leu
1               5                   10                  15

Pro Ile Gly Lys Ile Val Glu Tyr Arg Ile Glu Xaa Thr Val Tyr Thr
            20                  25                  30
```

-continued

Val Asp Lys Asn Gly Tyr Ile Tyr Thr Gln Pro Ile Ala Gln Trp His
         35                  40                  45

Asn Arg Gly Met Gln Glu Val Tyr Glu Tyr Ser Leu Glu Asp Gly Thr
 50                  55                  60

Val Ile Arg Ala Thr Pro Glu His Lys Phe Met Thr Glu Asp Gly Gln
 65                  70                  75                  80

Met Leu Pro Ile Asp Glu Ile Phe Glu Arg Asn Leu Asp Leu Lys Xaa
                 85                  90                  95

Leu Gly Thr Leu Glu
             100

<210> SEQ ID NO 38
<211> LENGTH: 117
<212> TYPE: PRT
<213> ORGANISM: Thermosynechococcusvulcanus
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (67)..(67)
<223> OTHER INFORMATION: Xaa is Ala or Ser
<220> FEATURE:
<221> NAME/KEY: MISC_FEATURE
<222> LOCATION: (117)..(117)
<223> OTHER INFORMATION: Xaa is Ala or Ser

<400> SEQUENCE: 38

Cys Leu Ser Gly Glu Thr Ala Val Met Thr Val Glu Tyr Gly Ala Ile
 1               5                  10                  15

Pro Ile Arg Arg Leu Val Gln Glu Arg Leu Ile Xaa Gln Val Tyr Ser
                 20                  25                  30

Leu Asp Pro Gln Gly His Leu Tyr Thr Gln Pro Ile Ala Gln Trp His
             35                  40                  45

Phe Gln Gly Phe Arg Pro Val Tyr Ala Tyr Gln Leu Glu Asp Gly Ser
 50                  55                  60

Thr Ile Xaa Ala Thr Pro Asp His Arg Phe Met Thr Thr Ser Gly Gln
 65                  70                  75                  80

Met Leu Pro Ile Glu Gln Ile Phe Arg Glu Gly Leu Glu Leu Trp Gln
                 85                  90                  95

Val Ala Ile Ala Pro Pro Gly Leu Ala Gly Leu Lys Pro Ala
             100                 105                 110

Val Gln Met Ser Xaa
         115

<210> SEQ ID NO 39
<211> LENGTH: 36
<212> TYPE: PRT
<213> ORGANISM: Nostoc punctiforme

<400> SEQUENCE: 39

Met Ile Lys Ile Ala Thr Arg Lys Tyr Leu Gly Lys Gln Asn Val Tyr
 1               5                  10                  15

Asp Ile Gly Val Glu Arg Asp His Asn Phe Ala Leu Lys Asn Gly Phe
                 20                  25                  30

Ile Ala Ser Asn
         35

<210> SEQ ID NO 40
<211> LENGTH: 36

```
<212> TYPE: PRT
<213> ORGANISM: Synechocystis PCC6803

<400> SEQUENCE: 40

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35

<210> SEQ ID NO 41
<211> LENGTH: 36
<212> TYPE: PRT
<213> ORGANISM: Aphanothece halophytica

<400> SEQUENCE: 41

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Asn
        35

<210> SEQ ID NO 42
<211> LENGTH: 36
<212> TYPE: PRT
<213> ORGANISM: Aphanizomenon ovalisporum

<400> SEQUENCE: 42

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Asn
        35

<210> SEQ ID NO 43
<211> LENGTH: 36
<212> TYPE: PRT
<213> ORGANISM: Anabaena PCC7120

<400> SEQUENCE: 43

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35

<210> SEQ ID NO 44
<211> LENGTH: 36
<212> TYPE: PRT
<213> ORGANISM: Anabaena variabilis

<400> SEQUENCE: 44

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30
```

Ile Ala Ser Asn
        35

<210> SEQ ID NO 45
<211> LENGTH: 36
<212> TYPE: PRT
<213> ORGANISM: Cylindrospermopsis raciborskii

<400> SEQUENCE: 45

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Asn
        35

<210> SEQ ID NO 46
<211> LENGTH: 36
<212> TYPE: PRT
<213> ORGANISM: Cyanothece CCY0110

<400> SEQUENCE: 46

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Asn
        35

<210> SEQ ID NO 47
<211> LENGTH: 36
<212> TYPE: PRT
<213> ORGANISM: Cyanothece PCC8801

<400> SEQUENCE: 47

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Asn
        35

<210> SEQ ID NO 48
<211> LENGTH: 36
<212> TYPE: PRT
<213> ORGANISM: Crocosphaera watsonii

<400> SEQUENCE: 48

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Asn
        35

<210> SEQ ID NO 49
<211> LENGTH: 36
<212> TYPE: PRT
<213> ORGANISM: Microcystis aeruginosa

<400> SEQUENCE: 49

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Asn
        35

<210> SEQ ID NO 50
<211> LENGTH: 36
<212> TYPE: PRT
<213> ORGANISM: Microcoleus chthonoplastes

<400> SEQUENCE: 50

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Asn
        35

<210> SEQ ID NO 51
<211> LENGTH: 36
<212> TYPE: PRT
<213> ORGANISM: Oscillatoria limnetica

<400> SEQUENCE: 51

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Asn
        35

<210> SEQ ID NO 52
<211> LENGTH: 36
<212> TYPE: PRT
<213> ORGANISM: Synechococcus elongatus

<400> SEQUENCE: 52

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Asn
        35

<210> SEQ ID NO 53
<211> LENGTH: 36
<212> TYPE: PRT
<213> ORGANISM: Synechococcus PCC7002

<400> SEQUENCE: 53

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Asn
        35

<210> SEQ ID NO 54

```
<211> LENGTH: 35
<212> TYPE: PRT
<213> ORGANISM: Thermosynechococcus elongatus

<400> SEQUENCE: 54

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Asn
        35

<210> SEQ ID NO 55
<211> LENGTH: 36
<212> TYPE: PRT
<213> ORGANISM: Trichodesmium erythraeum

<400> SEQUENCE: 55

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Asn
        35

<210> SEQ ID NO 56
<211> LENGTH: 35
<212> TYPE: PRT
<213> ORGANISM: Thermosynechococcus vulcanus

<400> SEQUENCE: 56

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Asn
        35

<210> SEQ ID NO 57
<211> LENGTH: 36
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 57

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa
        35

<210> SEQ ID NO 58
<211> LENGTH: 36
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
```

<400> SEQUENCE: 58

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa
        35
```

<210> SEQ ID NO 59
<211> LENGTH: 36
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 59

```
Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa
        35
```

<210> SEQ ID NO 60
<211> LENGTH: 36
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 60

```
Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa
        35
```

<210> SEQ ID NO 61
<211> LENGTH: 36
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 61

```
Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa
        35
```

<210> SEQ ID NO 62
<211> LENGTH: 36
<212> TYPE: PRT

```
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 62

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa
        35

<210> SEQ ID NO 63
<211> LENGTH: 36
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 63

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa
        35

<210> SEQ ID NO 64
<211> LENGTH: 36
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 64

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa
        35

<210> SEQ ID NO 65
<211> LENGTH: 36
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 65

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa
        35
```

```
<210> SEQ ID NO 66
<211> LENGTH: 36
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 66

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa
        35

<210> SEQ ID NO 67
<211> LENGTH: 36
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 67

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa
        35

<210> SEQ ID NO 68
<211> LENGTH: 36
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 68

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa
        35

<210> SEQ ID NO 69
<211> LENGTH: 36
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 69

Met Val Lys Ile Val Arg Arg Gln Ser Leu Gly Val Gln Asn Val Tyr
1               5                   10                  15
```

Asp Ile Gly Val Glu Lys Asp His Asn Phe Cys Leu Ala Ser Gly Glu
            20                  25                  30

Ile Ala Ser Xaa
        35

<210> SEQ ID NO 70
<211> LENGTH: 36
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 70

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa
        35

<210> SEQ ID NO 71
<211> LENGTH: 36
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 71

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa
        35

<210> SEQ ID NO 72
<211> LENGTH: 35
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 72

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa
        35

<210> SEQ ID NO 73
<211> LENGTH: 36
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 73

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa
            35

<210> SEQ ID NO 74
<211> LENGTH: 35
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 74

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
                20                  25                  30

Ala Ala Xaa
        35

<210> SEQ ID NO 75
<211> LENGTH: 36
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 75

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
                20                  25                  30

Ile Ala Ser Xaa
            35

<210> SEQ ID NO 76
<211> LENGTH: 36
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 76

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
                20                  25                  30

Ile Ala Ala Xaa
            35

<210> SEQ ID NO 77
<211> LENGTH: 36
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 77

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa
        35

<210> SEQ ID NO 78
<211> LENGTH: 36
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 78

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa
        35

<210> SEQ ID NO 79
<211> LENGTH: 36
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 79

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa
        35

<210> SEQ ID NO 80
<211> LENGTH: 36
<212> TYPE: PRT
<213> ORGANISM: Anabaena variabilis
<220> FEATURE:

-continued

```
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 80

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa
        35

<210> SEQ ID NO 81
<211> LENGTH: 36
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 81

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa
        35

<210> SEQ ID NO 82
<211> LENGTH: 36
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 82

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa
        35

<210> SEQ ID NO 83
<211> LENGTH: 36
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
```

```
<400> SEQUENCE: 83

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
                20                  25                  30

Ile Ala Ser Xaa
            35

<210> SEQ ID NO 84
<211> LENGTH: 36
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 84

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Xaa
            35

<210> SEQ ID NO 85
<211> LENGTH: 36
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 85

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
                20                  25                  30

Ile Ala Ser Xaa
            35

<210> SEQ ID NO 86
<211> LENGTH: 36
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 86

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30
```

Ile Ala Ser Xaa
        35

<210> SEQ ID NO 87
<211> LENGTH: 36
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 87

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa
        35

<210> SEQ ID NO 88
<211> LENGTH: 36
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 88

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa
        35

<210> SEQ ID NO 89
<211> LENGTH: 36
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 89

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa
        35

<210> SEQ ID NO 90
<211> LENGTH: 35

```
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 90

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa
        35

<210> SEQ ID NO 91
<211> LENGTH: 36
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 91

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa
        35

<210> SEQ ID NO 92
<211> LENGTH: 35
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 92

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa
        35

<210> SEQ ID NO 93
<211> LENGTH: 36
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe
```

-continued

```
<400> SEQUENCE: 93

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa
            35

<210> SEQ ID NO 94
<211> LENGTH: 36
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 94

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa
            35

<210> SEQ ID NO 95
<211> LENGTH: 36
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 95

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa
            35

<210> SEQ ID NO 96
<211> LENGTH: 36
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 96

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa
            35

<210> SEQ ID NO 97
<211> LENGTH: 36
<212> TYPE: PRT
<213> ORGANISM: Anabaena PCC7120
```

```
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 97

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa
        35

<210> SEQ ID NO 98
<211> LENGTH: 36
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 98

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa
        35

<210> SEQ ID NO 99
<211> LENGTH: 36
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 99

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa
        35

<210> SEQ ID NO 100
<211> LENGTH: 36
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 100

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa
        35
```

<210> SEQ ID NO 101
<211> LENGTH: 36
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 101

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa
        35

<210> SEQ ID NO 102
<211> LENGTH: 36
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 102

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa
        35

<210> SEQ ID NO 103
<211> LENGTH: 36
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 103

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa
        35

<210> SEQ ID NO 104
<211> LENGTH: 36
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 104

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu

```
                    20                  25                  30

Ile Ala Ser Xaa
        35

<210> SEQ ID NO 105
<211> LENGTH: 36
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 105

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Ala Ser Xaa
        35

<210> SEQ ID NO 106
<211> LENGTH: 36
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 106

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
                20                  25                  30

Val Ala Ser Xaa
        35

<210> SEQ ID NO 107
<211> LENGTH: 36
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 107

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Xaa
        35

<210> SEQ ID NO 108
<211> LENGTH: 35
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 108
```

```
Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa
        35

<210> SEQ ID NO 109
<211> LENGTH: 36
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 109

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa
        35

<210> SEQ ID NO 110
<211> LENGTH: 35
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 110

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa
        35

<210> SEQ ID NO 111
<211> LENGTH: 36
<212> TYPE: PRT
<213> ORGANISM: Nostoc punctiforme

<400> SEQUENCE: 111

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala
        35

<210> SEQ ID NO 112
<211> LENGTH: 36
<212> TYPE: PRT
<213> ORGANISM: Synechocystis PCC6803

<400> SEQUENCE: 112

Met Val Lys Val Ile Gly Arg Arg Ser Leu Gly Val Gln Arg Ile Phe
1               5                   10                  15
```

```
Asp Ile Gly Leu Pro Gln Asp His Asn Phe Leu Leu Ala Asn Gly Ala
            20                  25                  30

Ile Ala Ala Ala
        35

<210> SEQ ID NO 113
<211> LENGTH: 36
<212> TYPE: PRT
<213> ORGANISM: Aphanothece halophytica

<400> SEQUENCE: 113

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala
        35

<210> SEQ ID NO 114
<211> LENGTH: 36
<212> TYPE: PRT
<213> ORGANISM: Aphanizomenon ovalisporum

<400> SEQUENCE: 114

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Ala
        35

<210> SEQ ID NO 115
<211> LENGTH: 36
<212> TYPE: PRT
<213> ORGANISM: Anabaena PCC7120

<400> SEQUENCE: 115

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala
        35

<210> SEQ ID NO 116
<211> LENGTH: 36
<212> TYPE: PRT
<213> ORGANISM: Anabaena variabilis

<400> SEQUENCE: 116

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala
        35

<210> SEQ ID NO 117
<211> LENGTH: 36
<212> TYPE: PRT
```

```
<213> ORGANISM: Cylindrospermopsis raciborskii

<400> SEQUENCE: 117

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala
        35

<210> SEQ ID NO 118
<211> LENGTH: 36
<212> TYPE: PRT
<213> ORGANISM: Cyanothece CCY0110

<400> SEQUENCE: 118

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala
        35

<210> SEQ ID NO 119
<211> LENGTH: 36
<212> TYPE: PRT
<213> ORGANISM: Cyanothece PCC8801

<400> SEQUENCE: 119

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala
        35

<210> SEQ ID NO 120
<211> LENGTH: 36
<212> TYPE: PRT
<213> ORGANISM: Crocosphaera watsonii

<400> SEQUENCE: 120

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala
        35

<210> SEQ ID NO 121
<211> LENGTH: 36
<212> TYPE: PRT
<213> ORGANISM: Microcystis aeruginosa

<400> SEQUENCE: 121

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala
```

-continued

```
<210> SEQ ID NO 122
<211> LENGTH: 36
<212> TYPE: PRT
<213> ORGANISM: Microcoleus chthonoplastes

<400> SEQUENCE: 122

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala
            35

<210> SEQ ID NO 123
<211> LENGTH: 36
<212> TYPE: PRT
<213> ORGANISM: Oscillatoria limnetica

<400> SEQUENCE: 123

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala
            35

<210> SEQ ID NO 124
<211> LENGTH: 36
<212> TYPE: PRT
<213> ORGANISM: Synechococcus elongatus

<400> SEQUENCE: 124

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala
            35

<210> SEQ ID NO 125
<211> LENGTH: 36
<212> TYPE: PRT
<213> ORGANISM: Synechococcus PCC7002

<400> SEQUENCE: 125

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala
            35

<210> SEQ ID NO 126
<211> LENGTH: 35
<212> TYPE: PRT
<213> ORGANISM: Thermosynechococcus elongatus

<400> SEQUENCE: 126

Met Lys Ile Val Gly Arg Arg Leu Met Gly Trp Gln Ala Val Tyr Asp
```

```
                1               5                   10                  15
Ile Gly Leu Ala Ala Asp His Asn Phe Val Leu Ala Asn Gly Ala Ile
                20                  25                  30

Ala Ala Ala
        35

<210> SEQ ID NO 127
<211> LENGTH: 36
<212> TYPE: PRT
<213> ORGANISM: Trichodesmium erythraeum

<400> SEQUENCE: 127

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Ala
        35

<210> SEQ ID NO 128
<211> LENGTH: 35
<212> TYPE: PRT
<213> ORGANISM: Thermosynechococcus vulcanus

<400> SEQUENCE: 128

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
                20                  25                  30

Ala Ala Ala
        35

<210> SEQ ID NO 129
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 129

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
                20                  25                  30

Ile Ala Ser Xaa Xaa Phe Asn
        35

<210> SEQ ID NO 130
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
```

-continued

```
<223> OTHER INFORMATION: Xaa is any amino acid excluding Cys

<400> SEQUENCE: 130

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 131
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 131

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 132
<211> LENGTH: 39
<212> TYPE: PRT
<213> ORGANISM: Aphanizomenon ovalisporum
<220> FEATURE:
<221> NAME Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
            35

<210> SEQ ID NO 134
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 134

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
            35

<210> SEQ ID NO 135
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 135

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
            35

<210> SEQ ID NO 136
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 136

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu

Ile Ala Ser Xaa Xaa Phe Asn
        35

<210> SEQ ID NO 137
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 137

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 138
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 138

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 139
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 139

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 140
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 140

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 141
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 141

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 142
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 142

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 143
<211> LENGTH: 39

```
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 143

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Xaa Xaa Phe Asn
        35

<210> SEQ ID NO 144
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 144

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
                20                  25                  30

Ala Ala Xaa Xaa Phe Asn
        35

<210> SEQ ID NO 145
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Asn

<400> SEQUENCE: 145

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa Xaa Phe Asn
        35

<210> SEQ ID NO 146
<211> LENGTH: 38
<212> TYPE: PRT
<213> ORGANISM: Thermosynechococcus vulcanus
<220> FEATURE:
<221> NAME/KEY: MISC_FEATURE
```

```
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 146

Met Lys Ile Val Gly Arg Arg Leu Val Gly Trp Gln Ala Val Tyr Asp
 1               5                  10                  15

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 147
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 147

Met Ile Lys Ile Ala Thr Arg Lys Tyr Leu Gly Lys Gln Asn Val Tyr
 1               5                  10                  15

Asp Ile Gly Val Glu Arg Asp His Asn Phe Ala Leu Lys Asn Gly Phe
            20                  25                  30

Ile Ala Ser Xaa Xaa Phe Asn
        35

<210> SEQ ID NO 148
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 148

Met Val Lys Val Ile Gly Arg Arg Ser Leu Gly Val Gln Arg Ile Phe
 1               5                  10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 149
<211> LENGTH: 39
<212> TYPE: PRT
<213> ORGANISM: Aphanothece halophytica
```

```
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 149

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
            35

<210> SEQ ID NO 150
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 150

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn
            35

<210> SEQ ID NO 151
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 151

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
            35
```

<210> SEQ ID NO 152
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 152

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
        35

<210> SEQ ID NO 153
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 153

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
        35

<210> SEQ ID NO 154
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 154

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu

Ile Ala Ser Xaa Xaa Phe Asn
        35

<210> SEQ ID NO 155
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 155

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 156
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 156

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 157
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 157

-continued

```
Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35
```

<210> SEQ ID NO 158
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 158

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35
```

<210> SEQ ID NO 159
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 159

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35
```

<210> SEQ ID NO 160
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe, -continued Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 160

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 161
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 161

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
        35

<210> SEQ ID NO 162
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 162

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
        35

<210> SEQ ID NO 163
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)

```
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 163

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn
            35

<210> SEQ ID NO 164
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 164

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn
            35

<210> SEQ ID NO 165
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 165

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
            35

<210> SEQ ID NO 166
<211> LENGTH: 39
<212> TYPE: PRT
<213> ORGANISM: Synechocystis PCC6803
<220> FEATURE:
```

```
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 166

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 167
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 167

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 168
<211> LENGTH: 39
<212> TYPE: PRT
<213> ORGANISM: Aphanizomenon ovalisporum
<220> FEATURE:
<221> NAME/KEY: MISC_FEATURE
<222> LOCATION

```
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 169

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
        35

<210> SEQ ID NO 170
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 170

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
        35

<210> SEQ ID NO 171
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 171

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
        35

<210> SEQ ID NO 172
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe
```

-continued

```
<400> SEQUENCE: 172

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
                20                  25                  30

Ile Ala Ser Xaa Xaa Phe Asn
            35

<210> SEQ ID NO 173
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 173

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
                20                  25                  30

Ile Ala Ser Xaa Xaa Phe Asn
            35

<210> SEQ ID NO 174
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 174

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Xaa Xaa Phe Asn
            35

<210> SEQ ID NO 175
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 175

Met Val Lys Ile Ile Gly Arg Gln Ser Leu Gly Arg Lys Pro Val Tyr
1               5                   10                  15
```

```
Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 176
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 176

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 177
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 177

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 178
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 178

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30
```

Val Ala Ser Xaa Xaa Phe Asn
            35

<210> SEQ ID NO 179
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 179

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Xaa Xaa Phe Asn
            35

<210> SEQ ID NO 180
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 180

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
                20                  25                  30

Ala Ala Xaa Xaa Phe Asn
            35

<210> SEQ ID NO 181
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 181

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa Xaa Phe Asn
            35

```
<210> SEQ ID NO 182
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 182

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 183
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 183

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn
        35

<210> SEQ ID NO 184
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 184

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn
        35

<210> SEQ ID NO 185
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 185

Met Val Lys Ile Ile Lys Arg Gln Ser Leu Gly Arg Gln Asn Val Tyr
```

-continued

```
                1               5                  10                  15
Asp Val Cys Val Glu Thr Asp His Asn Phe Val Leu Ala Asn Gly Cys
                20                  25                  30
Val Ala Ser Xaa Ala Phe Asn
        35

<210> SEQ ID NO 186
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 186

Met Val Lys Ile Thr Ala Arg Lys Phe Val Gly Arg Glu Asn Val Tyr
1               5                  10                  15
Asp Ile Gly Val Glu His His His Asn Phe Ala Ile Lys Asn Gly Leu
                20                  25                  30
Ile Ala Ser Xaa Ala Phe Asn
        35

<210> SEQ ID NO 187
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 187

Met Ile Lys Ile Ala Ser Arg Lys Phe Leu Gly Val Glu Asn Val Tyr
1               5                  10                  15
Asp Ile Gly Val Arg Arg Asp His Asn Phe Phe Ile Lys Asn Gly Leu
                20                  25                  30
Ile Ala Ser Xaa Ala Phe Asn
        35

<210> SEQ ID NO 188
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 188

Met Ile Lys Ile Ala Ser Arg Lys Phe Leu Gly Val Glu Asn Val Tyr
1               5                  10                  15
Asp Ile Gly Val Gly Arg Asp His Asn Phe Phe Val Lys Asn Gly Leu
                20                  25                  30
Ile Ala Ser Xaa Ala Phe Asn
        35

<210> SEQ ID NO 189
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
```

<223> OTHER INFORMATION: Xaa is any amino acid excluding Asn and/or Gln

<400> SEQUENCE: 189

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Ala Phe Asn
        35

<210> SEQ ID NO 190
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 190

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn
        35

<210> SEQ ID NO 191
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 191

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn
        35

<210> SEQ ID NO 192
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 192

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Ala Phe Asn
        35

<210> SEQ ID NO 193
<211> LENGTH: 39

```
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 193

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Ala Phe Asn
        35

<210> SEQ ID NO 194
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 194

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 195
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 195

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 196
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 196

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn
```

```
<210> SEQ ID NO 197
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 197

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn
        35

<210> SEQ ID NO 198
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 198

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Ala Phe Asn
        35

<210> SEQ ID NO 199
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 199

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Ala Phe Asn
        35

<210> SEQ ID NO 200
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 200

Met Lys Ile Val Gly Arg Arg Leu Val Gly Trp Gln Ala Val Tyr Asp
1               5                   10                  15
```

Ile Gly Leu Ala Gly Asp His Asn Phe Leu Ala Asn Gly Ala Ile
            20                  25                  30

Ala Ala Xaa Ala Phe Asn
        35

<210> SEQ ID NO 201
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 201

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
        35

<210> SEQ ID NO 202
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 202

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 203
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys -continued

<400> SEQUENCE: 203

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 204
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 204

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn
        35

<210> SEQ ID NO 205
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 205

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
        35

<210> SEQ ID NO 206
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,

```
       2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 206

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
        35

<210> SEQ ID NO 207
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 207

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
        35

<210> SEQ ID NO 208
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 208

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn
        35

<210> SEQ ID NO 209
<211> LENGTH: 39
<212> TYPE: PRT
<213> ORGANISM: Cyanothece PCC8801
<220> FEATURE:
```

```
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 209

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 210
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 210

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 211
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 211

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35
```

```
<210> SEQ ID NO 212
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 212

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 213
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 213

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 214
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 214

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30
```

Val Ala Ser Xaa Xaa Phe Asn
          35

<210> SEQ ID NO 215
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 215

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
          35

<210> SEQ ID NO 216
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 216

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
        35

<210> SEQ ID NO 217
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Asn

<400> SEQUENCE: 217

-continued

```
Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn
            35

<210> SEQ ID NO 218
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 218

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 219
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 219

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
            35

<210> SEQ ID NO 220
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
```

```
       2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 220

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 221
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 221

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 222
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 222

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30
```

-continued

Ile Ala Ser Xaa Xaa Phe Asn
         35

<210> SEQ ID NO 223
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 223

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
         35

<210> SEQ ID NO 224
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 224

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
         35

<210> SEQ ID NO 225
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE

```
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 225

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
            35

<210> SEQ ID NO 226
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 226

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn
            35

<210> SEQ ID NO 227
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 227

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
            35
```

```
<210> SEQ ID NO 228
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 228

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 229
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 229

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 230
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
``` such as norleucine, 2-aminobutyric acid, nor-valine,
2-aminopentoic acid, or 2-aminohexaanoic acid

<400> SEQUENCE: 230

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 231
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 231

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 232
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 232

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 233
<211> LENGTH: 39

```
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 233

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
        35

<210> SEQ ID NO 234
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 234

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
        35

<210> SEQ ID NO 235
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
```

-continued

```
<400> SEQUENCE: 235

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn
        35

<210> SEQ ID NO 236
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 236

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 237
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 237

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
        35

<210> SEQ ID NO 238
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
```

```
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 238

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 239
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 239

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 240
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 240

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn
        35

<210> SEQ ID NO 241
<211> LENGTH: 39
<212> TYPE: PRT
```

```
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 241

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
            35

<210> SEQ ID NO 242
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 242

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
            35

<210> SEQ ID NO 243
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 243

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
            35
```

```
<210> SEQ ID NO 244
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 244

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn
        35

<210> SEQ ID NO 245
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 245

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 246
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 246

Met Val Lys Ile Ile Gly Cys Arg Ser Leu Gly Thr Gln Lys Val Tyr
1               5                   10                  15
```

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 247
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 247

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 248
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 248

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 249
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe -continued

```
<400> SEQUENCE: 249

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 250
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 250

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 251
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 251

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
        35

<210> SEQ ID NO 252
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
```

```
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 252

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
        35

<210> SEQ ID NO 253
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 253

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn
        35

<210> SEQ ID NO 254
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 254

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 255
<211> LENGTH: 39
<212> TYPE: PRT
<213> ORGANISM: Nostoc punctiforme
<220> FEATURE:
<221> NAME/KEY: MISC_FEATURE
```

```
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 255

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn
            35

<210> SEQ ID NO 256
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 256

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn
            35

<210> SEQ ID NO 257
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 257

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Ala Phe Asn
            35

<210> SEQ ID NO 258
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 258
```

```
Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Xaa Ala Phe Asn
            35
```

<210> SEQ ID NO 259
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 259

```
Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Ala Phe Asn
            35
```

<210> SEQ ID NO 260
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 260

```
Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Ala Phe Asn
            35
```

<210> SEQ ID NO 261
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 261

```
Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30
```

Val Ala Ser Xaa Ala Phe Asn
                35

<210> SEQ ID NO 262
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 262

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn
                35

<210> SEQ ID NO 263
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 263

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn
                35

<210> SEQ ID NO 264
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 264

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Ala Phe Asn
                35

<210> SEQ ID NO 265
<211> LENGTH: 39
<212> TYPE: PRT

-continued

```
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 265

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Ala Phe Asn
        35

<210> SEQ ID NO 266
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 266

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 267
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 267

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 268
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
```

-continued 2-aminopentoic acid, or 2-aminohexaanoic acid

<400> SEQUENCE: 268

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn
        35

<210> SEQ ID NO 269
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 269

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn
        35

<210> SEQ ID NO 270
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 270

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Ala Phe Asn
        35

<210> SEQ ID NO 271
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 271

Met Val Lys Ile Val Ser Arg Lys Leu Ala Lys Thr Glu Asn Val Tyr
1               5                   10                  15

```
Asp Ile Gly Val Thr Lys Asp His Asn Phe Val Leu Ala Asn Gly Leu
            20                  25                  30

Ile Ala Ser Xaa Ala Phe Asn
        35
```

<210> SEQ ID NO 272
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 272

```
Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Ala Phe Asn
        35
```

<210> SEQ ID NO 273
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 273

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
        35
```

<210> SEQ ID NO 274
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 274

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35
```

<210> SEQ ID NO 275
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 275

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 276
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 276

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Xaa Xaa Phe Asn
        35

<210> SEQ ID NO 277
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 277

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn
        35

<210> SEQ ID NO 278
<211> LENGTH: 39

```
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 278

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
        35

<210> SEQ ID NO 279
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 279

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
        35

<210> SEQ ID NO 280
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 280

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn
        35

<210> SEQ ID NO 281
<211> LENGTH: 39
<212> TYPE: PRT
<213> ORGANISM: Cyanothece PCC8801
<220> FEATURE:
<221> NAME/KEY: MISC_FEATURE
```

-continued

```
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 281

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 282
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 282

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 283
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 283

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 284
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
```

<222> LOCATION: (37)..(37)
<223> OTHER INFORMATION: Xaa is any amino acid excluding Cys

<400> SEQUENCE: 284

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 285
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 285

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 286
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 286

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 287
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 287

```
Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Xaa Xaa Phe Asn
        35
```

<210> SEQ ID NO 288
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 288

```
Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
                20                  25                  30

Ala Ala Xaa Xaa Phe Asn
        35
```

<210> SEQ ID NO 289
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 289

```
Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa Xaa Phe Asn
        35
```

<210> SEQ ID NO 290
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 290

```
Met Lys Ile Val Gly Arg Arg Leu Val Gly Trp Gln Ala Val Tyr Asp
1               5                   10                  15
```

Ile Gly Leu Ala Gly Asp His Asn Phe Leu Leu Ala Asn Gly Ala Ile
            20                  25                  30

Ala Ala Xaa Xaa Phe Asn
        35

<210> SEQ ID NO 291
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 291

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn
        35

<210> SEQ ID NO 292
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 292

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 293
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

```
<400> SEQUENCE: 293

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 294
<211> LENGTH: 39
<212> TYPE: PRT
<213> ORGANISM: Aphanizomenon ovalisporum
<220> FEATURE:
<221> NAME/

```
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 296

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
            35

<210> SEQ ID NO 297
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Ph

```
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 299

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 300
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 300

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 301
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 301

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 302
```

```
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 302

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 303
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 303

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 304
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 304

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30
```

```
Val Ala Ser Xaa Xaa Phe Asn
            35

<210> SEQ ID NO 305
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 305

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
            35

<210> SEQ ID NO 306
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 306

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
        35

<210> SEQ ID NO 307
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 307

Met Val Lys Ile Val Ser Arg Lys Leu Ala Lys Thr Glu Asn Val Tyr
```

```
1               5                   10                  15
Asp Ile Gly Val Thr Lys Asp His Asn Phe Val Leu Ala Asn Gly Leu
                20                  25                  30

Ile Ala Ser Xaa Xaa Phe Asn
            35
```

<210> SEQ ID NO 308
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 308

```
Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
                20                  25                  30

Ala Ala Xaa Xaa Phe Asn
            35
```

<210> SEQ ID NO 309
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 309

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
                20                  25                  30

Ile Ala Ser Xaa Xaa Phe Asn
            35
```

<210> SEQ ID NO 310
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 310

```
Met Val Lys Val Ile Gly Arg Arg Ser Leu Gly Val Gln Arg Ile Phe
1               5                   10                  15
```

-continued

```
Asp Ile Gly Leu Pro Gln Asp His Asn Phe Leu Leu Ala Asn Gly Ala
            20                  25                  30

Ile Ala Ala Xaa Xaa Phe Asn
        35

<210> SEQ ID NO 311
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 311

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn
        35

<210> SEQ ID NO 312
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 312

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn
        35

<210> SEQ ID NO 313
<211> LENGTH: 39
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 313

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30
```

Ile Ala Ser Xaa Xaa Phe Asn
            35

<210> SEQ ID NO 314
<211> LENGTH: 39
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 314

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn
            35

<210> SEQ ID NO 315
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 315

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn
            35

<210> SEQ ID NO 316
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 316

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn
            35

-continued

```
<210> SEQ ID NO 317
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 317

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn
        35

<210> SEQ ID NO 318
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 318

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn
        35

<210> SEQ ID NO 319
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 319

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn
        35

<210> SEQ ID NO 320
<211> LENGTH: 39
<212> TYPE: PRT
<213> ORGANISM: Microcoleus chthonoplastes
```

-continued

```
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 320

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 321
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 321

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn
        35

<210> SEQ ID NO 322
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 322

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn
        35

<210> SEQ ID NO 323
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
```

```
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 323

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn
            35

<210> SEQ ID NO 324
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 324

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn
            35

<210> SEQ ID NO 325
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 325

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn
            35

<210> SEQ ID NO 326
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
```

```
<400> SEQUENCE: 326

Met Lys Ile Val Gly Arg Arg Leu Val Gly Trp Gln Ala Val Tyr Asp
1               5                   10                  15

Ile Gly Leu Ala Gly Asp His Asn Phe Leu Ala Asn Gly Ala Ile
            20                  25                  30

Ala Ala Xaa Xaa Phe Asn
        35

<210> SEQ ID NO 327
<211> LENGTH: 39
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 327

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn
        35

<210> SEQ ID NO 328
<211> LENGTH: 39
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 328

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn
        35

<210> SEQ ID NO 329
<211> LENGTH: 39
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 329

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Ala Phe Asn
        35

<210> SEQ ID NO 330
<211> LENGTH: 39
<212> TYPE: PRT
```

-continued

```
<213> ORGANISM: Aphanizomenon ovalisporum
<220> FEATURE:
<221> NAME/KEY: M

<210> SEQ ID NO 334
<211> LENGTH: 39
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 334

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn
        35

<210> SEQ ID NO 335
<211> LENGTH: 39
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 335

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn
        35

<210> SEQ ID NO 336
<211> LENGTH: 39
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 336

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Ala Phe Asn
        35

<210> SEQ ID NO 337
<211> LENGTH: 39
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 337

Met Val Lys Ile Ile Gly Arg Gln Ser Leu Gly Arg Lys Pro Val Tyr
1               5                   10                  15

-continued

Asp Ile Gly Val Glu Lys Asp His Asn Phe Leu Leu Gly Asn Gly Leu
            20                  25                  30

Ile Ala Ser Xaa Ala Phe Asn
        35

<210> SEQ ID NO 338
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 338

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 339
<211> LENGTH: 39
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 339

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn
        35

<210> SEQ ID NO 340
<211> LENGTH: 39
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 340

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn
        35

<210> SEQ ID NO 341
<211> LENGTH: 39
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe -continued

```
<400> SEQUENCE: 341

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn
            35

<210> SEQ ID NO 342
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe

<400> SEQUENCE: 342

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Ala Phe Asn
            35

<210> SEQ ID NO 343
<211> LENGTH: 39
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 343

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Ala Phe Asn
            35

<210> SEQ ID NO 344
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe

<400> SEQUENCE: 344

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Ala Phe Asn
            35

<210> SEQ ID NO 345
<211> LENGTH: 39
<212> TYPE: PRT
<213> ORGANISM: Nostoc punctiforme
```

```
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 345

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn
        35

<210> SEQ ID NO 346
<211> LENGTH: 39
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 346

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Xaa Phe Asn
        35

<210> SEQ ID NO 347
<211> LENGTH: 39
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 347

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Xaa Phe Asn
        35

<210> SEQ ID NO 348
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 348

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Ala Xaa Phe Asn
        35
```

```
<210> SEQ ID NO 349
<211> LENGTH: 39
<212> TYPE: PRT
<213> ORGANISM: Anabaena PCC7120
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 349

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala Xaa Phe Asn
        35

<210> SEQ ID NO 350
<211> LENGTH: 39
<212> TYPE: PRT
<213> ORGANISM: Anabaena variabilis
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 350

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala Xaa Phe Asn
        35

<210> SEQ ID NO 351
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 351

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Xaa Phe Asn
        35

<210> SEQ ID NO 352
<211> LENGTH: 39
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 352

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
```

-continued

```
                    20                  25                  30

Ile Ala Ser Ala Xaa Phe Asn
        35

<210> SEQ ID NO 353
<211> LENGTH: 39
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 353

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
                20                  25                  30

Ile Ala Ser Ala Xaa Phe Asn
        35

<210> SEQ ID NO 354
<211> LENGTH: 39
<212> TYPE: PRT
<213> ORGANISM: Crocosphaera watsonii
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 354

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Ala Xaa Phe Asn
        35

<210> SEQ ID NO 355
<211> LENGTH: 39
<212> TYPE: PRT
<213> ORGANISM: Microcystis aeruginosa
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 355

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
                20                  25                  30

Ile Ala Ser Ala Xaa Phe Asn
        35

<210> SEQ ID NO 356
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 356
```

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
            35

<210> SEQ ID NO 357
<211> LENGTH: 39
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 357

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
            35

<210> SEQ ID NO 358
<211> LENGTH: 39
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 358

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Xaa Phe Asn
            35

<210> SEQ ID NO 359
<211> LENGTH: 39
<212> TYPE: PRT
<213> ORGANISM: Synechococcus PCC7002
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 359

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Xaa Phe Asn
            35

<210> SEQ ID NO 360
<211> LENGTH: 38
<212> TYPE: PRT
<213> ORGANISM: Thermosynechococcus elongatus
<220> FEATURE:

```
<221> NAME/KEY: MISC_FEATURE
<222> LOCATION: (36)..(36)
<223> OTHER INFORMATION: Xaa is any amino acid excluding Cys

<400> SEQUENCE: 360

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Xaa Phe Asn
            35

<210> SEQ ID NO 361
<211> LENGTH: 39
<212> TYPE: PRT
<213> ORGANISM: Trichodesmium erythraeum
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 361

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Xaa Phe Asn
            35

<210> SEQ ID NO 362
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 362

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Ala Xaa Phe Asn
            35

<210> SEQ ID NO 363
<211> LENGTH: 39
<212> TYPE: PRT
<213> ORGANISM: Nostoc punctiforme
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 363

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn
```

<210> SEQ ID NO 364
<211> LENGTH: 39
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 364

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Xaa Phe Asn
        35

<210> SEQ ID NO 365
<211> LENGTH: 39
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 365

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Xaa Phe Asn
        35

<210> SEQ ID NO 366
<211> LENGTH: 39
<212> TYPE: PRT
<213> ORGANISM: Aphanizomenon ovalisporum
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 366

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Ala Xaa Phe Asn
        35

<210> SEQ ID NO 367
<211> LENGTH: 39
<212> TYPE: PRT
<213> ORGANISM: Anabaena PCC7120

```
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 367

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala Xaa Phe Asn
        35

<210> SEQ ID NO 368
<211> LENGTH: 39
<212> TYPE: PRT
<213> ORGANISM: Anabaena variabilis
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 368

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala Xaa Phe Asn
        35

<210> SEQ ID NO 369
<211> LENGTH: 39
<212> TYPE: PRT
<213> ORGANISM: Cylindrospermopsis raciborskii
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 369

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Xaa Phe Asn
        35

<210> SEQ ID NO 370
<211> LENGTH: 39
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
```

```
<400> SEQUENCE: 370

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Xaa Phe Asn
            35

<210> SEQ ID NO 371
<211> LENGTH: 39
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 371

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Xaa Phe Asn
            35

<210> SEQ ID NO 372
<211> LENGTH: 39
<212> TYPE: PRT
<213> ORGANISM: Crocosphaera watsonii
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 372

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala Xaa Phe Asn
            35

<210> SEQ ID NO 373
<211> LENGTH: 39
<212> TYPE: PRT
<213> ORGANISM: Microcystis aeruginosa
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 373

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
```

Ile Ala Ser Ala Xaa Phe Asn
        35

<210> SEQ ID NO 374
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 374

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
        35

<210> SEQ ID NO 375
<211> LENGTH: 39
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 375

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
        35

<210> SEQ ID NO 376
<211> LENGTH: 39
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 376

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Xaa Phe Asn
        35

<210> SEQ ID NO 377

```
<211> LENGTH: 39
<212> TYPE: PRT
<213> ORGANISM: Synechococcus PCC7002
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 377

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Xaa Phe Asn
        35

<210> SEQ ID NO 378
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 378

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Xaa Phe Asn
        35

<210> SEQ ID NO 379
<211> LENGTH: 39
<212> TYPE: PRT
<213> ORGANISM: Trichodesmium erythraeum
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 379

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Xaa Phe Asn
        35

<210> SEQ ID NO 380
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
```

Tyr, Gly or Trp or can be a unnatural aliphatic amino acid residue
such as norleucine, 2-aminobutyric acid, nor-valine,
2-aminopentoic acid, or 2-aminohexaanoic acid

<400> SEQUENCE: 380

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Ala Xaa Phe Asn
        35

<210> SEQ ID NO 381
<211> LENGTH: 39
<212> TYPE: PRT
<213> ORGANISM: Nostoc punctiforme
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 381

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn
        35

<210> SEQ ID NO 382
<211> LENGTH: 39
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 382

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Xaa Phe Asn
        35

<210> SEQ ID NO 383
<211> LENGTH: 39
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 383

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Xaa Phe Asn
        35

```
<210> SEQ ID NO 384
<211> LENGTH: 39
<212> TYPE: PRT
<213> ORGANISM: Aphanizomenon ovalisporum
<220

Val Ala Ser Ala Xaa Phe Asn
        35

<210> SEQ ID NO 388
<211> LENGTH: 39
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 388

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Xaa Phe Asn
        35

<210> SEQ ID NO 389
<211> LENGTH: 39
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 389

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Xaa Phe Asn
        35

<210> SEQ ID NO 390
<211> LENGTH: 39
<212> TYPE: PRT
<213> ORGANISM: Crocosphaera watsonii
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 390

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala Xaa Phe Asn
        35

<210> SEQ ID NO 391
<211> LENGTH: 39
<212> TYPE: PRT
<213> ORGANISM: Microcystis aeruginosa
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 391

```
Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala Xaa Phe Asn
        35

<210> SEQ ID NO 392
<211> LENGTH: 39
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 392

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
        35

<210> SEQ ID NO 393
<211> LENGTH: 39
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 393

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn
        35

<210> SEQ ID NO 394
<211> LENGTH: 39
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 394

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Xaa Phe Asn
        35

<210> SEQ ID NO 395
<211> LENGTH: 39
<212> TYPE: PRT
<213> ORGANISM: Synechococcus PCC7002
<220> FEATURE:
<221> NAME/KEY: MISC_FEATURE
```

-continued

```
<222> LOCATION: (37)..(37)
<223> OTHER INFORMATION: Xaa is Ala, Ile, Val, Leu, Tyr, Gly or Phe

<400> SEQUENCE: 395

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Xaa Phe Asn
        35

<210> SEQ ID NO 396
<211> LENGTH: 38
<212> TYPE: PRT
<213> ORGANISM: Thermosynechococcus elongatus
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 396

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Xaa Phe Asn
        35

<210> SEQ ID NO 397
<211> LENGTH: 39
<212> TYPE: PRT
<213> ORGANISM: Trichodesmium erythraeum
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 397

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Xaa Phe Asn
        35

<210> SEQ ID NO 398
<211> LENGTH: 38
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 398

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Ala Xaa Phe Asn
        35

<210> SEQ ID NO 399
```

```
<211> LENGTH: 39
<212> TYPE: PRT
<213> ORGANISM: Nostoc punctiforme

<400> SEQUENCE: 399

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Ala Phe Asn
        35

<210> SEQ ID NO 400
<211> LENGTH: 39
<212> TYPE: PRT
<213> ORGANISM: Synechocystis PCC6803

<400> SEQUENCE: 400

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Ala Phe Asn
        35

<210> SEQ ID NO 401
<211> LENGTH: 39
<212> TYPE: PRT
<213> ORGANISM: Aphanothece halophytica

<400> SEQUENCE: 401

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Ala Phe Asn
        35

<210> SEQ ID NO 402
<211> LENGTH: 39
<212> TYPE: PRT
<213> ORGANISM: Aphanizomenon ovalisporum

<400> SEQUENCE: 402

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Ala Ala Phe Asn
        35

<210> SEQ ID NO 403
<211> LENGTH: 39
<212> TYPE: PRT
<213> ORGANISM: Anabaena PCC7120

<400> SEQUENCE: 403

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30
```

Ile Ala Ser Ala Ala Phe Asn
        35

<210> SEQ ID NO 404
<211> LENGTH: 39
<212> TYPE: PRT
<213> ORGANISM: Anabaena variabilis

<400> SEQUENCE: 404

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala Ala Phe Asn
        35

<210> SEQ ID NO 405
<211> LENGTH: 39
<212> TYPE: PRT
<213> ORGANISM: Cylindrospermopsis raciborskii

<400> SEQUENCE: 405

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Ala Phe Asn
        35

<210> SEQ ID NO 406
<211> LENGTH: 39
<212> TYPE: PRT
<213> ORGANISM: Cyanothece CCY0110

<400> SEQUENCE: 406

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Ala Phe Asn
        35

<210> SEQ ID NO 407
<211> LENGTH: 39
<212> TYPE: PRT
<213> ORGANISM: Cyanothece PCC8801

<400> SEQUENCE: 407

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Ala Phe Asn
        35

<210> SEQ ID NO 408
<211> LENGTH: 39
<212> TYPE: PRT
<213> ORGANISM: Crocosphaera watsonii

<400> SEQUENCE: 408

```
Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Ala Ala Phe Asn
                35
```

<210> SEQ ID NO 409
<211> LENGTH: 39
<212> TYPE: PRT
<213> ORGANISM: Microcystis aeruginosa

<400> SEQUENCE: 409

```
Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
                20                  25                  30

Ile Ala Ser Ala Ala Phe Asn
                35
```

<210> SEQ ID NO 410
<211> LENGTH: 39
<212> TYPE: PRT
<213> ORGANISM: Microcoleus chthonoplastes

<400> SEQUENCE: 410

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Ala Ser Ala Ala Phe Asn
                35
```

<210> SEQ ID NO 411
<211> LENGTH: 39
<212> TYPE: PRT
<213> ORGANISM: Oscillatoria limnetica

<400> SEQUENCE: 411

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Ala Ser Ala Ala Phe Asn
                35
```

<210> SEQ ID NO 412
<211> LENGTH: 39
<212> TYPE: PRT
<213> ORGANISM: Synechococcus elongatus

<400> SEQUENCE: 412

```
Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
                20                  25                  30

Val Ala Ser Ala Ala Phe Asn
                35
```

-continued

```
<210> SEQ ID NO 413
<211> LENGTH: 39
<212> TYPE: PRT
<213> ORGANISM: Synechococcus PCC7002

<400> SEQUENCE: 413

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Ala Phe Asn
        35

<210> SEQ ID NO 414
<211> LENGTH: 38
<212> TYPE: PRT
<213> ORGANISM: Thermosynechococcus elongatus

<400> SEQUENCE: 414

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Ala Phe Asn
        35

<210> SEQ ID NO 415
<211> LENGTH: 39
<212> TYPE: PRT
<213> ORGANISM: Trichodesmium erythraeum

<400> SEQUENCE: 415

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Ala Phe Asn
        35

<210> SEQ ID NO 416
<211> LENGTH: 38
<212> TYPE: PRT
<213> ORGANISM: Thermosynechococcus vulcanus

<400> SEQUENCE: 416

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Ala Ala Phe Asn
        35

<210> SEQ ID NO 417
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
```

<223> OTHER INFORMATION: Xaa is any amino acid excluding Cys

<400> SEQUENCE: 417

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 418
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 418

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 419
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 419

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 420
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 420

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
        35                  40

<210> SEQ ID NO 421
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 421

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 422
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 422

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 423
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 423

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu

```
                        20                  25                  30

Val Ala Ser Xaa Xaa Phe Asn Ser Gly Gly Cys
            35                  40

<210> SEQ ID NO 424
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 424

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
                20                  25                  30

Ile Ala Ser Xaa Xaa Phe Asn Ser Gly Gly Cys
            35                  40

<210> SEQ ID NO 425
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 425

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
                20                  25                  30

Ile Ala Ser Xaa Xaa Phe Asn Ser Gly Gly Cys
            35                  40

<210> SEQ ID NO 426
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 426

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Xaa Xaa Phe Asn Ser Gly Gly Cys
            35                  40
```

<210> SEQ ID NO 427
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 427

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 428
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 428

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 429
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 429

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 430
<211> LENGTH: 43

<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 430

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
                20                  25                  30

Val Ala Ser Xaa Xaa Phe Asn Ser Gly Gly Cys
            35                  40

<210> SEQ ID NO 431
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 431

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Xaa Xaa Phe Asn Ser Gly Gly Cys
            35                  40

<210> SEQ ID NO 432
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 432

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
                20                  25                  30

Ala Ala Xaa Xaa Phe Asn Ser Gly Gly Cys
        35                  40

<210> SEQ ID NO 433
<211> LENGTH: 43
<212> TYPE: PRT
<213> ORGANISM: Trichodesmium erythraeum
<220> FEATURE:
<221> NAME/KEY: MISC_FEATURE -continued

```
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is any amino acid excluding Asn

<400> SEQUENCE: 433

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 434
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 434

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 435
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 435

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 436
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
```

<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 436

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 437
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 437

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 438
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 438

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
        35                  40

<210> SEQ ID NO 439
<211> LENGTH: 43

```
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 439

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 440
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 440

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 441
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 441

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
```

35                  40

<210> SEQ ID NO 442
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 442

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 443
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 443

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 444
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 444

Met Val Lys Ile Ile Gly Cys Arg Ser Leu Gly Thr Gln Lys Val Tyr
1               5                   10                  15

```
Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
            35                  40

<210> SEQ ID NO 445
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 445

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
            35                  40

<210> SEQ ID NO 446
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 446

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
            35                  40

<210> SEQ ID NO 447
<211> LENGTH: 43
<212> TYPE: PRT
<213> ORGANISM: Oscillatoria lim

```
<400> SEQUENCE: 447

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 448
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 448

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
        35                  40

<210> SEQ ID NO 449
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 449

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
        35                  40

<210> SEQ ID NO 450
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
```

```
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 450

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn Ser Gly Gly Cys
        35                  40

<210> SEQ ID NO 451
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 451

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 452
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 452

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 453
<211> LENGTH: 43
<212> TYPE: PRT
<213> ORGANISM: Nostoc punctiforme
<220> FEATURE:
```

```
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 453

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 454
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 454

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 455
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 455

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 456
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
```

```
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 456

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Xaa Xaa Phe Asn Ser Gly Gly Cys
            35                  40

<210> SEQ ID NO 457
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 457

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
            35                  40

<210> SEQ ID NO 458
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 458

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
            35                  40

<210> SEQ ID NO 459
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe
```

```
<400> SEQUENCE: 459

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
            35                  40

<210> SEQ ID NO 460
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 460

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
            35                  40

<210> SEQ ID NO 461
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 461

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
            35                  40

<210> SEQ ID NO 462
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 462

Met Val Lys Ile Ile Gly Cys Arg Ser Leu Gly Thr Gln Lys Val Tyr
1               5                   10                  15
```

```
Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 463
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 463

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 464
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 464

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 465
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 465

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30
```

```
Ile Ala Ser Xaa Xaa Phe Asn Ser Gly Gly Cys
            35                  40
```

<210> SEQ ID NO 466
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 466

```
Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
            35                  40
```

<210> SEQ ID NO 467
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 467

```
Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
            35                  40
```

<210> SEQ ID NO 468
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 468

```
Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn Ser Gly Gly Cys
            35                  40
```

```
<210> SEQ ID NO 469
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 469

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
            35                  40

<210> SEQ ID NO 470
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 470

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
            35                  40

<210> SEQ ID NO 471
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 471

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn Ser Gly Gly Cys
            35                  40

<210> SEQ ID NO 472
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is any amino acid excluding Asn and/or Gln
```

-continued

<400> SEQUENCE: 472

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn Ser Gly Gly Cys
        35                  40

<210> SEQ ID NO 473
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 473

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Ala Phe Asn Ser Gly Gly Cys
        35                  40

<210> SEQ ID NO 474
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 474

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Ala Phe Asn Ser Gly Gly Cys
        35                  40

<210> SEQ ID NO 475
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 475

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Ala Phe Asn Ser Gly Gly Cys
        35                  40

<210> SEQ ID NO 476
<211> LENGTH: 43
<212> TYPE: PRT

```
<213> ORGANISM: Anabaena variabilis
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 476

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Ala Phe Asn Ser Gly Gly Cys
        35                  40

<210> SEQ ID NO 477
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 477

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Ala Phe Asn Ser Gly Gly Cys
        35                  40

<210> SEQ ID NO 478
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 478

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn Ser Gly Gly Cys
        35                  40

<210> SEQ ID NO 479
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 479

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn Ser Gly Gly Cys
        35                  40
```

<210> SEQ ID NO 480
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 480

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Ala Phe Asn Ser Gly Gly Cys
        35                  40

<210> SEQ ID NO 481
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 481

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Ala Phe Asn Ser Gly Gly Cys
        35                  40

<210> SEQ ID NO 482
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 482

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn Ser Gly Gly Cys
        35                  40

<210> SEQ ID NO 483
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 483

Met Val Lys Ile Val Arg Arg Gln Ser Leu Gly Val Gln Asn Val Tyr
1               5                   10                  15

-continued

Asp Ile Gly Val Glu Lys Asp His Asn Phe Cys Leu Ala Ser Gly Glu
            20                  25                  30

Ile Ala Ser Xaa Ala Phe Asn Ser Gly Gly Cys
        35                  40

<210> SEQ ID NO 484
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 484

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn Ser Gly Gly Cys
        35                  40

<210> SEQ ID NO 485
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is any amino acid excluding Asn and/or Gln

<400> SEQUENCE: 485

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn Ser Gly Gly Cys
        35                  40

<210> SEQ ID NO 486
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 486

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Ala Phe Asn Ser Gly Gly Cys
        35                  40

<210> SEQ ID NO 487
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is any amino acid excluding Asn and/or Gln -continued

```
<400> SEQUENCE: 487

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa Ala Phe Asn Ser Gly Gly Cys
            35                  40

<210> SEQ ID NO 488
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 488

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
                20                  25                  30

Ala Ala Xaa Ala Phe Asn Ser Gly Gly Cys
            35                  40

<210> SEQ ID NO 489
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 489

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
                20                  25                  30

Ile Ala Ser Xaa Xaa Phe Asn Ser Gly Gly Cys
            35                  40

<210> SEQ ID NO 490
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 490
```

-continued

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40
```

<210> SEQ ID NO 491
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 491

```
Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40
```

<210> SEQ ID NO 492
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 492

```
Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
        35                  40
```

<210> SEQ ID NO 493
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE

```
<222> LOCATION: (37)..(37)
<223> OTHER INFORMATION: Xaa is any amino acid excluding Cys

<400> SEQUENCE: 493

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 494
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 494

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 495
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 495

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
        35                  40

<210> SEQ ID NO 496
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
```

```
      Tyr, Gly or Trp or can be a unnatural aliphatic amino acid
      residue such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 496

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 497
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 497

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 498
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 498

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 499
<211> LENGTH: 43
<212> TYPE: PRT
```

```
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 499

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 500
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 500

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 501
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 501

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40
```

<210> SEQ ID NO 502
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 502

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
        35                  40

<210> SEQ ID NO 503
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 503

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
        35                  40

<210> SEQ ID NO 504
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 504

Met Lys Ile Val Gly Arg Arg Leu Met Gly Trp Gln Ala Val Tyr Asp
1               5                   10                  15

```
Ile Gly Leu Ala Ala Asp His Asn Phe Val Leu Ala Asn Gly Ala Ile
            20                  25                  30

Ala Ala Xaa Xaa Phe Asn Ser Gly Gly Cys
        35                  40

<210> SEQ ID NO 505
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is any amino acid excluding Asn

<400> SEQUENCE: 505

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 506
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 506

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 507
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
``` such as norleucine, 2-aminobutyric acid, nor-valine,
2-aminopentoic acid, or 2-aminohexaanoic acid

<400> SEQUENCE: 507

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 508
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 508

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 509
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 509

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 510
<211> LENGTH: 43

<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Tr -continued

```
<400> SEQUENCE: 512

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 513
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 513

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
        35                  40

<210> SEQ ID NO 514
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 514

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 515
<211> LENGTH: 43
<212> TYPE: PRT
<213> ORGANISM: Cyanothece PCC8801
<220> FEATURE:
```

```
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 515

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 516
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 516

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 517
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 517

Met Val Lys Ile Ile Gly Arg Gln Ser Leu Gly Arg Lys Pro Val Tyr
```

-continued

```
                1               5                  10                 15
Asp Ile Gly Val Glu Lys Asp His Asn Phe Leu Leu Gly Asn Gly Leu
                20                  25                 30
Ile Ala Ser Xaa Xaa Phe Asn Ser Gly Gly Cys
        35                  40

<210> SEQ ID NO 518
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 518

Met Val Lys Ile Val Arg Arg Gln Ser Leu Gly Val Gln Asn Val Tyr
1               5                  10                 15
Asp Ile Gly Val Glu Lys Asp His Asn Phe Cys Leu Ala Ser Gly Glu
                20                  25                 30
Ile Ala Ser Xaa Xaa Phe Asn Ser Gly Gly Cys
        35                  40

<210> SEQ ID NO 519
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 519

Met Val Lys Ile Val Arg Arg Gln Ser Leu Gly Val Gln Asn Val Tyr
1               5                  10                 15
Asp Ile Gly Val Glu Lys Asp His Asn Phe Cys Leu Ala Ser Gly Glu
                20                  25                 30
Ile Ala Ser Xaa Xaa Phe Asn Ser Gly Gly Cys
        35                  40

<210> SEQ ID NO 520
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
```

```
       Tyr, Gly or Trp or can be a unnatural aliphatic amino acid residue
       such as norleucine, 2-aminobutyric acid, nor-valine,
       2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
       Tyr, Gly or Trp or can be a unnatural aliphatic amino acid residue
       such as norleucine, 2-aminobutyric acid, nor-valine,
       2-aminopentoic acid, or 2-aminohexaanoic acid

<400> SEQUENCE: 520

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
        35                  40

<210> SEQ ID NO 521
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
       Tyr, Gly or Trp or can be a unnatural aliphatic amino acid residue
       such as norleucine, 2-aminobutyric acid, nor-valine,
       2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
       Tyr, Gly or Trp or can be a unnatural aliphatic amino acid residue
       such as norleucine, 2-aminobutyric acid, nor-valine,
       2-aminopentoic acid, or 2-aminohexaanoic acid

<400> SEQUENCE: 521

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
        35                  40

<210> SEQ ID NO 522
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
       Tyr, Gly or Trp or can be a unnatural aliphatic amino acid residue
       such as norleucine, 2-aminobutyric acid, nor-valine,
       2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
       Tyr, Gly or Trp or can be a unnatural aliphatic amino acid residue
       such as norleucine, 2-aminobutyric acid, nor-valine,
       2-aminopentoic acid, or 2-aminohexaanoic acid

<400> SEQUENCE: 522

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
```

```
                20                  25                  30
Ala Ala Xaa Xaa Phe Asn Ser Gly Gly Cys
            35                  40

<210> SEQ ID NO 523
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 523

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Xaa Xaa Phe Asn Ser Gly Gly Cys
            35                  40

<210> SEQ ID NO 524
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 524

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
                20                  25                  30

Ala Ala Xaa Xaa Phe Asn Ser Gly Gly Cys
            35                  40

<210> SEQ ID NO 525
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
```

```
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 525

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 526
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 526

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 527
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 527

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 528
<211> LENGTH: 43
<212> TYPE: PRT
<213> ORGANISM: Aphanizomenon ovalisporum
<220> FEATURE:
<221> NAME/KEY: MISC_FEATURE
```

```
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 528

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
        35                  40

<210> SEQ ID NO 529
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 529

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 530
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 530

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 531
```

```
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 531

Met Val Lys Ile Val Ser Arg Arg Tyr Leu Gly Lys Ala Asp Val Tyr
1               5                   10                  15

Asp Ile Gly Val Ala Lys Asp His As

```
Ile Ala Ser Xaa Xaa Phe Asn Ser Gly Gly Cys
        35                  40

<210> SEQ ID NO 534
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 534

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 535
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 535

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 536
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 536

Met Val Lys Ile Val Arg Arg Gln Ser Leu Gly Val Gln Asn Val Tyr
```

```
                1               5                  10                  15
Asp Ile Gly Val Glu Lys Asp His Asn Phe Cys Leu Ala Ser Gly Glu
                    20                  25                  30

Ile Ala Ser Xaa Xaa Phe Asn Ser Gly Gly Cys
            35                  40
```

<210> SEQ ID NO 537
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 537

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                    20                  25                  30

Ile Ala Ser Xaa Xaa Phe Asn Ser Gly Gly Cys
            35                  40
```

<210> SEQ ID NO 538
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 538

```
Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
                    20                  25                  30

Val Ala Ser Xaa Xaa Phe Asn Ser Gly Gly Cys
            35                  40
```

<210> SEQ ID NO 539
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid
<220> FEATURE:
<221> NAME/KEY: MISC_FEATURE
<222> LOCATION: (37)..(37)

<223> OTHER INFORMATION: Xaa is Ala, Ile, Val, Leu, Tyr, Gly or Phe

<400> SEQUENCE: 539

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
        35                  40

<210> SEQ ID NO 540
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 540

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn Ser Gly Gly Cys
        35                  40

<210> SEQ ID NO 541
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 541

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 542
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue such as norleucine, 2-aminobutyric acid, nor-valine,
2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 542

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 543
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 543

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn Ser Gly Gly Cys
        35                  40

<210> SEQ ID NO 544
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 544

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn Ser Gly Gly Cys
        35                  40

<210> SEQ ID NO 545
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 545

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Ala Phe Asn Ser Gly Gly Cys
        35                  40

<210> SEQ ID NO 546
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 546

Met Val Lys Ile Thr Ala Arg Lys Phe Val Gly Arg Glu Asn Val Tyr
1 5 10 15

Asp Ile Gly Val Glu His His His Asn Phe Ala Ile Lys Asn Gly Leu
20 25 30

Ile Ala Ser Xaa Ala Phe Asn Ser Gly Gly Cys
35 40

<210> SEQ ID NO 547
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 547

Met Ile Lys Ile Ala Ser Arg Lys Phe Leu Gly Val Glu Asn Val Tyr
1 5 10 15

Asp Ile Gly Val Arg Arg Asp His Asn Phe Phe Ile Lys Asn Gly Leu
20 25 30

Ile Ala Ser Xaa Ala Phe Asn Ser Gly Gly Cys
35 40

<210> SEQ ID NO 548
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe, Tyr, Gly or Trp or can be a unnatural aliphatic amino acid residue such as norleucine, 2-aminobutyric acid, nor-valine, 2-aminopentoic acid, or 2-aminohexaanoic acid

<400> SEQUENCE: 548

Met Ile Lys Ile Ala Ser Arg Lys Phe Leu Gly Val Glu Asn Val Tyr
1 5 10 15

Asp Ile Gly Val Gly Arg Asp His Asn Phe Phe Val Lys Asn Gly Leu
20 25 30

Ile Ala Ser Xaa Ala Phe Asn Ser Gly Gly Cys
        35                  40

<210> SEQ ID NO 549
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 549

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Ala Phe Asn Ser Gly Gly Cys
        35                  40

<210> SEQ ID NO 550
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 550

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn Ser Gly Gly Cys
        35                  40

<210> SEQ ID NO 551
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 551

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn Ser Gly Gly Cys
        35                  40

<210> SEQ ID NO 552
<211> LENGTH: 43

```
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 552

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Ala Phe Asn Ser Gly Gly Cys
        35                  40

<210> SEQ ID NO 553
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 553

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Ala Phe Asn Ser Gly Gly Cys
        35                  40

<210> SEQ ID NO 554
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 554

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn Ser Gly Gly Cys
        35                  40

<210> SEQ ID NO 555
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
``` such as norleucine, 2-aminobutyric acid, nor-valine,
2-aminopentoic acid, or 2-aminohexaanoic acid

<400> SEQUENCE: 555

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Ala Phe Asn Ser Gly Gly Cys
        35                  40

<210> SEQ ID NO 556
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 556

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn Ser Gly Gly Cys
        35                  40

<210> SEQ ID NO 557
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 557

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn Ser Gly Gly Cys
        35                  40

<210> SEQ ID NO 558
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 558

Met Lys Ile Val Gly Arg Arg Leu Met Gly Trp Gln Ala Val Tyr Asp
1               5                   10                  15

```
Ile Gly Leu Ala Ala Asp His Asn Phe Val Leu Ala Asn Gly Ala Ile
            20                  25                  30

Ala Ala Xaa Ala Phe Asn Ser Gly Gly Cys
        35                  40
```

<210> SEQ ID NO 559
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 559

```
Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Ala Phe Asn Ser Gly Gly Cys
        35                  40
```

<210> SEQ ID NO 560
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 560

```
Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Ala Phe Asn Ser Gly Gly Cys
        35                  40
```

<210> SEQ ID NO 561
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 561

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40
```

<210> SEQ ID NO 562
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 562

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 563
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 563

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 564
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 564

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
        35                  40

<210> SEQ ID NO 565
<211> LENGTH: 43

```
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 565

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 566
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 566

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 567
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 567

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
        35                  40

<210> SEQ ID NO 568
<211> LENGTH: 43
<212> TYPE: PRT
<213> ORGANISM: Cyanothece CCY0110
<220> FEATURE:
<221> NAME/KEY: MISC_FEATURE
```

```
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 568

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 569
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 569

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 570
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 570

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 571
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
```

```
<222> LOCATION: (37)..(37)
<223> OTHER INFORMATION: Xaa is any amino acid excluding Cys

<400> SEQUENCE: 571

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 572
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 572

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 573
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 573

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 574
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 574
```

```
Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
            35                  40
```

<210> SEQ ID NO 575
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 575

```
Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
            35                  40
```

<210> SEQ ID NO 576
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 576

```
Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn Ser Gly Gly Cys
            35                  40
```

<210> SEQ ID NO 577
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 577

```
Met Val Lys Ile Val Ser Arg Lys Leu Ala Lys Thr Glu Asn Val Tyr
1               5                   10                  15
```

```
Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 578
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 578

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 579
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 579

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 580
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 580

Met Val Lys Val Ile Gly Arg Arg Ser Leu Gly Val Gln Arg Ile Phe
```

```
                 1               5                  10                 15
Asp Ile Gly Leu Pro Gln Asp His Asn Phe Leu Leu Ala Asn Gly Ala
                         20                  25                 30
Ile Ala Ala Xaa Xaa Phe Asn Ser Gly Gly Cys
                 35                  40
```

<210> SEQ ID NO 581
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
     Tyr, Gly or Trp or can be a unnatural aliphatic amino acid residue
     such as norleucine, 2-aminobutyric acid, nor-valine,
     2-aminopentoic acid, or 2-aminohexaanoic acid

<400> SEQUENCE: 581

```
Met Val Lys Ile Ile Lys Arg Gln Ser Leu Gly Arg Gln Asn Val Tyr
1               5                  10                 15
Asp Val Cys Val Glu Thr Asp His Asn Phe Val Leu Ala Asn Gly Cys
                         20                  25                 30
Val Ala Ser Xaa Xaa Phe Asn Ser Gly Gly Cys
                 35                  40
```

<210> SEQ ID NO 582
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
     Tyr, Gly or Trp or can be a unnatural aliphatic amino acid residue
     such as norleucine, 2-aminobutyric acid, nor-valine,
     2-aminopentoic acid, or 2-aminohexaanoic acid

<400> SEQUENCE: 582

```
Met Val Lys Ile Thr Ala Arg Lys Phe Val Gly Arg Glu Asn Val Tyr
1               5                  10                 15
Asp Ile Gly Val Glu His His His Asn Phe Ala Ile Lys Asn Gly Leu
                         20                  25                 30
Ile Ala Ser Xaa Xaa Phe Asn Ser Gly Gly Cys
                 35                  40
```

<210> SEQ ID NO 583
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
     Tyr, Gly or Trp or can be a unnatural aliphatic amino acid residue
     such as norleucine, 2-aminobutyric acid, nor-valine, -continued 2-aminopentoic acid, or 2-aminohexaanoic acid

<400> SEQUENCE: 583

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
        35                  40

<210> SEQ ID NO 584
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 584

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
        35                  40

<210> SEQ ID NO 585
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 585

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
        35                  40

<210> SEQ ID NO 586
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:

```
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 586

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 587
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 587

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 588
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 588

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 589
<211> LENGTH: 43
<212> TYPE: PRT
<213> ORGANISM: Microcystis aeruginosa
```

```
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 589

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 590
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 590

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 591
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 591

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40
```

<210> SEQ ID NO 592
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 592

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
        35                  40

<210> SEQ ID NO 593
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 593

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
        35                  40

<210> SEQ ID NO 594
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 594

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile

```
Ala Ala Xaa Xaa Phe Asn Ser Gly Gly Cys
        35                  40
```

<210> SEQ ID NO 595
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 595

```
Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40
```

<210> SEQ ID NO 596
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 596

```
Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40
```

<210> SEQ ID NO 597
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 597

```
Met Ile Lys Ile Ala Thr Arg Lys Tyr Leu Gly Lys Gln Asn Val Tyr
1               5                   10                  15
```

Asp Ile Gly Val Glu Arg Asp His Asn Phe Ala Leu Lys Asn Gly Phe
            20                  25                  30

Ile Ala Ser Xaa Xaa Phe Asn Ser Gly Gly Cys
        35                  40

<210> SEQ ID NO 598
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 598

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Xaa Phe Asn Ser Gly Gly Cys
        35                  40

<210> SEQ ID NO 599
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 599

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Xaa Phe Asn Ser Gly Gly Cys
        35                  40

<210> SEQ ID NO 600
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 600

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Xaa Phe Asn Ser Gly Gly Cys
            35                  40

<210> SEQ ID NO 601
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 601

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Xaa Phe Asn Ser Gly Gly Cys
            35                  40

<210> SEQ ID NO 602
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 602

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Xaa Xaa Phe Asn Ser Gly Gly Cys
            35                  40

<210> SEQ ID NO 603
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 603

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Xaa Phe Asn Ser Gly Gly Cys
            35                  40

-continued

```
<210> SEQ ID NO 604
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 604

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Xaa Phe Asn Ser Gly Gly Cys
        35                  40

<210> SEQ ID NO 605
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 605

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 606
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 606

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Xaa Xaa Phe Asn Ser Gly Gly Cys
        35                  40

<210> SEQ ID NO 607
<211> LENGTH: 43
<212> TYPE: PRT
<213> ORGANISM: Microcystis aeruginosa
```

```
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 607

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Xaa Xaa Phe Asn Ser Gly Gly Cys
        35                  40

<210> SEQ ID NO 608
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 608

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 609
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 609

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Xaa Xaa Phe Asn Ser Gly Gly Cys
        35                  40

<210> SEQ ID NO 610
<211> LENGTH: 43
<212> TYPE: PRT
<213> ORGANISM: Synechococcus elongatus
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
```

```
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 610

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Xaa Phe Asn Ser Gly Gly Cys
            35                  40

<210> SEQ ID NO 611
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe

<400> SEQUENCE: 611

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Xaa Phe Asn Ser Gly Gly Cys
            35                  40

<210> SEQ ID NO 612
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 612

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Xaa Phe Asn Ser Gly Gly Cys
        35                  40

<210> SEQ ID NO 613
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe
<220> FEATURE:
<221> NAME/KEY: MISC_FEATURE
<222> LOCATION: (37)..(37)
<223> OTHER INFORMATION: Xaa is Ala, Ile Val Leu, Tyr, Gly or Phe
```

-continued

<400> SEQUENCE: 613

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Xaa Phe Asn Ser Gly Gly Cys
        35                  40

<210> SEQ ID NO 614
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 614

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Xaa Xaa Phe Asn Ser Gly Gly Cys
        35                  40

<210> SEQ ID NO 615
<211> LENGTH: 43
<212> TYPE: PRT
<213> ORGANISM: Nostoc punctiforme
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 615

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Xaa Ala Phe Asn Ser Gly Gly Cys
        35                  40

<210> SEQ ID NO 616
<211> LENGTH: 43
<212> TYPE: PRT
<213> ORGANISM: Synechocystis PCC6803
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 616

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Xaa Ala Phe Asn Ser Gly Gly Cys
        35                  40

<210> SEQ ID NO 617
<211> LENGTH: 43
<212> TYPE: PRT
<213> ORGANISM: Aphanothece halophytica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 617

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Xaa Ala Phe Asn Ser Gly Gly Cys
        35                  40

<210> SEQ ID NO 618
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 618

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Xaa Ala Phe Asn Ser Gly Gly Cys
        35                  40

<210> SEQ ID NO 619
<211> LENGTH: 43
<212> TYPE: PRT
<213> ORGANISM: Anabaena PCC7120
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 619

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Xaa Ala Phe Asn Ser Gly Gly Cys
        35                  40

<210> SEQ ID NO 620
<211> LENGTH: 43
<212> TYPE: PRT
<213> ORGANISM: Anabaena variabilis
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 620

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu

```
                    20                  25                  30

Ile Ala Ser Xaa Ala Phe Asn Ser Gly Gly Cys
        35                  40

<210> SEQ ID NO 621
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 621

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Xaa Ala Phe Asn Ser Gly Gly Cys
        35                  40

<210> SEQ ID NO 622
<211> LENGTH: 43
<212> TYPE: PRT
<213> ORGANISM: Cyanothece CCY0110
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 622

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Xaa Ala Phe Asn Ser Gly Gly Cys
        35                  40

<210> SEQ ID NO 623
<211> LENGTH: 43
<212> TYPE: PRT
<213> ORGANISM: Cyanothece PCC8801
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 623

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Xaa Ala Phe Asn Ser Gly Gly Cys
        35                  40

<210> SEQ ID NO 624
<211> LENGTH: 43
<212> TYPE: PRT
<213> ORGANISM: Crocosphaera watsonii
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 624
```

```
Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
                20                  25                  30

Ile Ala Ser Xaa Ala Phe Asn Ser Gly Gly Cys
                35                  40
```

<210> SEQ ID NO 625
<211> LENGTH: 43
<212> TYPE: PRT
<213> ORGANISM: Microcystis aeruginosa
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 625

```
Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
                20                  25                  30

Ile Ala Ser Xaa Ala Phe Asn Ser Gly Gly Cys
                35                  40
```

<210> SEQ ID NO 626
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 626

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Ala Ser Xaa Ala Phe Asn Ser Gly Gly Cys
                35                  40
```

<210> SEQ ID NO 627
<211> LENGTH: 43
<212> TYPE: PRT
<213> ORGANISM: Oscillatoria limnetica
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 627

```
Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
                20                  25                  30

Ile Ala Ser Xaa Ala Phe Asn Ser Gly Gly Cys
                35                  40
```

<210> SEQ ID NO 628
<211> LENGTH: 43
<212> TYPE: PRT
<213> ORGANISM: Synechococcus elongatus
<220> FEATURE:

```
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 628

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Xaa Ala Phe Asn Ser Gly Gly Cys
        35                  40

<210> SEQ ID NO 629
<211> LENGTH: 43
<212> TYPE: PRT
<213> ORGANISM: Synechococcus PCC7002
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 629

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Xaa Ala Phe Asn Ser Gly Gly Cys
        35                  40

<210> SEQ ID NO 630
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe

<400> SEQUENCE: 630

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Xaa Ala Phe Asn Ser Gly Gly Cys
        35                  40

<210> SEQ ID NO 631
<211> LENGTH: 43
<212> TYPE: PRT
<213> ORGANISM: Trichodesmium erythraeum
<220> FEATURE:
<221> NAME/KEY: MISC_FEATURE
<222> LOCATION: (36)..(36)
<223> OTHER INFORMATION: Xaa is Ala, Ile Val Leu, Tyr, Gly or Phe

<400> SEQUENCE: 631

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Xaa Ala Phe Asn Ser Gly Gly Cys
        35                  40
```

```
<210> SEQ ID NO 632
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (35)..(35)
<223> OTHER INFORMATION: Xaa is Ala, Ile Val Leu, Tyr, Gly or Phe

<400> SEQUENCE: 632

Met Lys Ile Val Gly Arg Arg Leu Val Gly Trp Gln Ala Val Tyr Asp
1               5                   10                  15

Ile Gly Leu Ala Gly Asp His Asn Phe Leu Ala Asn Gly Ala Ile
            20                  25                  30

Ala Ala Xaa Ala Phe Asn Ser Gly Gly Cys
        35                  40

<210> SEQ ID NO 633
<211> LENGTH: 43
<212> TYPE: PRT
<213> ORGANISM: Nostoc punctiforme
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 633

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn Ser Gly Gly Cys
        35                  40

<210> SEQ ID NO 634
<211> LENGTH: 39
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 634

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Xaa Phe Asn
        35

<210> SEQ ID NO 635
<211> LENGTH: 39
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 635

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30
```

Val Ala Ser Ala Xaa Phe Asn
        35

<210> SEQ ID NO 636
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 636

Met Val Lys Ile Thr Ala Arg Lys Phe Val Gly Arg Glu Asn Val Tyr
1               5                   10                  15

Asp Ile Gly Val Glu His His Asn Phe Ala Ile Lys Asn Gly Leu
            20                  25                  30

Ile Ala Ser Ala Xaa Phe Asn Ser Gly Gly Cys
        35                  40

<210> SEQ ID NO 637
<211> LENGTH: 43
<212> TYPE: PRT
<213> ORGANISM: Anabaena PCC7120
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 637

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala Xaa Phe Asn Ser Gly Gly Cys
        35                  40

<210> SEQ ID NO 638
<211> LENGTH: 43
<212> TYPE: PRT
<213> ORGANISM: Anabaena variabilis
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 638

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala Xaa Phe Asn Ser Gly Gly Cys
        35                  40

<210> SEQ ID NO 639
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 639

-continued

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Xaa Phe Asn Ser Gly Gly Cys
        35                  40

<210> SEQ ID NO 640
<211> LENGTH: 43
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 640

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Xaa Phe Asn Ser Gly Gly Cys
        35                  40

<210> SEQ ID NO 641
<211> LENGTH: 43
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 641

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Xaa Phe Asn Ser Gly Gly Cys
        35                  40

<210> SEQ ID NO 642
<211> LENGTH: 43
<212> TYPE: PRT
<213> ORGANISM: Crocosphaera watsonii
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 642

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala Xaa Phe Asn Ser Gly Gly Cys
        35                  40

<210> SEQ ID NO 643
<211> LENGTH: 43
<212> TYPE: PRT
<213> ORGANISM: Microcystis aeruginosa
<220> FEATURE:
<221> NAME/KEY: MISC_FEATURE

```
<222> LOCATION: (37)..(37)
<223> OTHER INFORMATION: Xaa is any amino acid excluding Cys

<400> SEQUENCE: 643

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala Xaa Phe Asn Ser Gly Gly Cys
        35                  40

<210> SEQ ID NO 644
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 644

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

<210> SEQ ID NO 645
<211> LENGTH: 43
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 645

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

<210> SEQ ID NO 646
<211> LENGTH: 43
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 646

Met Val Lys Ile Val Arg Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Xaa Phe Asn Ser Gly Gly Cys
        35                  40

<210> SEQ ID NO 647
```

```
<211> LENGTH: 43
<212> TYPE: PRT
<213> ORGANISM: Synechococcus PCC7002
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 647

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Xaa Phe Asn Ser Gly Gly Cys
        35                  40

<210> SEQ ID NO 648
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 648

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Xaa Phe Asn Ser Gly Gly Cys
        35                  40

<210> SEQ ID NO 649
<211> LENGTH: 43
<212> TYPE: PRT
<213> ORGANISM: Trichodesmium erythraeum
<220> FEATURE:
<221> NAME/KEY: MISC_FEATURE
<222> LOCATION: (37)..(37)
<223> OTHER INFORMATION: Xaa is any amino acid excluding Cys

<400> SEQUENCE: 649

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Xaa Phe Asn Ser Gly Gly Cys
        35                  40

<210> SEQ ID NO 650
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 650

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30
```

Ala Ala Ala Xaa Phe Asn Ser Gly Gly Cys
        35                  40

<210> SEQ ID NO 651
<211> LENGTH: 43
<212> TYPE: PRT
<213> ORGANISM: Nostoc punctiforme
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 651

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn Ser Gly Gly Cys
        35                  40

<210> SEQ ID NO 652
<211> LENGTH: 43
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 652

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Xaa Phe Asn Ser Gly Gly Cys
        35                  40

<210> SEQ ID NO 653
<211> LENGTH: 43
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 653

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Xaa Phe Asn Ser Gly Gly Cys
        35                  40

<210> SEQ ID NO 654
<211> LENGTH: 43
<212> TYPE: PRT

-continued

```
<213> ORGANISM: Aphanizomenon ovalisporum
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE

-continued 2-aminopentoic acid, or 2-aminohexaanoic acid

<400> SEQUENCE: 657

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Xaa Phe Asn Ser Gly Gly Cys
        35                  40

<210> SEQ ID NO 658
<211> LENGTH: 43
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 658

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Xaa Phe Asn Ser Gly Gly Cys
        35                  40

<210> SEQ ID NO 659
<211> LENGTH: 43
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 659

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Xaa Phe Asn Ser Gly Gly Cys
        35                  40

<210> SEQ ID NO 660
<211> LENGTH: 43
<212> TYPE: PRT
<213> ORGANISM: Crocosphaera watsonii
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 660

Met Val Lys Ile Ile Gly Cys Arg Ser Leu Gly Thr Gln Lys Val Tyr
1               5                   10                  15

-continued

Asp Ile Gly Val Glu Lys Asp His Asn Phe Leu Leu Ala Asn Gly Ser
            20                  25                  30

Ile Ala Ser Ala Xaa Phe Asn Ser Gly Gly Cys
        35                  40

<210> SEQ ID NO 661
<211> LENGTH: 43
<212> TYPE: PRT
<213> ORGANISM: Microcystis aeruginosa
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 661

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala Xaa Phe Asn Ser Gly Gly Cys
        35                  40

<210> SEQ ID NO 662
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 662

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

<210> SEQ ID NO 663
<211> LENGTH: 43
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 663

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

```
<210> SEQ ID NO 664
<211> LENGTH: 43
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 664

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Xaa Phe Asn Ser Gly Gly Cys
        35                  40

<210> SEQ ID NO 665
<211> LENGTH: 43
<212> TYPE: PRT
<213> ORGANISM: Synechococcus PCC7002
<220> FEATURE:
<221> NAME/KEY: MISC_FEATURE
<222> LOCATION: (37)..(37)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 665

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Xaa Phe Asn Ser Gly Gly Cys
        35                  40

<210> SEQ ID NO 666
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 666

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Xaa Phe Asn Ser Gly Gly Cys
        35                  40

<210> SEQ ID NO 667
<211> LENGTH: 43
<212> TYPE: PRT
<213> ORGANISM: Trichodesmium erythraeum
<220> FEATURE:
<221> NAME/KEY: MISC_FEATURE
<222> LOCATION: (37)..(37)
```

```
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 667

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Xaa Phe Asn Ser Gly Gly Cys
        35                  40

<210> SEQ ID NO 668
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 668

Met Lys Ile Val Gly Arg Arg Leu Val Gly Trp Gln Ala Val Tyr Asp
1               5                   10                  15

Ile Gly Leu Ala Gly Asp His Asn Phe Leu Leu Ala Asn Gly Ala Ile
            20                  25                  30

Ala Ala Ala Xaa Phe Asn Ser Gly Gly Cys
        35                  40

<210> SEQ ID NO 669
<211> LENGTH: 43
<212> TYPE: PRT
<213> ORGANISM: Nostoc punctiforme
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 669

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Xaa Phe Asn Ser Gly Gly Cys
        35                  40

<210> SEQ ID NO 670
<211> LENGTH: 43
<212> TYPE: PRT
<213> ORGANISM: Synechocystis PCC6803
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 670

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30
```

Ile Ala Ala Ala Xaa Phe Asn Ser Gly Gly Cys
            35                  40

<210> SEQ ID NO 671
<211> LENGTH: 43
<212> TYPE: PRT
<213> ORGANISM: Aphanothece halophytica
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 671

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Xaa Phe Asn Ser Gly Gly Cys
            35                  40

<210> SEQ ID NO 672
<211> LENGTH: 43
<212> TYPE: PRT
<213> ORGANISM: Aphanizomenon ovalisporum
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 672

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Ala Xaa Phe Asn Ser Gly Gly Cys
            35                  40

<210> SEQ ID NO 673
<211> LENGTH: 43
<212> TYPE: PRT
<213> ORGANISM: Anabaena PCC7120
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 673

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala Xaa Phe Asn Ser Gly Gly Cys
            35                  40

<210> SEQ ID NO 674
<211> LENGTH: 43
<212> TYPE: PRT
<213> ORGANISM: Anabaena variabilis
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 674

Met Ile Lys Ile Ala Ser Arg Lys Phe Leu Gly Val Glu Asn Val Tyr

```
1               5                   10                  15
Asp Ile Gly Val Gly Arg Asp His Asn Phe Phe Val Lys Asn Gly Leu
            20                  25                  30

Ile Ala Ser Ala Xaa Phe Asn Ser Gly Gly Cys
            35                  40
```

<210> SEQ ID NO 675
<211> LENGTH: 43
<212> TYPE: PRT
<213> ORGANISM: Cylindrospermopsis raciborskii
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 675

```
Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Xaa Phe Asn Ser Gly Gly Cys
            35                  40
```

<210> SEQ ID NO 676
<211> LENGTH: 43
<212> TYPE: PRT
<213> ORGANISM: Cyanothece CCY0110
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 676

```
Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Xaa Phe Asn Ser Gly Gly Cys
            35                  40
```

<210> SEQ ID NO 677
<211> LENGTH: 43
<212> TYPE: PRT
<213> ORGANISM: Cyanothece PCC8801
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 677

```
Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Xaa Phe Asn Ser Gly Gly Cys
            35                  40
```

<210> SEQ ID NO 678
<211> LENGTH: 43
<212> TYPE: PRT
<213> ORGANISM: Crocosphaera watsonii
<220> FEATURE:
<221> NAME/KEY: MISC_FEATURE
<222> LOCATION: (37)..(37)

-continued

<223> OTHER INFORMATION: Xaa is Ala, Ile, Val, Leu, Tyr, Gly or Phe

<400> SEQUENCE: 678

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala Xaa Phe Asn Ser Gly Gly Cys
        35                  40

<210> SEQ ID NO 679
<211> LENGTH: 43
<212> TYPE: PRT
<213> ORGANISM: Microcystis aeruginosa
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 679

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala Xaa Phe Asn Ser Gly Gly Cys
        35                  40

<210> SEQ ID NO 680
<211> LENGTH: 43
<212> TYPE: PRT
<213> ORGANISM: Microcoleus chthonoplastes
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 680

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

<210> SEQ ID NO 681
<211> LENGTH: 43
<212> TYPE: PRT
<213> ORGANISM: Oscillatoria limnetica
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 681

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Xaa Phe Asn Ser Gly Gly Cys
        35                  40

<210> SEQ ID NO 682
<211> LENGTH: 43

```
<212> TYPE: PRT
<213> ORGANISM: Synechococcus elongatus
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 682

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
                20                  25                  30

Val Ala Ser Ala Xaa Phe Asn Ser Gly Gly Cys
            35                  40

<210> SEQ ID NO 683
<211> LENGTH: 43
<212> TYPE: PRT
<213> ORGANISM: Synechococcus PCC7002
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 683

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
                20                  25                  30

Ile Ala Ala Ala Xaa Phe Asn Ser Gly Gly Cys
            35                  40

<210> SEQ ID NO 684
<211> LENGTH: 42
<212> TYPE: PRT
<213> ORGANISM: Thermosynechococcus elongatus
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 684

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
                20                  25                  30

Ala Ala Ala Xaa Phe Asn Ser Gly Gly Cys
            35                  40

<210> SEQ ID NO 685
<211> LENGTH: 43
<212> TYPE: PRT
<213> ORGANISM: Trichodesmium erythraeum
<220> FEATURE:
<221> NAME/KEY: MISC_FEATURE
<222> LOCATION: (37)..(37)
<223> OTHER INFORMATION: Xaa is Ala, Ile, Val, Leu, Tyr, Gly or Phe

<400> SEQUENCE: 685

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
                20                  25                  30

Ile Ala Ser Ala Xaa Phe Asn Ser Gly Gly Cys
```

-continued

```
                 35                  40

<210> SEQ ID NO 686
<211> LENGTH: 42
<212> TYPE: PRT
<213> ORGANISM: Thermosynechococcus vulcanus
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 686

Met Lys Ile Val Gly Arg Arg Leu Val Gly Trp Gln Ala Val Tyr Asp
1               5                   10                  15

Ile Gly Leu Ala Gly Asp His Asn Phe Leu Ala Asn Gly Ala Ile
            20                  25                  30

Ala Ala Ala Xaa Phe Asn Ser Gly Gly Cys
        35                  40

<210> SEQ ID NO 687
<211> LENGTH: 43
<212> TYPE: PRT
<213> ORGANISM: Nostoc punctiforme

<400> SEQUENCE: 687

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Ala Ala Phe Asn Ser Gly Gly Cys
        35                  40

<210> SEQ ID NO 688
<211> LENGTH: 43
<212> TYPE: PRT
<213> ORGANISM: Synechocystis PCC6803

<400> SEQUENCE: 688

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Ala Ala Phe Asn Ser Gly Gly Cys
        35                  40

<210> SEQ ID NO 689
<211> LENGTH: 43
<212> TYPE: PRT
<213> ORGANISM: Aphanothece halophytica

<400> SEQUENCE: 689

Met Val Lys Ile Ile Lys Arg Gln Ser Leu Gly Arg Gln Asn Val Tyr
1               5                   10                  15

Asp Val Cys Val Glu Thr Asp His Asn Phe Val Leu Ala Asn Gly Cys
            20                  25                  30

Val Ala Ser Ala Ala Phe Asn Ser Gly Gly Cys
        35                  40

<210> SEQ ID NO 690
<211> LENGTH: 43
<212> TYPE: PRT
<213> ORGANISM: Aphanizomenon ovalisporum
```

<400> SEQUENCE: 690

Met Val Lys Ile Thr Ala Arg Lys Phe Val Gly Arg Glu Asn Val Tyr
1               5                   10                  15

Asp Ile Gly Val Glu His His His Asn Phe Ala Ile Lys Asn Gly Leu
            20                  25                  30

Ile Ala Ser Ala Ala Phe Asn Ser Gly Gly Cys
        35                  40

<210> SEQ ID NO 691
<211> LENGTH: 39
<212> TYPE: PRT
<213> ORGANISM: Anabaena PCC7120

<400> SEQUENCE: 691

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Ala Ala Phe Asn
        35

<210> SEQ ID NO 692
<211> LENGTH: 43
<212> TYPE: PRT
<213> ORGANISM: Anabaena variabilis

<400> SEQUENCE: 692

Met Ile Lys Ile Ala Ser Arg Lys Phe Leu Gly Val Glu Asn Val Tyr
1               5                   10                  15

Asp Ile Gly Val Gly Arg Asp His Asn Phe Phe Val Lys Asn Gly Leu
            20                  25                  30

Ile Ala Ser Ala Ala Phe Asn Ser Gly Gly Cys
        35                  40

<210> SEQ ID NO 693
<211> LENGTH: 43
<212> TYPE: PRT
<213> ORGANISM: Cylindrospermopsis raciborskii

<400> SEQUENCE: 693

Met Val Lys Ile Val Ser Arg Arg Tyr Leu Gly Lys Ala Asp Val Tyr
1               5                   10                  15

Asp Ile Gly Val Ala Lys Asp His Asn Phe Ile Ile Lys Asn Gly Leu
            20                  25                  30

Val Ala Ser Ala Ala Phe Asn Ser Gly Gly Cys
        35                  40

<210> SEQ ID NO 694
<211> LENGTH: 43
<212> TYPE: PRT
<213> ORGANISM: Cyanothece CCY0110

<400> SEQUENCE: 694

Met Val Lys Ile Ile Glu Arg Arg Ser Leu Gly Lys Gln Asn Val Tyr
1               5                   10                  15

Asp Ile Gly Val Glu Lys Asp His Asn Phe Leu Leu Ser Asn Asn Leu
            20                  25                  30

Ile Ala Ser Ala Ala Phe Asn Ser Gly Gly Cys
        35                  40

<210> SEQ ID NO 695
<211> LENGTH: 43
<212> TYPE: PRT
<213> ORGANISM: Cyanothece PCC8801

<400> SEQUENCE: 695

Met Val Lys Ile Val Ser Tyr Arg Ser Leu Gly Lys Gln Phe Val Tyr
1               5                   10                  15

Asp Ile Gly Val Ala Gln Asp His Asn Phe Leu Leu Ala Asn Gly Ser
            20                  25                  30

Ile Ala Ser Ala Ala Phe Asn Ser Gly Gly Cys
        35                  40

<210> SEQ ID NO 696
<211> LENGTH: 43
<212> TYPE: PRT
<213> ORGANISM: Crocosphaera watsonii

<400> SEQUENCE: 696

Met Val Lys Ile Ile Gly Cys Arg Ser Leu Gly Thr Gln Lys Val Tyr
1               5                   10                  15

Asp Ile Gly Val Glu Lys Asp His Asn Phe Leu Leu Ala Asn Gly Ser
            20                  25                  30

Ile Ala Ser Ala Ala Phe Asn Ser Gly Gly Cys
        35                  40

<210> SEQ ID NO 697
<211> LENGTH: 43
<212> TYPE: PRT
<213> ORGANISM: Microcystis aeruginosa

<400> SEQUENCE: 697

Met Val Lys Ile Ile Gly Arg Gln Ser Leu Gly Arg Lys Pro Val Tyr
1               5                   10                  15

Asp Ile Gly Val Glu Lys Asp His Asn Phe Leu Leu Gly Asn Gly Leu
            20                  25                  30

Ile Ala Ser Ala Ala Phe Asn Ser Gly Gly Cys
        35                  40

<210> SEQ ID NO 698
<211> LENGTH: 43
<212> TYPE: PRT
<213> ORGANISM: Microcoleus chthonoplastes

<400> SEQUENCE: 698

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Ala Ala Phe Asn Ser Gly Gly Cys
        35                  40

<210> SEQ ID NO 699
<211> LENGTH: 43
<212> TYPE: PRT
<213> ORGANISM: Oscillatoria limnetica

<400> SEQUENCE: 699

Met Val Lys Ile Val Arg Arg Gln Ser Leu Gly Val Gln Asn Val Tyr
1               5                   10                  15

```
Asp Ile Gly Val Glu Lys Asp His Asn Phe Cys Leu Ala Ser Gly Glu
            20                  25                  30

Ile Ala Ser Ala Ala Phe Asn Ser Gly Gly Cys
            35                  40

<210> SEQ ID NO 700
<211> LENGTH: 43
<212> TYPE: PRT
<213> ORGANISM: Synechococcus elongatus

<400> SEQUENCE: 700

Met Val Lys Ile Val Arg Arg Ser Leu Gly Val Gln Pro Val Tyr
1               5                   10                  15

Asp Leu Gly Val Ala Thr Val His Asn Phe Val Leu Ala Asn Gly Leu
            20                  25                  30

Val Ala Ser Ala Ala Phe Asn Ser Gly Gly Cys
            35                  40

<210> SEQ ID NO 701
<211> LENGTH: 43
<212> TYPE: PRT
<213> ORGANISM: Synechococcus PCC7002

<400> SEQUENCE: 701

Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Ala Ala Phe Asn Ser Gly Gly Cys
            35                  40

<210> SEQ ID NO 702
<211> LENGTH: 42
<212> TYPE: PRT
<213> ORGANISM: Thermosynechococcus elongatus

<400> SEQUENCE: 702

Met Lys Ile Val Gly Arg Arg Leu Met Gly Trp Gln Ala Val Tyr Asp
1               5                   10                  15

Ile Gly Leu Ala Ala Asp His Asn Phe Val Leu Ala Asn Gly Ala Ile
            20                  25                  30

Ala Ala Ala Ala Phe Asn Ser Gly Gly Cys
            35                  40

<210> SEQ ID NO 703
<211> LENGTH: 43
<212> TYPE: PRT
<213> ORGANISM: Trichodesmium erythraeum

<400> SEQUENCE: 703

Met Val Lys Ile Val Ser Arg Lys Leu Ala Lys Thr Glu Asn Val Tyr
1               5                   10                  15

Asp Ile Gly Val Thr Lys Asp His Asn Phe Val Leu Ala Asn Gly Leu
            20                  25                  30

Ile Ala Ser Ala Ala Phe Asn Ser Gly Gly Cys
            35                  40

<210> SEQ ID NO 704
<211> LENGTH: 42
<212> TYPE: PRT
```

<213> ORGANISM: Thermosynechococcus vulcanus

<400> SEQUENCE: 704

Met Lys Ile Val Gly Arg Arg Leu Val Gly Trp Gln Ala Val Tyr Asp
1               5                   10                  15

Ile Gly Leu Ala Gly Asp His Asn Phe Leu Ala Asn Gly Ala Ile
            20                  25                  30

Ala Ala Ala Ala Phe Asn Ser Gly Gly Cys
        35                  40

<210> SEQ ID NO 705
<211> LENGTH: 4
<212> TYPE: PRT
<213> ORGANISM: Artificial Sequence
<220> FEATURE:
<223> OTHER INFORMATION: Linker

<400> SEQUENCE: 705

Ser Gly Gly Cys
1

<210> SEQ ID NO 706
<211> LENGTH: 8
<212> TYPE: PRT
<213> ORGANISM: Artificial Sequence
<220> FEATURE:
<223> OTHER INFORMATION: Linker

<400> SEQUENCE: 706

Ala Ala Phe Asn Ser Gly Gly Cys
1               5

<210> SEQ ID NO 707
<211> LENGTH: 35
<212> TYPE: PRT
<213> ORGANISM: Artificial Sequence
<220> FEATURE:
<223> OTHER INFORMATION: C-fragment consensus sequence

<400> SEQUENCE: 707

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Asn
        35

<210> SEQ ID NO 708
<211> LENGTH: 35
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 708

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa

<210> SEQ ID NO 709
<211> LENGTH: 35
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 709

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa
        35

<210> SEQ ID NO 710
<211> LENGTH: 35
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 710

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa
        35

<210> SEQ ID NO 711
<211> LENGTH: 35
<212> TYPE: PRT
<213> ORGANISM: Artificial Sequence
<220> FEATURE:
<223> OTHER INFORMATION: C-fragment consensus sequence

<400> SEQUENCE: 711

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala
        35

<210> SEQ ID NO 712
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE

```
<222> LOCATION: (35)..(35)
<223> OTHER INFORMATION: Xaa is any amino acid exclusing Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 712

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35

<210> SEQ ID NO 713
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 713

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35

<210> SEQ ID NO 714
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 714

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35

<210> SEQ ID NO 715
<211> LENGTH: 36
<212> TYPE: PRT
```

```
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 715

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala
        35

<210> SEQ ID NO 716
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 716

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35

<210> SEQ ID NO 717
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 717

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30
```

Ala Ser Xaa Xaa
        35

<210> SEQ ID NO 718
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 718

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35

<210> SEQ ID NO 719
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 719

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala
        35

<210> SEQ ID NO 720
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 720

Val Lys Ile Ile Ser Arg Gln Ser Leu Gly Lys Gln Asn Val Tyr Asp
1               5                   10                  15

```
Ile Gly Val Glu Lys Asp His Asn Phe Leu Leu Ala Asn Gly Leu Ile
            20                  25                  30

Ala Ser Xaa Xaa
        35
```

<210> SEQ ID NO 721
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 721

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35
```

<210> SEQ ID NO 722
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 722

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa
        35
```

<210> SEQ ID NO 723
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 723

```
Val Lys Ile Ile Ser Arg Gln Ser Leu Gly Lys Gln Asn Val Tyr Asp
```

```
                1               5                   10                  15
Ile Gly Val Glu Lys Asp His Asn Phe Leu Leu Ala Asn Gly Leu Ile
                20                  25                  30

Ala Ser Xaa Ala
        35
```

<210> SEQ ID NO 724
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 724

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
                20                  25                  30

Ala Ser Ala Xaa
        35
```

<210> SEQ ID NO 725
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 725

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
                20                  25                  30

Ala Ser Ala Xaa
        35
```

<210> SEQ ID NO 726
<211> LENGTH: 36
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 726

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
                20                  25                  30

Ala Ser Ala Xaa
        35
```

<210> SEQ ID NO 727
<211> LENGTH: 36
<212> TYPE: PRT
<213> ORGANISM: Artificial Sequence
<220> FEATURE:
<223> OTHER INFORMATION: C-fragment consensus sequence

<400> SEQUENCE: 727

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Ala
        35

<210> SEQ ID NO 728
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid exclusing Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 728

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 729
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
    Tyr, Gly or Trp or can be a unnatural aliphatic amino acid residue
    such as norleucine, 2-aminobutyric acid, nor-valine,
    2-aminopentoic acid, or 2-aminohexaanoic acid

<400> SEQUENCE: 729

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 730

```
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 730

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 731
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 731

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala Phe Asn
        35

<210> SEQ ID NO 732
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 732

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35
```

```
<210> SEQ ID NO 733
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 733

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 734
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 734

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 735
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 735
```

```
Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala Phe Asn
        35

<210> SEQ ID NO 736
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 736

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 737
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 737

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 738
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
```

```
<222> LOCATION: (36)..(36)
<223> OTHER INFORMATION: Xaa is Ala, Ile, Val, Leu, Tyr, Gly or Phe

<400> SEQUENCE: 738

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn
        35

<210> SEQ ID NO 739
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 739

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala Phe Asn
        35

<210> SEQ ID NO 740
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 740

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Xaa Phe Asn
        35

<210> SEQ ID NO 741
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 741

Val Lys Ile Ile Ser Arg Gln Ser Leu Gly Lys Gln Asn Val Tyr Asp
1               5                   10                  15
```

Ile Gly Val Glu Lys Asp His Asn Phe Leu Leu Ala Asn Gly Leu Ile
            20                  25                  30

Ala Ser Ala Xaa Phe Asn
        35

<210> SEQ ID NO 742
<211> LENGTH: 38
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 742

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Xaa Phe Asn
        35

<210> SEQ ID NO 743
<211> LENGTH: 38
<212> TYPE: PRT
<213> ORGANISM: Artificial Sequence
<220> FEATURE:
<223> OTHER INFORMATION: C-fragment consensus sequence

<400> SEQUENCE: 743

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Ala Phe Asn
        35

<210> SEQ ID NO 744
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid exclusing Asn and/or Gln
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 744

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 745
<211> LENGTH: 42

```
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 745

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 746
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 746

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 747
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is any amino acid excluding Asn and/or Gln

<400> SEQUENCE: 747

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala Phe Asn Ser Gly Gly Cys
        35                  40

<210> SEQ ID NO 748
```

```
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 748

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 749
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 749

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 750
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe
```

```
<400> SEQUENCE: 750

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 751
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 751

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Ala Phe Asn Ser Gly Gly Cys
        35                  40

<210> SEQ ID NO 752
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 752

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 753
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
```

```
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 753

Val Lys Ile Ile Ser Arg Gln Ser Leu Gly Lys Gln Asn Val Tyr Asp
1               5                  10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 754
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 754

Val Lys Ile Ile Ser Arg Gln Ser Leu Gly Lys Gln Asn Val Tyr Asp
1               5                  10                  15

Ile Gly Val Glu Lys Asp His Asn Phe Leu Leu Ala Asn Gly Leu Ile
            20                  25                  30

Ala Ser Xaa Xaa Phe Asn Ser Gly Gly Cys
        35                  40

<210> SEQ ID NO 755
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (35)..(35)
<223> OTHER INFORMATION: Xaa is Ala, Ile, Val, Leu, Tyr, Gly or Phe

<400> SEQUENCE: 755

Val Lys Ile Ile Ser Arg Gln Ser Leu Gly Lys Gln Asn Val Tyr Asp
1               5                  10                  15

Ile Gly Val Glu Lys Asp His Asn Phe Leu Leu Ala Asn Gly Leu Ile
            20                  25                  30

Ala Ser Xaa Ala Phe Asn Ser Gly Gly Cys
        35                  40

<210> SEQ ID NO 756
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is any amino acid excluding Cys

<400> SEQUENCE: 756
```

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Xaa Phe Asn Ser Gly Gly Cys
        35                  40

<210> SEQ ID NO 757
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Val, Ile, Ser, Met, His, Leu, Phe,
      Tyr, Gly or Trp or can be a unnatural aliphatic amino acid residue
      such as norleucine, 2-aminobutyric acid, nor-valine,
      2-aminopentoic acid, or 2-aminohexaanoic acid

<400> SEQUENCE: 757

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Xaa Phe Asn Ser Gly Gly Cys
        35                  40

<210> SEQ ID NO 758
<211> LENGTH: 42
<212> TYPE: PRT
<213> ORGANISM: Artificial Sequence
<220> FEATURE:
<223> OTHER INFORMATION: C-fragment consensus sequence
<220> FEATURE:
<221> NAME/KEY: MISC_FEATURE
<222> LOCATION: (36)..(36)
<223> OTHER INFORMATION: Xaa is Ala, Ile, Val, Leu, Tyr, Gly or Phe

<400> SEQUENCE: 758

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Xaa Phe Asn Ser Gly Gly Cys
        35                  40

<210> SEQ ID NO 759
<211> LENGTH: 42
<212> TYPE: PRT
<213> ORGANISM: Artificial Sequence
<220> FEATURE:
<223> OTHER INFORMATION: C-fragment consensus sequence

<400> SEQUENCE: 759

Val Lys Ile Ile Ser Arg Gln Ser Leu Gly Lys Gln Asn Val Tyr Asp
1               5                   10                  15

Ile Gly Val Glu Lys Asp His Asn Phe Leu Leu Ala Asn Gly Leu Ile
            20                  25                  30

Ala Ser Ala Ala Phe Asn Ser Gly Gly Cys
        35                  40

<210> SEQ ID NO 760
<211> LENGTH: 10
<212> TYPE: PRT
<213> ORGANISM: Artificial Sequence
<220> FEATURE:
<223> OTHER INFORMATION: c-myc epitope tag

<400> SEQUENCE: 760

Glu Gln Lys Leu Ile Ser Glu Glu Asp Leu
1               5                   10

<210> SEQ ID NO 761
<211> LENGTH: 102
<212> TYPE: PRT
<213> ORGANISM: Artificial Sequence
<220> FEATURE:
<223> OTHER INFORMATION: N-fragment modified consensus sequence
<220> FEATURE:
<221> NAME/KEY: MISC_FEATURE
<222> LOCATION: (28)..(28)
<223> OTHER INFORMATION: Xaa is Ala or Ser
<220> FEATURE:
<221> NAME/KEY: MISC_FEATURE
<222> LOCATION: (59)..(59)
<223> OTHER INFORMATION: Xaa is Ala or Ser

<400> SEQUENCE: 761

Cys Leu Ser Tyr Asp Thr Glu Ile Leu Thr Val Glu Tyr Gly Ala Val
1               5                   10                  15

Pro Ile Gly Lys Ile Val Glu Glu Asn Ile Glu Xaa Thr Val Tyr Ser
                20                  25                  30

Val Asp Glu Asn Gly Phe Val Tyr Thr Gln Pro Ile Ala Gln Trp His
            35                  40                  45

Asp Arg Gly Glu Gln Glu Val Phe Glu Tyr Xaa Leu Glu Asp Gly Ser
        50                  55                  60

Thr Ile Arg Ala Thr Lys Asp His Lys Phe Met Thr Glu Asp Gly Glu
65                  70                  75                  80

Met Leu Pro Ile Asp Glu Ile Phe Glu Gln Gly Leu Asp Leu Lys Gln
                85                  90                  95

Val Lys Gly Leu Pro Asp
            100

<210> SEQ ID NO 762
<211> LENGTH: 196
<212> TYPE: PRT
<213> ORGANISM: Artificial Sequence
<220> FEATURE:
<223> OTHER INFORMATION: Synthetic peptide

<400> SEQUENCE: 762

Met His His His His His His Gly Gly Met Gln Ile Phe Val Lys Thr
1               5                   10                  15

Leu Thr Gly Lys Thr Ile Thr Leu Glu Val Glu Ser Ser Asp Thr Ile
                20                  25                  30

Asp Asn Val Lys Ser Lys Ile Gln Asp Lys Glu Gly Ile Pro Pro Asp
            35                  40                  45

Gln Gln Glu Leu Ile Phe Ala Gly Lys Gln Leu Glu Asp Gly Arg Thr
        50                  55                  60

Leu Ser Asp Tyr Asn Ile Gln Lys Glu Ser Thr Leu His Leu Val Leu
65                  70                  75                  80

Arg Leu Arg Gly Gly Gly Gly Gly Lys Phe Ala Glu Tyr Cys Leu
                85                  90                  95

```
Ser Tyr Glu Thr Glu Ile Leu Thr Val Glu Tyr Gly Leu Leu Pro Ile
            100                 105                 110

Gly Lys Ile Val Glu Lys Arg Ile Glu Cys Thr Val Tyr Ser Val Asp
        115                 120                 125

Asn Asn Gly Asn Ile Tyr Thr Gln Pro Val Ala Gln Trp His Asp Arg
    130                 135                 140

Gly Glu Gln Glu Val Phe Glu Tyr Cys Leu Glu Asp Gly Ser Leu Ile
145                 150                 155                 160

Arg Ala Thr Lys Asp His Lys Phe Met Thr Val Asp Gly Gln Met Leu
                165                 170                 175

Pro Ile Asp Glu Ile Phe Glu Arg Glu Leu Asp Leu Met Arg Val Asp
            180                 185                 190

Asn Leu Pro Asn
        195

<210> SEQ ID NO 763
<211> LENGTH: 192
<212> TYPE: PRT
<213> ORGANISM: Artificial Sequence
<220> FEATURE:
<223> OTHER INFORMATION: Synthetic peptide

<400> SEQUENCE: 763

Met His His His His His Gly Gly Met Gln Ile Phe Val Lys Thr
1               5                   10                  15

Leu Thr Gly Lys Thr Ile Thr Leu Glu Val Glu Ser Ser Asp Thr Ile
            20                  25                  30

Asp Asn Val Lys Ser Lys Ile Gln Asp Lys Glu Gly Ile Pro Pro Asp
        35                  40                  45

Gln Gln Glu Leu Ile Phe Ala Gly Lys Gln Leu Glu Asp Gly Arg Thr
    50                  55                  60

Leu Ser Asp Tyr Asn Ile Gln Lys Glu Ser Thr Leu His Leu Val Leu
65                  70                  75                  80

Arg Leu Arg Gly Gly Lys Phe Ala Glu Tyr Cys Leu Ser Tyr Glu Thr
                85                  90                  95

Glu Ile Leu Thr Val Glu Tyr Gly Leu Leu Pro Ile Gly Lys Ile Val
            100                 105                 110

Glu Lys Arg Ile Glu Cys Thr Val Tyr Ser Val Asp Asn Asn Gly Asn
        115                 120                 125

Ile Tyr Thr Gln Pro Val Ala Gln Trp His Asp Arg Gly Glu Gln Glu
    130                 135                 140

Val Phe Glu Tyr Cys Leu Glu Asp Gly Ser Leu Ile Arg Ala Thr Lys
145                 150                 155                 160

Asp His Lys Phe Met Thr Val Asp Gly Gln Met Leu Pro Ile Asp Glu
                165                 170                 175

Ile Phe Glu Arg Glu Leu Asp Leu Met Arg Val Asp Asn Leu Pro Asn
            180                 185                 190

<210> SEQ ID NO 764
<211> LENGTH: 156
<212> TYPE: PRT
<213> ORGANISM: Artificial Sequence
<220> FEATURE:
<223> OTHER INFORMATION: Synthetic peptide

<400> SEQUENCE: 764

Gly Ile Lys Ile Ala Thr Arg Lys Tyr Leu Gly Lys Gln Asn Val Tyr
1               5                   10                  15
```

```
Asp Ile Gly Val Glu Arg Asp His Asn Phe Ala Leu Lys Asn Gly Phe
            20                  25                  30

Ile Ala Ser Asn Cys Phe Asn Ser Gly Leu Val Pro Arg Gly Ser Ala
        35                  40                  45

Ser Met Ser Asp Ser Glu Val Asn Gln Glu Ala Lys Pro Glu Val Lys
 50                  55                  60

Pro Glu Val Lys Pro Glu Thr His Ile Asn Leu Lys Val Ser Asp Gly
 65                  70                  75                  80

Ser Ser Glu Ile Phe Phe Lys Ile Lys Lys Thr Thr Pro Leu Arg Arg
                85                  90                  95

Leu Met Glu Ala Phe Ala Lys Arg Gln Gly Lys Glu Met Asp Ser Leu
                100                 105                 110

Arg Phe Leu Tyr Asp Gly Ile Arg Ile Gln Ala Asp Gln Thr Pro Glu
            115                 120                 125

Asp Leu Asp Met Glu Asp Asn Asp Ile Ile Glu Ala His Arg Glu Gln
130                 135                 140

Ile Gly Gly Tyr Pro Tyr Asp Val Pro Asp Tyr Ala
145                 150                 155
```

<210> SEQ ID NO 765
<211> LENGTH: 283
<212> TYPE: PRT
<213> ORGANISM: Artificial Sequence
<220> FEATURE:
<223> OTHER INFORMATION: Synthetic peptide

<400> SEQUENCE: 765

```
Met Gln Ile Phe Val Lys Thr Leu Thr Gly Lys Thr Ile Thr Leu Glu
 1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly Cys Ile Thr Gly
 65                  70                  75                  80

Asp Ala Leu Val Ala Leu Pro Glu Gly Glu Ser Val Arg Ile Ala Asp
                85                  90                  95

Ile Val Pro Gly Ala Arg Pro Asn Ser Asp Asn Ala Ile Asp Leu Lys
            100                 105                 110

Val Leu Asp Arg His Gly Asn Pro Val Leu Ala Asp Arg Leu Phe His
            115                 120                 125

Ser Gly Glu His Pro Val Tyr Thr Val Arg Thr Val Glu Gly Leu Arg
130                 135                 140

Val Thr Gly Thr Ala Asn His Pro Leu Leu Cys Leu Val Asp Val Ala
145                 150                 155                 160

Gly Val Pro Thr Leu Leu Trp Lys Leu Ile Asp Glu Ile Lys Pro Gly
                165                 170                 175

Asp Tyr Ala Val Ile Gln Arg Ser Ala Phe Ser Val Asp Cys Ala Gly
            180                 185                 190

Phe Ala Arg Gly Lys Pro Glu Phe Ala Pro Thr Thr Tyr Thr Val Gly
            195                 200                 205

Val Pro Gly Leu Val Arg Phe Leu Glu Ala His His Arg Asp Pro Asp
210                 215                 220
```

```
Ala Gln Ala Ile Ala Asp Glu Leu Thr Asp Gly Arg Phe Tyr Tyr Ala
225                 230                 235                 240

Lys Val Ala Ser Val Thr Asp Ala Gly Val Gln Pro Val Tyr Ser Leu
                245                 250                 255

Arg Val Asp Thr Ala Asp His Ala Phe Ile Thr Asn Gly Phe Val Ser
            260                 265                 270

His Ala Thr Glu Ala His His His His His
            275                 280
```

<210> SEQ ID NO 766
<211> LENGTH: 222
<212> TYPE: PRT
<213> ORGANISM: Artificial Sequence
<220> FEATURE:
<223> OTHER INFORMATION: Synthetic peptide

<400> SEQUENCE: 766

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Cys Leu Ser Tyr
65                  70                  75                  80

Glu Thr Glu Ile Leu Thr Val Glu Tyr Gly Leu Leu Pro Ile Gly Lys
                85                  90                  95

Ile Val Glu Lys Arg Ile Glu Cys Thr Val Tyr Ser Val Asp Asn Asn
            100                 105                 110

Gly Asn Ile Tyr Thr Gln Pro Val Ala Gln Trp His Asp Arg Gly Glu
        115                 120                 125

Gln Glu Val Phe Glu Tyr Cys Leu Glu Asp Gly Ser Leu Ile Arg Ala
    130                 135                 140

Thr Lys Asp His Lys Phe Met Thr Val Asp Gly Gln Met Leu Pro Ile
145                 150                 155                 160

Asp Glu Ile Phe Glu Arg Glu Leu Asp Leu Met Arg Val Asp Asn Leu
                165                 170                 175

Pro Asn Ile Lys Ile Ala Thr Arg Lys Tyr Leu Gly Lys Gln Asn Val
            180                 185                 190

Tyr Asp Ile Gly Val Glu Arg Asp His Asn Phe Ala Leu Lys Asn Gly
        195                 200                 205

Phe Ile Ala Ser Ala Ala Phe Asn His His His His His
    210                 215                 220
```

<210> SEQ ID NO 767
<211> LENGTH: 222
<212> TYPE: PRT
<213> ORGANISM: Artificial Sequence
<220> FEATURE:
<223> OTHER INFORMATION: Synthetic peptide

<400> SEQUENCE: 767

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
```

```
                20                  25                  30
Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Cys Leu Ser Tyr
 65                  70                  75                  80

Asp Thr Glu Val Leu Thr Val Glu Tyr Gly Phe Val Pro Ile Gly Glu
                85                  90                  95

Ile Val Asp Lys Gly Ile Glu Cys Ser Val Phe Ser Ile Asp Ser Asn
            100                 105                 110

Gly Ile Val Tyr Thr Gln Pro Ile Ala Gln Trp His His Arg Gly Lys
        115                 120                 125

Gln Glu Val Phe Glu Tyr Cys Leu Glu Asp Gly Ser Ile Ile Lys Ala
    130                 135                 140

Thr Lys Asp His Lys Phe Met Thr Gln Asp Gly Lys Met Leu Pro Ile
145                 150                 155                 160

Asp Glu Ile Phe Glu Gln Glu Leu Asp Leu Leu Gln Val Lys Gly Leu
                165                 170                 175

Pro Glu Ile Lys Ile Ala Ser Arg Lys Phe Leu Gly Val Glu Asn Val
            180                 185                 190

Tyr Asp Ile Gly Val Gly Arg Asp His Asn Phe Phe Val Lys Asn Gly
        195                 200                 205

Leu Ile Ala Ser Ala Ala Phe Asn His His His His His His
    210                 215                 220

<210> SEQ ID NO 768
<211> LENGTH: 224
<212> TYPE: PRT
<213> ORGANISM: Artificial Sequence
<220> FEATURE:
<223> OTHER INFORMATION: Synthetic peptide

<400> SEQUENCE: 768

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Cys Leu Ser Tyr
 65                  70                  75                  80

Asp Thr Gln Ile Leu Thr Val Glu Tyr Gly Ala Val Ala Ile Gly Glu
                85                  90                  95

Ile Val Glu Lys Gln Ile Glu Cys Thr Val Tyr Ser Val Asp Glu Asn
            100                 105                 110

Gly Tyr Val Tyr Thr Gln Pro Ile Ala Gln Trp His Asn Arg Gly Glu
        115                 120                 125

Gln Glu Val Phe Glu Tyr Leu Leu Asp Gly Ala Thr Ile Arg Ala
    130                 135                 140

Thr Lys Asp His Lys Phe Met Thr Asp Glu Asp Gln Met Leu Pro Ile
145                 150                 155                 160

Asp Gln Ile Phe Glu Gln Gly Leu Glu Leu Lys Gln Val Glu Val Leu
```

```
                    165                 170                 175
Gln Pro Val Phe Val Lys Ile Val Arg Arg Gln Ser Leu Gly Val Gln
            180                 185                 190

Asn Val Tyr Asp Ile Gly Val Glu Lys Asp His Asn Phe Cys Leu Ala
        195                 200                 205

Ser Gly Glu Ile Ala Ser Ala Ala Phe Asn His His His His His His
    210                 215                 220
```

<210> SEQ ID NO 769
<211> LENGTH: 283
<212> TYPE: PRT
<213> ORGANISM: Artificial Sequence
<220> FEATURE:
<223> OTHER INFORMATION: Synthetic peptide

<400> SEQUENCE: 769

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Cys Ile Thr Gly
65                  70                  75                  80

Asp Ala Leu Val Ala Leu Pro Glu Gly Glu Ser Val Arg Ile Ala Asp
                85                  90                  95

Ile Val Pro Gly Ala Arg Pro Asn Ser Asp Asn Ala Ile Asp Leu Lys
            100                 105                 110

Val Leu Asp Arg His Gly Asn Pro Val Leu Ala Asp Arg Leu Phe His
        115                 120                 125

Ser Gly Glu His Pro Val Tyr Thr Val Arg Thr Val Glu Gly Leu Arg
    130                 135                 140

Val Thr Gly Thr Ala Asn His Pro Leu Leu Cys Leu Val Asp Val Ala
145                 150                 155                 160

Gly Val Pro Thr Leu Leu Trp Lys Leu Ile Asp Glu Ile Lys Pro Gly
                165                 170                 175

Asp Tyr Ala Val Ile Gln Arg Ser Ala Phe Ser Val Asp Cys Ala Gly
            180                 185                 190

Phe Ala Arg Gly Lys Pro Glu Phe Ala Pro Thr Thr Tyr Thr Val Gly
        195                 200                 205

Val Pro Gly Leu Val Arg Phe Leu Glu Ala His His Arg Asp Pro Asp
    210                 215                 220

Ala Gln Ala Ile Ala Asp Glu Leu Thr Asp Gly Arg Phe Tyr Tyr Ala
225                 230                 235                 240

Lys Val Ala Ser Val Thr Asp Ala Gly Val Gln Pro Val Tyr Ser Leu
                245                 250                 255

Arg Val Asp Thr Ala Asp His Ala Phe Ile Thr Asn Gly Phe Val Ser
            260                 265                 270

His Ala Ala Glu Ala His His His His His His
        275                 280
```

<210> SEQ ID NO 770
<211> LENGTH: 201
<212> TYPE: PRT

<213> ORGANISM: Artificial Sequence
<220> FEATURE:
<223> OTHER INFORMATION: Synthetic peptide

<400> SEQUENCE: 770

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Cys Leu Ser Tyr Asp Thr Glu Val Leu
50                  55                  60

Thr Val Glu Tyr Gly Phe Val Pro Ile Gly Glu Ile Val Asp Lys Gly
65                  70                  75                  80

Ile Glu Cys Ser Val Phe Ser Ile Asp Ser Asn Gly Ile Val Tyr Thr
                85                  90                  95

Gln Pro Ile Ala Gln Trp His His Arg Gly Lys Gln Glu Val Phe Glu
            100                 105                 110

Tyr Cys Leu Glu Asp Gly Ser Ile Ile Lys Ala Thr Lys Asp His Lys
        115                 120                 125

Phe Met Thr Gln Asp Gly Lys Met Leu Pro Ile Asp Glu Ile Phe Glu
130                 135                 140

Gln Glu Leu Asp Leu Leu Gln Val Lys Gly Leu Pro Glu Ile Lys Ile
145                 150                 155                 160

Ala Ser Arg Lys Phe Leu Gly Val Glu Asn Val Tyr Asp Ile Gly Val
                165                 170                 175

Gly Arg Asp His Asn Phe Phe Val Lys Asn Gly Leu Ile Ala Ser Ala
            180                 185                 190

Ala Phe Asn His His His His His His
        195                 200
```

<210> SEQ ID NO 771
<211> LENGTH: 202
<212> TYPE: PRT
<213> ORGANISM: Artificial Sequence
<220> FEATURE:
<223> OTHER INFORMATION: Synthetic peptide

<400> SEQUENCE: 771

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Gly Cys Leu Ser Tyr Asp Thr Glu Val
50                  55                  60

Leu Thr Val Glu Tyr Gly Phe Val Pro Ile Gly Glu Ile Val Asp Lys
65                  70                  75                  80

Gly Ile Glu Cys Ser Val Phe Ser Ile Asp Ser Asn Gly Ile Val Tyr
                85                  90                  95

Thr Gln Pro Ile Ala Gln Trp His His Arg Gly Lys Gln Glu Val Phe
            100                 105                 110

Glu Tyr Cys Leu Glu Asp Gly Ser Ile Ile Lys Ala Thr Lys Asp His
        115                 120                 125
```

```
Lys Phe Met Thr Gln Asp Gly Lys Met Leu Pro Ile Asp Glu Ile Phe
        130                 135                 140

Glu Gln Glu Leu Asp Leu Leu Gln Val Lys Gly Leu Pro Glu Ile Lys
145                 150                 155                 160

Ile Ala Ser Arg Lys Phe Leu Gly Val Glu Asn Val Tyr Asp Ile Gly
                165                 170                 175

Val Gly Arg Asp His Asn Phe Val Lys Asn Gly Leu Ile Ala Ser
                180                 185                 190

Ala Ala Phe Asn His His His His His His
        195                 200

<210> SEQ ID NO 772
<211> LENGTH: 203
<212> TYPE: PRT
<213> ORGANISM: Artificial Sequence
<220> FEATURE:
<223> OTHER INFORMATION: Synthetic peptide

<400> SEQUENCE: 772

Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
                20                  25                  30

Asp Gln Asn Trp Tyr Lys Ala Glu Leu Asn Gly Lys Asp Gly Phe Ile
            35                  40                  45

Pro Lys Asn Tyr Ile Glu Met Cys Leu Ser Tyr Asp Thr Gln Ile Leu
        50                  55                  60

Thr Val Glu Tyr Gly Ala Val Ala Ile Gly Glu Ile Val Glu Lys Gln
65                  70                  75                  80

Ile Glu Cys Thr Val Tyr Ser Val Asp Glu Asn Gly Tyr Val Tyr Thr
                85                  90                  95

Gln Pro Ile Ala Gln Trp His Asn Arg Gly Glu Gln Glu Val Phe Glu
            100                 105                 110

Tyr Leu Leu Glu Asp Gly Ala Thr Ile Arg Ala Thr Lys Asp His Lys
        115                 120                 125

Phe Met Thr Asp Glu Asp Gln Met Leu Pro Ile Asp Gln Ile Phe Glu
    130                 135                 140

Gln Gly Leu Glu Leu Lys Gln Val Glu Val Leu Gln Pro Val Phe Val
145                 150                 155                 160

Lys Ile Val Arg Arg Gln Ser Leu Gly Val Gln Asn Val Tyr Asp Ile
                165                 170                 175

Gly Val Glu Lys Asp His Asn Phe Cys Leu Ala Ser Gly Glu Ile Ala
                180                 185                 190

Ser Ala Ala Phe Asn His His His His His His
        195                 200

<210> SEQ ID NO 773
<211> LENGTH: 243
<212> TYPE: PRT
<213> ORGANISM: Artificial Sequence
<220> FEATURE:
<223> OTHER INFORMATION: Synthetic peptide

<400> SEQUENCE: 773

Met Leu Glu Lys His Ser Trp Tyr His Gly Pro Val Ser Arg Asn Ala
1               5                   10                  15

Ala Glu Tyr Leu Leu Ser Ser Gly Ile Asn Gly Ser Phe Leu Val Arg
                20                  25                  30
```

Glu Ser Glu Ser Ser Pro Gly Gln Arg Ser Ile Ser Leu Arg Tyr Glu
                35                  40                  45

Gly Arg Val Tyr His Tyr Arg Ile Asn Thr Ala Ser Asp Gly Lys Leu
 50                  55                  60

Tyr Val Ser Ser Glu Ser Arg Phe Asn Thr Leu Ala Glu Leu Val His
 65                  70                  75                  80

His His Ser Thr Val Ala Asp Gly Leu Ile Thr Thr Leu His Tyr Pro
                 85                  90                  95

Ala Cys Leu Ser Tyr Asp Thr Glu Val Leu Thr Val Glu Tyr Gly Phe
                100                 105                 110

Val Pro Ile Gly Glu Ile Val Asp Lys Gly Ile Glu Cys Ser Val Phe
                115                 120                 125

Ser Ile Asp Ser Asn Gly Ile Val Tyr Thr Gln Pro Ile Ala Gln Trp
    130                 135                 140

His His Arg Gly Lys Gln Glu Val Phe Glu Tyr Cys Leu Glu Asp Gly
145                 150                 155                 160

Ser Ile Ile Lys Ala Thr Lys Asp His Lys Phe Met Thr Gln Asp Gly
                165                 170                 175

Lys Met Leu Pro Ile Asp Glu Ile Phe Glu Gln Glu Leu Asp Leu Leu
                180                 185                 190

Gln Val Lys Gly Leu Pro Glu Ile Lys Ile Ala Ser Arg Lys Phe Leu
                195                 200                 205

Gly Val Glu Asn Val Tyr Asp Ile Gly Val Gly Arg Asp His Asn Phe
210                 215                 220

Phe Val Lys Asn Gly Leu Ile Ala Ser Ala Ala Phe Asn His His His
225                 230                 235                 240

His His His

<210> SEQ ID NO 774
<211> LENGTH: 385
<212> TYPE: PRT
<213> ORGANISM: Artificial Sequence
<220> FEATURE:
<223> OTHER INFORMATION: Synthetic peptide

<400> SEQUENCE: 774

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
                35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Cys
225                 230                 235                 240

Leu Ser Tyr Asp Thr Glu Val Leu Thr Val Glu Tyr Gly Phe Val Pro
            245                 250                 255

Ile Gly Glu Ile Val Asp Lys Gly Ile Glu Cys Ser Val Phe Ser Ile
            260                 265                 270

Asp Ser Asn Gly Ile Val Tyr Thr Gln Pro Ile Ala Gln Trp His His
        275                 280                 285

Arg Gly Lys Gln Glu Val Phe Glu Tyr Cys Leu Glu Asp Gly Ser Ile
290                 295                 300

Ile Lys Ala Thr Lys Asp His Lys Phe Met Thr Gln Asp Gly Lys Met
305                 310                 315                 320

Leu Pro Ile Asp Glu Ile Phe Glu Gln Glu Leu Asp Leu Leu Gln Val
            325                 330                 335

Lys Gly Leu Pro Glu Ile Lys Ile Ala Ser Arg Lys Phe Leu Gly Val
        340                 345                 350

Glu Asn Val Tyr Asp Ile Gly Val Gly Arg Asp His Asn Phe Phe Val
        355                 360                 365

Lys Asn Gly Leu Ile Ala Ser Ala Phe Asn His His His His His His
        370                 375                 380

His
385

<210> SEQ ID NO 775
<211> LENGTH: 505
<212> TYPE: PRT
<213> ORGANISM: Artificial Sequence
<220> FEATURE:
<223> OTHER INFORMATION: Synthetic peptide

<400> SEQUENCE: 775

Met Val Asn Pro Gly Thr Lys Ser Lys Leu Pro Lys Pro Val Gln Asp
1               5                   10                  15

Leu Ile Lys Met Ile Phe Asp Val Glu Ser Met Lys Lys Ala Met Val
                20                  25                  30

Glu Tyr Glu Ile Asp Leu Gln Lys Met Pro Leu Gly Lys Leu Ser Lys
            35                  40                  45

Arg Gln Ile Gln Ala Ala Tyr Ser Ile Leu Ser Glu Val Gln Gln Ala
        50                  55                  60

Val Ser Gln Gly Ser Ser Asp Ser Gln Ile Leu Asp Leu Ser Asn Arg
65                  70                  75                  80

Phe Tyr Thr Leu Ile Pro His Asp Phe Gly Met Lys Lys Pro Pro Leu
                85                  90                  95

Leu Asn Asn Ala Asp Ser Val Gln Ala Lys Ala Glu Met Leu Asp Asn
                100                 105                 110

```
Leu Leu Asp Ile Glu Val Ala Tyr Ser Leu Leu Arg Gly Gly Ser Asp
            115                 120                 125

Asp Ser Ser Lys Asp Pro Ile Asp Val Asn Tyr Glu Lys Leu Lys Thr
130                 135                 140

Asp Ile Lys Val Val Asp Arg Asp Ser Glu Glu Ala Glu Ile Ile Arg
145                 150                 155                 160

Lys Tyr Val Lys Asn Thr His Ala Thr Thr His Asn Ala Tyr Asp Leu
                165                 170                 175

Glu Val Ile Asp Ile Phe Lys Ile Glu Arg Glu Gly Glu Cys Gln Arg
            180                 185                 190

Tyr Lys Pro Phe Lys Gln Leu His Asn Arg Arg Leu Leu Trp His Gly
        195                 200                 205

Ser Arg Thr Thr Asn Phe Ala Gly Ile Leu Ser Gln Gly Leu Arg Ile
210                 215                 220

Ala Pro Pro Glu Ala Pro Val Thr Gly Tyr Met Phe Gly Lys Gly Ile
225                 230                 235                 240

Tyr Phe Ala Asp Met Val Ser Lys Ser Ala Asn Tyr Cys His Thr Ser
                245                 250                 255

Gln Gly Asp Pro Ile Gly Leu Ile Leu Leu Gly Glu Val Ala Leu Gly
            260                 265                 270

Asn Met Tyr Glu Leu Lys His Ala Ser His Ile Ser Lys Leu Pro Lys
275                 280                 285

Gly Lys His Ser Val Lys Gly Leu Gly Lys Thr Thr Pro Asp Pro Ser
290                 295                 300

Ala Asn Ile Ser Leu Asp Gly Val Asp Val Pro Leu Gly Thr Gly Ile
305                 310                 315                 320

Ser Ser Gly Val Asn Asp Thr Ser Leu Leu Tyr Asn Glu Tyr Ile Val
                325                 330                 335

Tyr Asp Ile Ala Gln Val Asn Leu Lys Tyr Leu Leu Lys Leu Lys Phe
            340                 345                 350

Asn Phe Lys Thr Ser Leu Trp Cys Leu Ser Tyr Asp Thr Glu Val Leu
        355                 360                 365

Thr Val Glu Tyr Gly Phe Val Pro Ile Gly Glu Ile Val Asp Lys Gly
370                 375                 380

Ile Glu Cys Ser Val Phe Ser Ile Asp Ser Asn Gly Ile Val Tyr Thr
385                 390                 395                 400

Gln Pro Ile Ala Gln Trp His His Arg Gly Lys Gln Glu Val Phe Glu
                405                 410                 415

Tyr Cys Leu Glu Asp Gly Ser Ile Ile Lys Ala Thr Lys Asp His Lys
            420                 425                 430

Phe Met Thr Gln Asp Gly Lys Met Leu Pro Ile Asp Glu Ile Phe Glu
        435                 440                 445

Gln Glu Leu Asp Leu Leu Gln Val Lys Gly Leu Pro Glu Ile Lys Ile
450                 455                 460

Ala Ser Arg Lys Phe Leu Gly Val Glu Asn Val Tyr Asp Ile Gly Val
465                 470                 475                 480

Gly Arg Asp His Asn Phe Phe Val Lys Asn Gly Leu Ile Ala Ser Ala
                485                 490                 495

Ala Phe Asn His His His His His His
            500                 505

<210> SEQ ID NO 776
<211> LENGTH: 39
<212> TYPE: PRT
```

```
<213> ORGANISM: Nostoc punctiforme

<400> SEQUENCE: 776

Met Ile Lys Ile Ala Thr Arg Lys Tyr Leu Gly Lys Gln Asn Val Tyr
1               5                   10                  15

Asp Ile Gly Val Glu Arg Asp His Asn Asp Ala Leu Lys Asn Gly Phe
            20                  25                  30

Ile Ala Ser Asn Cys Phe Asn
        35

<210> SEQ ID NO 777
<211> LENGTH: 43
<212> TYPE: PRT
<213> ORGANISM: Nostoc punctiforme

<400> SEQUENCE: 777

Met Ile Lys Ile Ala Thr Arg Lys Tyr Leu Gly Lys Gln Asn Val Tyr
1               5                   10                  15

Asp Ile Gly Val Glu Arg Asp His Asn Asp Ala Leu Lys Asn Gly Phe
            20                  25                  30

Ile Ala Ser Ala Ala Phe Asn Ser Gly Gly Cys
        35                  40
```

SPLIT INTEINS, CONJUGATES AND USES THEREOF

CROSS REFERENCE TO RELATED APPLICATIONS

This application is a continuation application of U.S. patent application Ser. No. 16/690,213, filed Nov. 21, 2019, now U.S. Pat. No. 11,161,899, which is a continuation of U.S. patent application Ser. No. 15/809,440, filed Nov. 10, 2017, now U.S. Pat. No. 10,526,401, which is a continuation application of U.S. patent application Ser. No. 14/411,702, filed Dec. 29, 2014, now abandoned, which is a U.S. National Stage application of International Patent Application No. PCT/US13/47235, filed Jun. 24, 2013, and which claims the benefit of priority to U.S. Provisional Patent Application No. 61/665,215, filed, Jun. 27, 2012. The entire contents and disclosure of these patent applications are incorporated herein by reference in its entirety.

STATEMENT OF U.S. GOVERNMENT SUPPORT

This invention was made with U.S. government support under Grant No. GM086868 awarded by the National Institutes of Health (NIH). The U.S. government has certain rights in the invention.

This application contains, as a separate part of disclosure, a Sequence Listing in computer-readable form (filename: 47046A_SeqListing.txt; 547,838 bytes—ASCII text file—created Jun. 20, 2013) which is inconcorporated by reference in its entirety.

BACKGROUND

Protein splicing is a post-translational process catalyzed by a family of proteins known as inteins.(1) During this process, an intein domain catalyzes its own excision from a larger precursor protein and simultaneously ligates the two flanking polypeptide sequences (exteins) together. While most inteins catalyze splicing in cis, a small subset of these proteins exist as naturally fragmented domains that are separately expressed but rapidly associate and catalyze splicing in trans. Given their capacity to make and break polypeptide bonds (inteins can be considered protein ligases), both cis and trans-splicing inteins have found widespread use as chemical biological tools.(2)

Despite the growing use of inteins in chemical biology, their practical utility has been constrained by two common characteristics of the family, namely (i) slow kinetics and (ii) context dependent efficiency with respect to the immediate flanking extein sequences.(3,4) Recently, a split intein from the cyanobacterium *Nostoc punctiforme* (Npu) was shown to catalyze protein trans-splicing on the order of a minute, rather than hours like most cis- or trans-splicing inteins.(5) Furthermore, this intein was slightly more tolerant of sequence variation at the critical +2 C-extein residue than other inteins.(6)

Thus, a need exists for more robust and more efficient split inteins for use in a variety of protein purification and protein modification applications.

SUMMARY

Disclosed are split intein N- and C-fragments, variants thereof, and methods of using these split inteins in polypeptide purification and modification.

Thus, provided herein are fusion proteins of a polypeptide and a split intein N-fragment, or variant thereof, as described below in greater detail. Also provided are complexes of the fusion protein and a split intein C-fragment or variant thereof as described in detail below. The complex of the fusion protein and C-fragment or variant thereof can be via a covalent interaction between the fusion protein and C-fragment or variant or via a non-covalent interaction (e.g., ionic, H-bonding, and/or van der Waals interaction).

Further provided herein are split intein C-fragments or variants thereof. In some cases the split intein C-fragment further comprises a linker, such as a peptide linker, or other linkers as described below in detail. A specific peptide linker contemplated is -SGGC (SEQ ID NO: 705) attached to any of the split intein C-fragments described below. The linker can be tailored so as to allow for attachment of a split intein C-fragment of interest to a support, e.g., a bead, a resin, a slide, a particle.

Also provided herein are methods using the split intein N- and C-fragments, or variants thereof, as described in detail below. More particularly, provided herein are methods comprising (a) contacting (1) a fusion protein comprising a polypeptide and a split intein N-fragment, or a variant thereof, as described in detail below and (2) a split intein C-fragment or a variant thereof, as described in detail below; wherein contacting is performed under conditions that permit binding of the split intein N-fragment to the split intein C-fragment to form an intein intermediate; and (b) contacting the intein intermediate with a nucleophile to form a conjugate of the protein and the nucleophile. In various embodiments, the split intein C-fragment, or variant thereof, is bound to a support. In some embodiments, the support is a bead, a resin, a particle or a slide. It will be appreciated that selection of the N-fragment and C-fragment can be from the same wild type split intein (e.g., both from Npu, or a variant of either the N- or C-fragment as discussed in great detail below), or alternatively can be selected from different wild type split inteins or the consensus split intein sequences discussed below, as it has been discovered that the affinity of a N-fragment for a different C-fragment (e.g., Npu N-fragment or variant thereof with Ssp C-fragment or variant thereof) still maintains sufficient binding affinity for use in the disclosed methods. Moreover, such a finding allows for a single C-fragment or variant thereof bound to a support to be useful in purification and/or modification methods disclosed herein with a fusion protein wherein the N-fragment is any of the ones disclosed herein, or a variant thereof. Thus, one can select an N-fragment that has advantages for any individual polypeptide of interest, e.g., one that expresses better than others disclosed herein.

The fusion protein can be in a whole cell lysate or secreted from a cell (e.g., a mammalian cell) and in a cell supernatant. In some cases, the polypeptide of the fusion protein is an antibody, e.g., an IgG antibody. In some embodiments, the N-fragment is fused to one or both of the heavy chains of the antibody. In some embodiments, the N-fragment is fused to one or both of the light chains of the antibody. The methods disclosed herein can further comprise washing the intein intermediate (prior to contact with the nucleophile) to remove the cell lysate or cell supernatant, for example.

The methods disclosed herein can further comprise isolating the resulting conjugate of the polypeptide and nucleophile. Thus, the methods disclosed herein can be useful as an efficient purification for polypeptides prepared by recombinant protein methods.

The nucleophile can be a thiol to form a conjugate that is an α-thioester of the polypeptide. In some cases, the resulting α-thioester can be further modified by contacting with a second nucleophile, employing the well known α-thioester chemistry for protein modification. In some cases, the methods disclosed herein can provide conjugates of the polypeptide, which in some cases is an antibody (e.g., an IgG antibody), and a nucleophile (e.g., a drug, a polymer, an oligonucleotide).

BRIEF DESCRIPTIONS OF THE DRAWINGS

FIG. 1 shows trans-splicing of split DnaE inteins. (a) Scheme depicting protein trans-splicing of the KanR protein with a variable local C-extein sequence. (b) In vivo relative trans-splicing efficiencies at 30° C. with the endogenous "CFN" C-extein sequence and exogenous "CGN", "CEN", and "CRN" sequences. $IC_{50}$ values (±SE, n=3-4) are normalized relative to that of intact KanR proteins with the appropriate C-extein tri-peptide.

FIG. 2 shows in vitro half-lives of trans-splicing reactions. Indicated split intein pairs fused to model exteins Ub or SUMO (Ub-$Int^N$ and $Int^C$-SUMO) were mixed at either 30° C. or 37° C., and the formation of products was monitored over time by gel electrophoresis. (a) Half-lives were extracted from the reaction progress curves fit to a standard first-order rate equation (±SE, n=3). Representative coomassie-stained SDS-PAGE gels showing (b) fast Ava splicing at 37° C. and (c) inefficient Ssp splicing at 37° C.

FIG. 3 shows sequence-activity relationships in split DnaE inteins. (a) Inteins in order of in vivo splicing activity with selected slices from the corresponding multiple sequence alignment. (b) Rendering of the Npu structure highlighting the proximity of position 120 to the terminal catalytic residues C1 and N137. (c) In vivo analysis of the C120G mutation in the Aha intein (±SD, n=3). (d) Rendering of the Npu structure highlighting key catalytic residues (sticks) and important non-catalytic positions (spheres) that modulate Ssp activity. (e) In vivo analysis of Ssp-to-Npu point mutations that improve Ssp activity (±SD, n=4). Note that all residue numberings correspond to the relevant positions on Npu as defined by the NMR structure (PDB: 2KEQ).(21)

FIG. 4 shows engineered versions of ultrafast DnaE inteins support efficient expressed protein ligation. (a) Scheme depicting the formation of the linear thioester intermediate and its use to generate a protein α-thioester for EPL. (b) Coomassie-stained SDS-PAGE gel depicting efficient MESNa thiolysis of ubiquitin from a fused AvaDnaE intein to yield the Ub-MES thioester, 4. (c) Fluorescent SDS-PAGE gels showing the formation of the Ub-CGK (Fluorescein) ligated product (6) from one-pot thiolysis and native chemical ligation reactions using the inteins indicated. (d) Reverse phase HPLC chromatographs showing pH dependence of the relative populations of precursor amide (1) and linear thioester (2).

FIG. 5 shows sequence alignments of split DnaE inteins. Numbering follows that of Npu as assigned for the NMR structure (PDB 2KEQ). Critical catalytic residues are marked with an asterisk. Sequence identifiers for the N-intein sequences depicted in the figure are as follows: Npu (SEQ ID NO:1), Ssp (SEQ ID NO:2), Aha (SEQ ID NO:3), Aov (SEQ ID NO:4), Asp (SEQ ID NO: 5), Ava (SEQ ID NO:6), Cra (CS505) (SEQ ID NO:7), Csp (CCY0110) (SEQ ID NO:8), Csp (PCC8801) (SEQ ID NO:9), Cwa (SEQ ID NO;10), Maer (NIES843) (SEQ ID NO: 11), Mcht (PCC7420) (SEQ ID NO:12), Oli (SEQ ID NO:13), Sel (PC7942) (SEQ ID NO:14), Ssp (PCC7002) (SEQ ID NO:15), Tel (SEQ ID NO:16), Ter (SEQ ID NO:17) and Tvu (SEQ ID NO:18). Sequence identifiers for the C-intein sequences depicted in the figure are as follows: Npu (SEQ ID NO:39), Ssp (SEQ ID NO:40), Aha (SEQ ID NO: 41), Aov (SEQ ID NO:42), Asp (SEQ ID NO: 43), Ava (SEQ ID NO:44), Cra (CS505) (SEQ ID NO:45), Csp (CCY0110) (SEQ ID NO:46), Csp (PCC8801) (SEQ ID NO:47), Cwa (SEQ ID NO:48), Maer (NIES843) (SEQ ID NO:49), Mcht (PCC7420) (SEQ ID NO:50), Oli (SEQ ID NO:51), Sel (PC7942) (SEQ ID NO:52), Ssp (PCC7002) (SEQ ID NO:53), Tel (SEQ ID NO:54), Ter (SEQ ID NO:55) and Tvu (SEQ ID NO:56).

FIG. 6 shows sequence logos for high- and low-activity inteins. Inteins are ranked based on in vivo activity with a "CFN" C-extein sequence. The high and low activity inteins are distinguished based on a cut-off $IC_{50}$ value of 350 μg/mL of kanamycin, and the Aha intein is included in the high-activity set, given that the $C^{120}G$ mutation dramatically restores high activity.

FIG. 7 shows purification of C-terminal α-thioesters using split-inteins. A) Scheme of the split-intein based purification of protein C-terminal α-thioesters. B) Sequence of WT $Npu^C$ and its mutant $Npu^C$-AA having a linker to immobilize it onto a solid support (underlined). For the thiolysis experiments in solution the C-terminal Cys residue was previously alkylated with iodoacetamide.

FIG. 8 shows Purification of soluble protein α-thioesters using the $Npu^C$-AA affinity column. A) Scheme of the purification strategy using split Npu DnaE intein. B) Purification of Ub-thioester (Ub-COSR) from cell lysates. C) Purification of MBP-thioester (MBP-COSR) from cell lysates. Both purifications were monitored by SDSPAGE analysis stained with Coomassie (top) or Western Blot using an α-His antibody.

FIG. 9 shows RP-HPLC and MS analysis of Ub and MBP α-thioesters. A) RP-HPLC (top) and MS (bottom) analysis of Ub-COSR eluted from the $Npu^C$-AA column. B) RP-HPLC (top) and MS (bottom) analysis of MBP-COSR eluted from the $Npu^C$-AA column.

FIG. 10 shows the effect of the −1 residue on the efficiency of the on-resin thiolysis. 20 different Ub-$Npu^N$ proteins were expressed containing each of the 20 proteinogenic amino acids at the C-terminus of Ub (−1 residue) and purified over $Npu^C$-AA columns. Cleavage yields from the $Npu^C$-AA column were estimated by gel elctrophoresis and amounts of thioester versus side reactions (mainly hydrolysis) were determined by RP-HPLC and MS analysis.

FIG. 11 shows purification of H2B(1-116)-α-thioester under denaturing conditions. A) SDSPAGE analysis of the purification of H2B(1-116) α-thioester over the $Npu^C$-AA column in the presence of 3 M urea. RP-HPLC (B) and MS (C) analysis of E1 from panel A confirmed the presence of the desired H2B thioester.

FIG. 12 shows purification of αDEC thioesters expressed in 293T cells using the split-intein column. A) Expression levels of αDEC fused to different inteins in 293T cells. B) Purification of αDEC α-thioester through the $Npu^C$-AA affinity column. C) Expressed Protein Ligation (EPL) of αDEC-thioester with an N-terminal Cys containing fluorescent peptide.

FIG. 13 shows EPL directly using $Int^C$-column eluted thioesters. RP-HPLC (30-73% B gradient, 214 nm and 440 nm detection) and MS analysis of the reactions between the H-CGK(Fl)-$NH_2$ peptide and MBP (A) and PHPT1 (B) MES thioesters, purified from E. coli using the $Int^C$-column.

FIG. 14 shows a one-pot purification/ligation experiment of ubiquitin to the H-CGK(Fluorescein)-$NH_2$ peptide (CGK (Fl)). Ub-$Npu^N$ from E. coli cell lysates was bound to the Int$^C$-column, and after removal of contaminants through extensive washes, intein cleavage and ligation were triggered by addition of 200 mM MES and 1 mM CGK(Fl) peptide. Coomassie stained SDS-PAGE analysis and in gel fluorescence of the purification/ligation (left). RP-HPLC (detection at 214 and 440 nm) and ESI-TOF MS (right) of the eluted fractions confirms the desired ligated protein was obtained in one step directly from cell lysates with a ligation yield close to 95% (quantified by RP-HPLC).

FIG. 15 shows the semi-synthesis of H2B-K120Ac under denaturing conditions. A) Coomassie stained SDS-PAGE analysis of H2B(1-116) α-thioester generation in the presence of 2 M urea (sup: cell lysate supernatant, trit: 1% triton wash of the inclusion bodies, inp: solubilized inclusion bodies used as input for the Int$^C$-column). E1-E6 were pooled, concentrated to 150 µM and ligated to the peptide H-CVTK(Ac)YTSAK-OH at 1 mM for 3 h at r.t. B) RP-HPLC (left) of the ligation reaction mixture and MS (right) of the ligated H2B-K120Ac product.

FIG. 16 shows the characterization of αDEC205 ligated to the H-CGK(Fluorescein)-NH2 peptide (CGK(Fl)). Elution fractions from the Npu$^C$-column containing αDEC205-MES thioester were concentrated to 20 µM and ligated to the CGK(Fl) fluorescent peptide at 1 mM for 48 h at r.t. A) ESI-TOF MS analysis of degycosylated and fully reduced HC after ligation, showing 75% of the HC are labeled. Expected mass for ligation product=50221.2 Da. Free HC=49575.0 Da. B) SEC-MALS analysis of the ligated antibody showing that it retains its tetrameric structure after thiolysis and ligation (MW=151 kDa, MW calc=148 kDa). C) Binding of αDEC205-CGK(Fl) to the DEC205 receptor. Dose dependent binding of αDEC205-CGK(Fl) (left) or a control α-DEC205 antibody (right) to CHO cells expressing the mouse DEC205 receptor monitored by flow cytometry using a PE labeled α-mouse IgG Binding to control CHO/NEO cells, which don't express the receptor is shown in gray.

FIG. 17 shows purification of αDEC thioesters expressed in CHO cells using a split-intein column. Top) Coomassie stained SDSPAGE gel of the purification of αDEC-MES thioester from CHO cells using a Npu$^C$-column. Bottom) Western blot analysis of the same purification.

DETAILED DESCRIPTION

Of the roughly 600 inteins currently catalogued, (7) less than 5% are split inteins, mostly from a family known as the cyanobacterial split DnaE inteins (8). Surprisingly, only six of these, including Npu, have been experimentally analyzed to any extent, (6,9,10) and only Npu and its widely-studied, low-efficiency ortholog from *Synechocystis* species PCC6803 (Ssp) have been rigorously characterized in vitro. (5,11)

Figure 1:
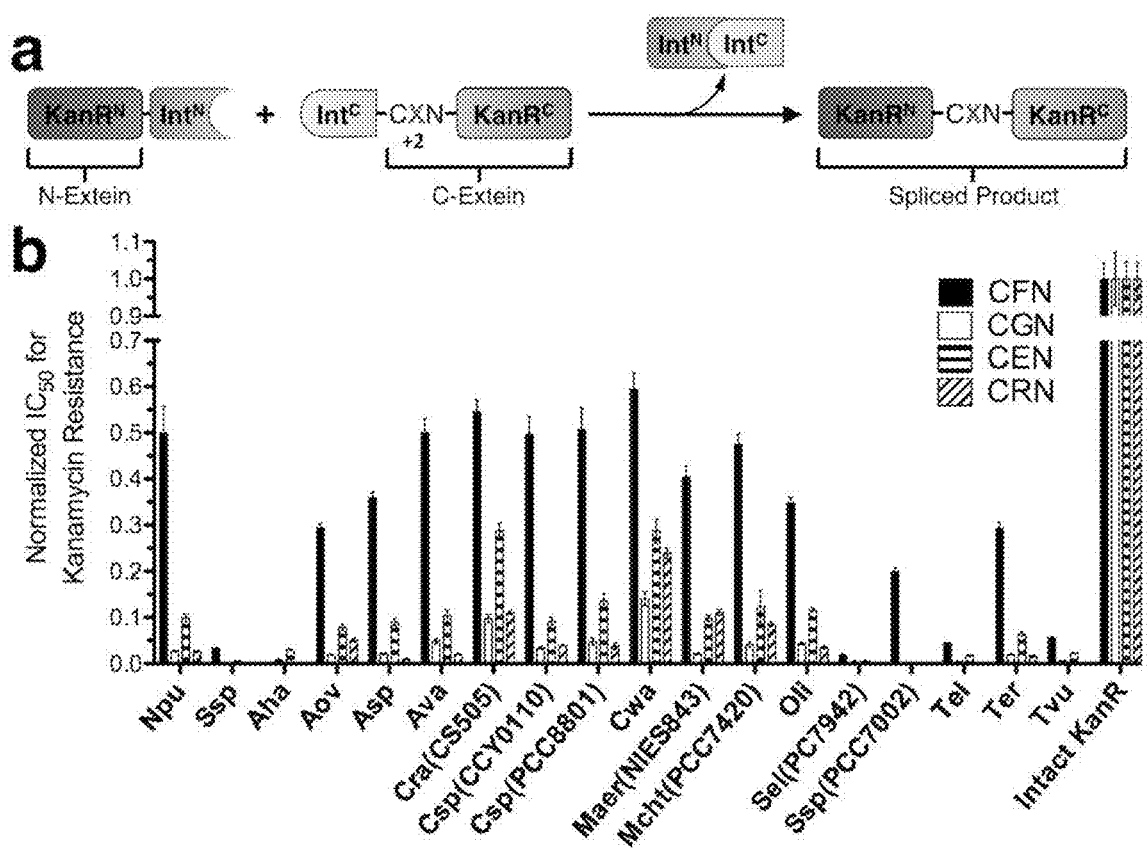

A rapid survey of 18 split DnaE inteins was performed using an in vivo screening method to accurately compare the efficiencies of split inteins(12,13) In this assay, the two fragments of a split intein are co-expressed in *E. coli* as fusions to a fragmented aminoglycoside phosphotransferase (KanR) enzyme. Upon trans-splicing, the active enzyme is assembled, and the bacteria become resistant to the antibiotic kanamycin (FIG. 1a). More active inteins confer greater kanamycin resistance and thus have a higher IC$_{50}$ value for bacterial growth as a function of kanamycin concentration. This assay can be carried out in the background of varying local C-extein sequences without significantly perturbing the dynamic range. Since all DnaE inteins splice the same local extein sequences in their endogenous context, this screen was originally carried out in a wild-type C-extein background (CFN) within the KanR enzyme. As expected, bacteria expressing the Npu intein had a high relative IC$_{50}$, whereas clones expressing Ssp showed poor resistance to kanamycin. Remarkably, more than half of the DnaE inteins showed splicing efficiency comparable to Npu in vivo at 30° C. (FIG. 1b).

Figure 2:
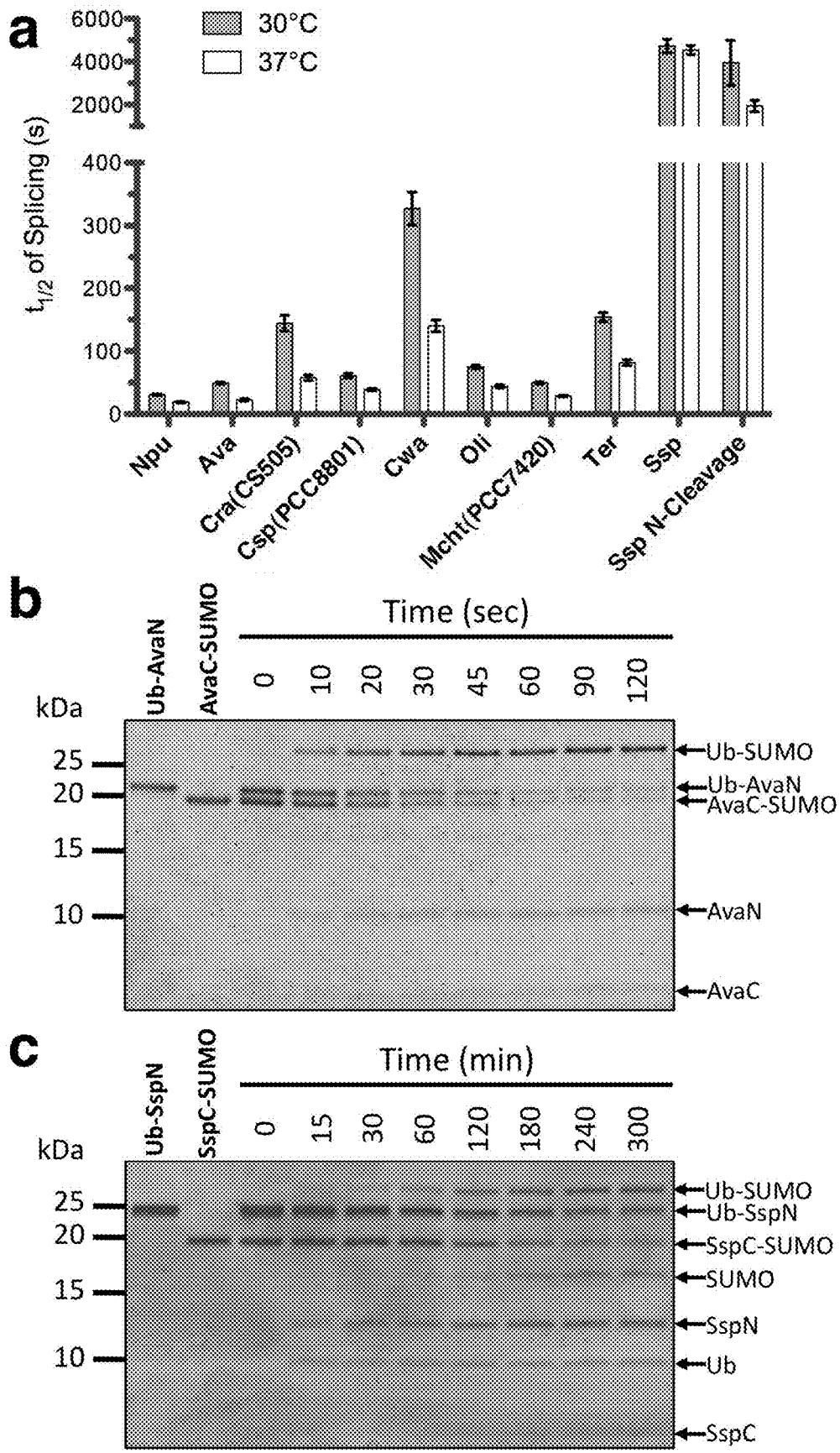

To confirm that the high IC$_{50}$ values observed in vivo reflected rapid trans-splicing, a series of kinetic studies were performed under standardized conditions in vitro. For this, individually expressed and purified split DnaE intein fragments fused to model N- and C-extein domains, ubiquitin and SUMO were made. The endogenous local extein residues were preserved as linkers between the extein domains and intein fragments to recapitulate a wild-type-like splicing context. Cognate intein fragments were mixed at 1 µM, and the formation of the Ub-SUMO spliced product at 30° C. and 37° C. was monitored by gel electrophoresis. These assays validated that the new inteins with high-activity in vivo could catalyze trans-splicing in vitro in tens of seconds, substantially faster than Ssp (FIG. 2a). Interestingly, all of the inteins analyzed except Ssp showed increased splicing rates at 37° C. Furthermore, all of the fast-splicing inteins showed low-to-undetectable levels of side reactions (FIG. 2b), again in contrast to Ssp (FIG. 2c).

The tolerance of the split inteins to C-extein sequence variation was investigated. Previously, the sensitivity of DnaE inteins was noted to changes at the +2 position in the C-extein.(6,12) Thus, all the split DnaE inteins were analyzed in the presence of a +2 glycine (CGN), glutamic acid (CEN), or arginine (CRN) in the in vivo screening assay (FIG. 1b). Like Npu and Ssp, most of the inteins showed a dramatic decrease in activity in the presence of all three +2 mutations. Of the tested amino acids, glutamic acid was tolerated best for every intein, suggesting a conserved mechanism for accommodating a negative charge at this position. To more accurately assess the magnitude of the effect of C-extein mutations on trans-splicing, the Npu, Cra(CS505), and Cwa inteins were analyzed in vitro in the presence of a +2 glycine. All three of these reactions were characterized by rapid accumulation of thioester intermediates, which slowly resolved over tens of minutes into the spliced product and the N-extein cleavage product. Consistent with previously reported observations, these data indicate that split DnaE inteins require steric bulk at the +2 position for branched intermediate resolution and efficient splicing.(12) It is noteworthy that the Cra(CS505) and Cwa inteins showed greater C-extein promiscuity in vivo, while Ssp(PCC7002) did not tolerate any of the mutations tested. This demonstrates that subtle sequence variation between split inteins can afford differential promiscuity. Thus, this property may be further optimized through directed evolution(12) or rational design.

Figure 3:
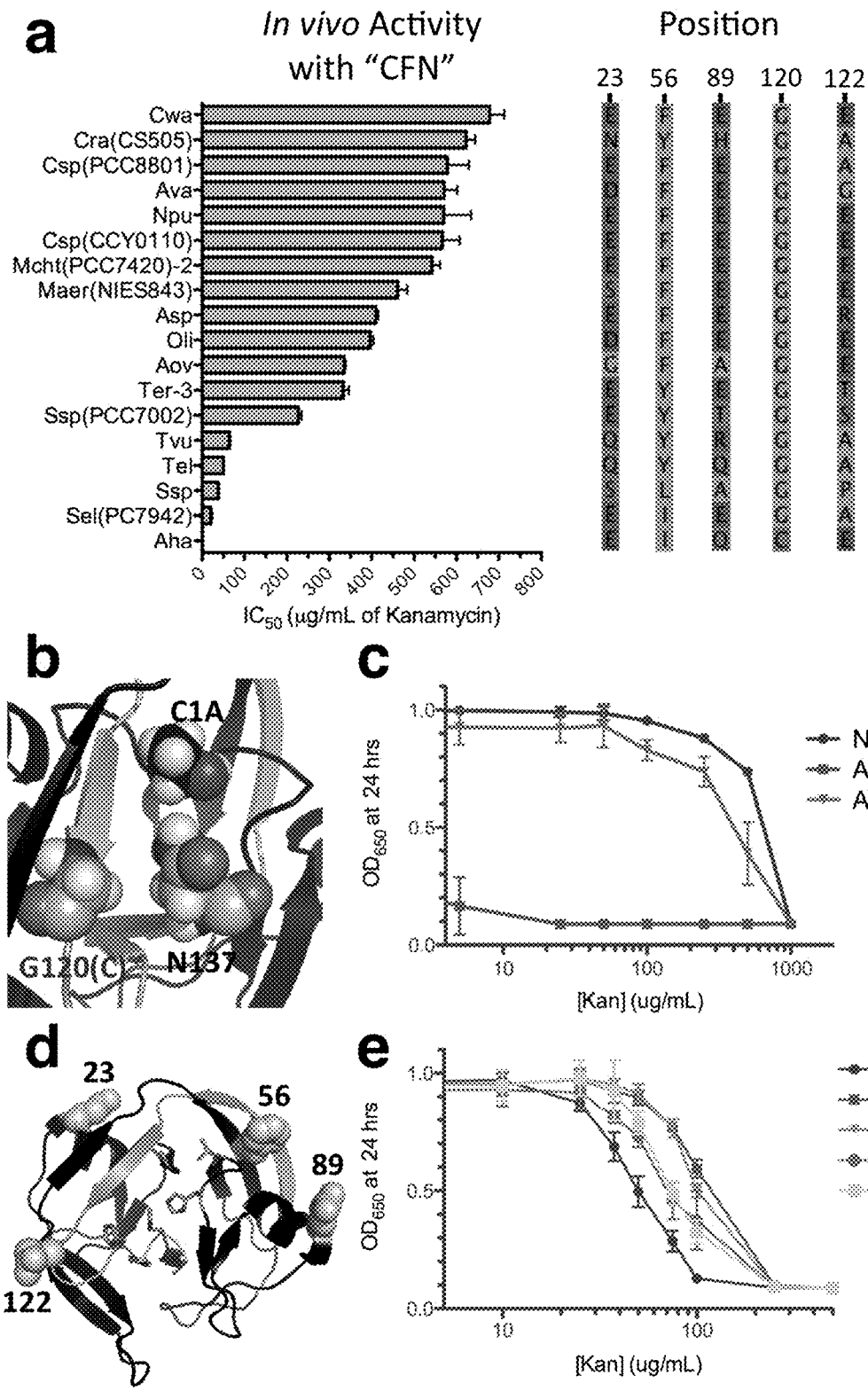
Figure 5:
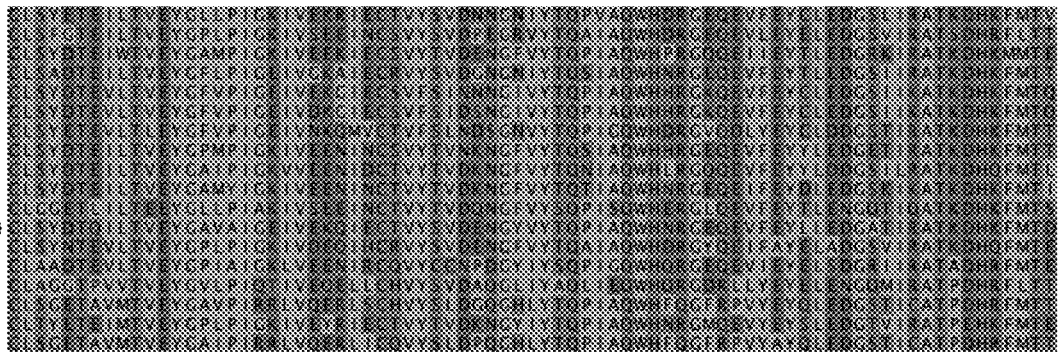
Figure 5:
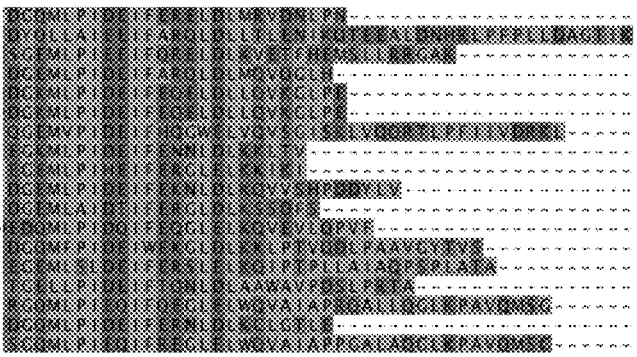
Figure 5:
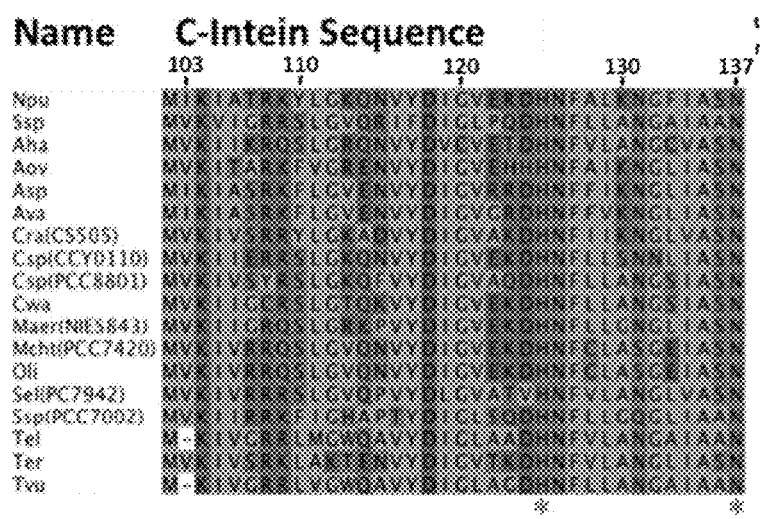

These data indicate that the split DnaE inteins are highly divergent in activity, despite all having evolved to catalyze trans-splicing on virtually identical substrates. Interestingly, the key catalytic residues involved in splicing are conserved across the entire family (FIG. 5). Thus, residues that affect splicing activity are non-catalytic and perhaps only moderately conserved. The measurements of relative activity can facilitate the discovery of specific sequence features that differentiate high-activity inteins from inefficient ones. Indeed, sequence homology analysis indicates that inteins with high activity are more homologous to one another than they are to the low-activity inteins. One significant outlier to this observation is the intein from Aphanothece halophytica (Aha), which despite having greater than 65% sequence identity to the high-activity inteins, was inactive with the wild-type "CFN" C-extein motif in vivo. Closer inspection of a multiple sequence alignment indicated that this intein has a non-catalytic cysteine (position 120) in place of an otherwise absolutely conserved glycine (FIG. 3a). Furthermore, this position is close to the intein active site, where an extra nucleophile may facilitate undesirable side reactions (FIG. 3b). Gratifyingly, mutating this cysteine to glycine reinstated high activity in the Aha intein whilst the reverse mutation destroyed the splicing activity of Npu (FIG. 3c), validating the predictive capacity of these data.

Figure 6:
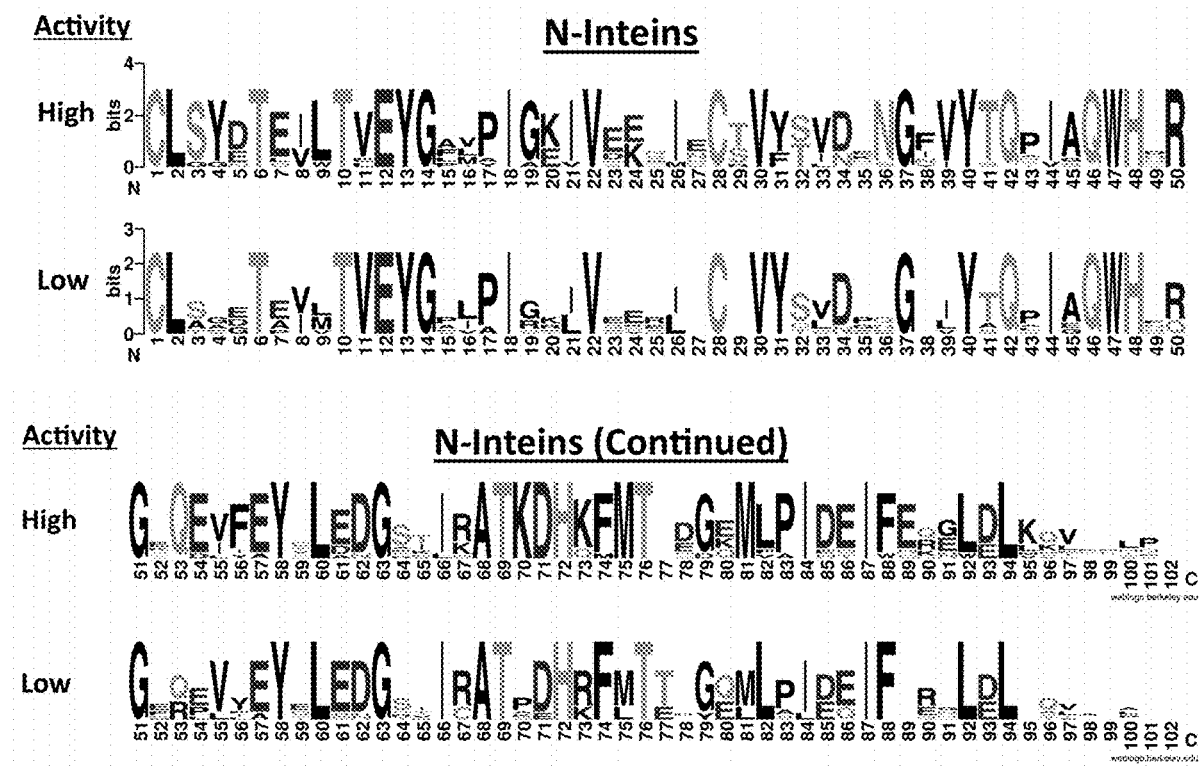
Figure 6:
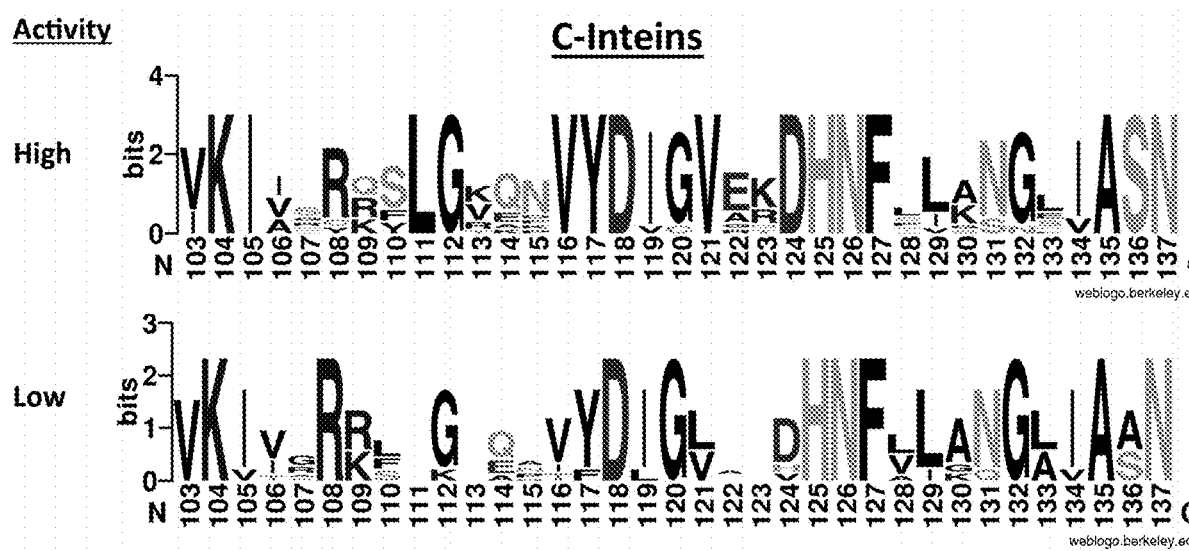

Further analysis of the split intein sequence alignment indicated that several positions have strong amino acid conservation amongst the high-activity inteins but diverge for the low-activity inteins (FIGS. 3a, 6). These may be sites where the fast inteins have retained beneficial interactions that have been lost in slow ones. To test this idea, several positions were chosen where this sequence-activity correlation was apparent and replaced the residue in Ssp with the corresponding amino acid found in the fast inteins. Consistent with this hypothesis, several point mutations increased the activity of Ssp in vivo (FIG. 3e). While the specific roles of these residues are not explicitly clear, especially given that they lie outside of the active site (FIG. 3d), their locations on the intein fold (14) may provide some insights into their function. For example, at position 56, an aromatic residue is preferred in the high-activity inteins. This position is adjacent to the conserved catalytic TXXH motif (positions 69-72), and an aromatic residue may facilitate packing interactions to stabilize those residues. Similarly, a glutamate is preferred at position 122, proximal to catalytic histidine 125. The glutamate at position 89 is involved in an intimate ion cluster that was previously shown to be important for stabilizing the split intein complex.(13) Interestingly, E23 is distant from the catalytic site and has no obvious structural role. This position is conceivably important for fold stability or dynamics as has previously been observed for activating point mutations in other inteins.(15, 16)

The discovery of new, fast trans-splicing inteins has broad implications for protein chemistry. Indeed, the discovery of Npu fueled a resurgence in the use of split intein-based technologies.(13,17,18) While no single intein may be ideal for every protein chemistry endeavor, the availability of several new fast-splicing split inteins can provide options to enhance the efficiency of most trans-splicing applications. For example, one common problem in working with split inteins is low expression yield or poor solubility of an intein fragment fusion to a protein of interest. Indeed, the overexpression and purification efforts here show that the Ub-IntN and IntC-SUMO fusions have markedly different yields of soluble expression, depending on the intein. Thus, a short-list of highly active split inteins with varying behavior will serve as starting point for empirical optimization of a given trans-splicing application.

Furthermore, the fragments of the different fast-splicing split inteins can be mixed as non-cognate pairs and still retain highly efficient splicing activity, further expanding the options available for any trans-splicing application. For example, the N-fragment split intein of Npu or variant thereof can bind to the C-fragment of Npu or variant thereof or any of the other split intein C-fragments or variants discussed below. Similarly, the N-fragment of Ssp or variant thereof can bind to the C-fragment of Ssp or variant thereof or any of the other split intein C-fragments or variants thereof discussed below; the N-fragment of Aha or variant thereof can bind to the C-fragment of Aha or variant thereof or any of the other split intein C-fragments or variants thereof discussed below; the N-fragment of Aov or variant thereof can bind to the C-fragment of Aov or variant thereof or any of the other split intein C-fragments or variants thereof discussed below; the N-fragment of Asp or variant thereof can bind to the C-fragment of Asp or variant thereof or any of the other split intein C-fragments or variants thereof discussed below; the N-fragment of Ava or variant thereof can bind to the C-fragment of Ava or variant thereof or any of the other split intein C-fragments or variants thereof discussed below; the N-fragment of Cra(CS5505) or variant thereof can bind to the C-fragment of Cra(CS5505) or variant thereof or any of the other split intein C-fragments or variants thereof discussed below; the N-fragment of Csp(CCY0110) or variant thereof can bind to the C-fragment of Csp(CCY0110) or variant thereof or any of the other split intein C-fragments or variants thereof discussed below; the N-fragment of Csp(PCC8801) or variant thereof can bind to the C-fragment of Csp(PCC8801) or variant thereof or any of the other split intein C-fragments or variants thereof discussed below; the N-fragment of Cwa or variant thereof can bind to the C-fragment of Cwa or variant thereof or any of the other split intein C-fragments or variants thereof discussed below; the N-fragment of Maer(NIES843) or variant thereof can bind to the C-fragment of Maer (NIES843) or variant thereof or any of the other split intein C-fragments or variants thereof discussed below; the N-fragment of Mcht(PCC7420) or variant thereof can bind to the C-fragment of Mcht(PCC7420) or variant thereof or any of the other split intein C-fragments or variants thereof discussed below; the N-fragment of Oli or variant thereof can bind to the C-fragment of Oli or variant thereof or any of the other split intein C-fragments or variants thereof discussed below; the N-fragment of Sel(PC7942) or variant thereof can bind to the C-fragment of Sel(PC7942) or variant thereof or any of the other split intein C-fragments or variants thereof discussed below; the N-fragment of Ssp (PCC7002) or variant thereof can bind to the C-fragment of Ssp(PCC7002) or variant thereof or any of the other split intein C-fragments or variants thereof discussed below; the N-fragment of Tel or variant thereof can bind to the C-fragment of Tel or variant thereof or any of the other split intein C-fragments or variants thereof discussed below; the N-fragment of Ter or variant thereof can bind to the C-fragment of Ter or variant thereof or any of the other split intein C-fragments or variants thereof discussed below; and the N-fragment of Tvu or variant thereof can bind to the C-fragment of Tvu or variant thereof or any of the other split intein C-fragments or variants thereof discussed below.

Figure 4:
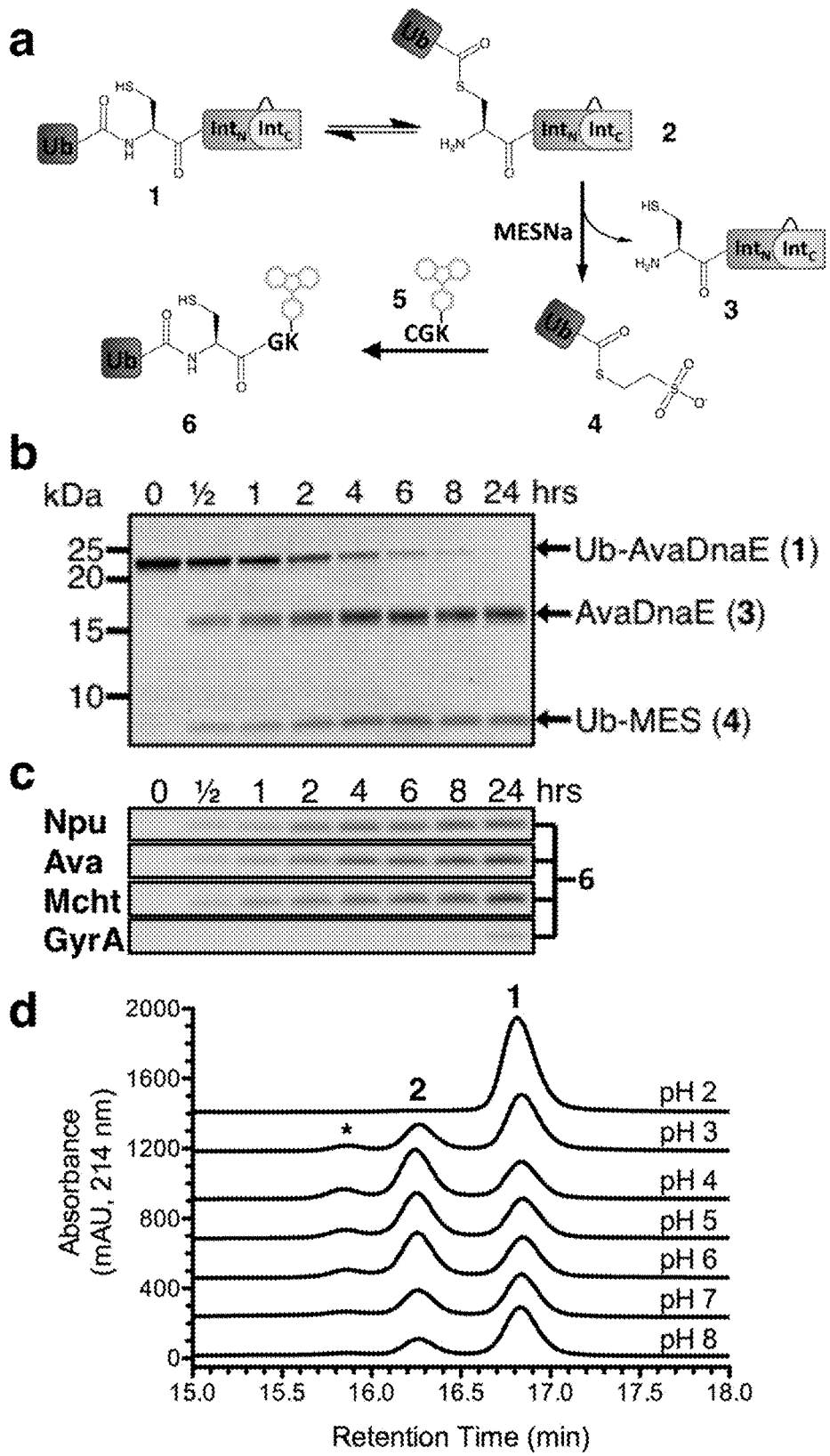

The most widely used intein-based technology, expressed protein ligation, exploits cis-acting inteins to generate recombinant protein α-thioester derivatives.(2) In principle, any split intein can be artificially fused and then utilized as a cis-splicing intein in this application (1 in FIG. 4a). Ultrafast split inteins are especially attractive in this regard due to their speed and efficiency. To test this notion, artificially fused variants of Npu, Ava, and Mcht with an N-terminal ubiquitin domain were generated. To prevent splicing, premature C-terminal cleavage or undesired high levels of competing hydrolysis residues Asn137 and Cys+1 were mutated to Ala. Upon reaction with the exogenous thiol sodium 2-mercaptoethanesulfonate (MESNa), the fused DnaE inteins were rapidly cleaved to generate the ubiquitin α-thioester, 4, in a few hours (FIG. 4b). By contrast, MESNa thiolysis of the commonly used MxeGyrA intein was not complete even after one day under identical conditions. The fused DnaE inteins were sufficiently fast to allow for a one-pot thiolysis and native chemical ligation reaction with an N-terminal cysteine-containing fluorescent peptide, 5, to give semisynthetic protein 6 (FIG. 4c). Furthermore, these inteins could be used to efficiently generate α-thioesters of four other structurally unique proteins domains with different C-terminal amino acid residues. These results demonstrate that fused versions of split DnaE inteins will be of general utility for protein semisynthesis.

The rapid rate of thiolysis observed for the fused DnaE inteins has mechanistic implications as well as practical ones. Without wishing to be bound by theory, one possible explanation for their enhanced reactivity over the MxeGyrA intein is that these inteins drive the N-to-S acyl shift reaction more efficiently, generating a larger population of the reactive linear thioester species 2 (FIG. 4a). This thioester intermediate is generally thought to be transiently populated in protein splicing, and to our knowledge, it has never been directly observed.(1) Surprisingly, when analyzing the ubiquitin-DnaE intein fusions by reverse phase HPLC, two major peaks and a third minor peak were often observed, all bearing the same mass. The relative abundance of these species could be modulated by unfolding the proteins or by changes in pH, and the two major species were almost equally populated from pH 4-6 (FIG. 4d). The major peaks most likely correspond to the precursor amide, 1, and the linear thioester, 2, and the minor peak as the tetrahedral oxythiazolidine intermediate. Importantly, only a single HPLC peak was seen for the ubiquitin-MxeGyrA fusion under identical conditions. These observations, along with the enhanced thiolysis rates, strongly support the notion that these DnaE inteins have a hyper-activated N-terminal splice junction.

Splicing activities in an entire family of split inteins has been characterized. Ultrafast protein trans-splicing may be the norm, rather than the exception, in this family. Furthermore, different split inteins have varying degrees of tolerance for C-extein mutations, suggesting that traceless protein splicing may be attainable by modestly engineering any highly active intein. A thorough comparison of the activities of a small family of homologous proteins can be used to identify important non-catalytic positions that modulate activity. Finally, by artificially fusing split DnaE intein fragments, new constructs have been provided for the efficient synthesis of protein α-thioesters used in expressed protein ligation. These results will guide the development of improved protein chemistry technologies and should lay the groundwork towards a more fundamental understanding of efficient protein splicing.

Fusion Proteins of Split Intein N-Fragment

Disclosed herein are fusion proteins of a polypeptide and a split intein N-fragment. As used herein, the term "polypeptide" refers to any amino acid based polymer, interchangeable referred to as a "protein" throughout, and can include glycoproteins and lipoproteins. In some cases, the polypeptide is a polypeptide excreted from a cell (e.g., a mammalian cell). In various cases, the polypeptide is an antibody or a fragment thereof. The polypeptide can be any naturally occurring or synthetic polypeptide of interest, including polypeptides having one or more amino acid residues other than the 20 naturally occurring amino acids.

In some cases, the polypeptide has a molecular weight of 45 kDa or greater, 50 kDa or greater, 60 kDa or greater, 75 kDa or greater, 100 kDa or greater, 120 kDa or greater, or 150 kDa or greater. The polypeptide can be, e.g., an antibody or a fragment thereof. In cases of antibodies, the split intein N-fragment can be fused to one or both of the heavy chains, and/or to one or both of the light chains. In some cases, the polypeptide is a protein secreted from a cell, e.g., a mammalian cell.

The split intein N-fragment comprises a sequence as shown in FIG. 5, e.g., Npu (SEQ ID NO: 1), Ssp (SEQ ID NO: 2), Aha (SEQ ID NO: 3), Aov (SEQ ID NO: 4), Asp (SEQ ID NO: 5), Ava (SEQ ID NO: 6), Cra(CS505) (SEQ ID NO: 7), Csp(CCY0110) (SEQ ID NO: 8), Csp(PCC8801) (SEQ ID NO: 9), Cwa (SEQ ID NO: 10), Maer(NIES843) (SEQ ID NO: 11), Mcht(PCC7420) (SEQ ID NO: 12), Oli (SEQ ID NO: 13), Sel(PC7942) (SEQ ID NO: 14), Ssp (PCC7002) (SEQ ID NO: 15), Tel (SEQ ID NO: 16), Ter (SEQ ID NO: 17), Tvu (SEQ ID NO: 18), or a variant thereof. In some cases, the spilt intein N-fragment sequence comprises a sequence other than Npu (SEQ ID NO: 1) or Ssp (SEQ ID NO: 2), and in other cases, comprises a sequence other than Npu (SEQ ID NO: 1), Ssp (SEQ ID NO: 2), or Aha (SEQ ID NO: 3). In some specific cases, the split intein N-fragment sequence comprises a sequence of Ava (SEQ ID NO: 6), Cra (SEQ ID NO: 7), Csp(PCC8801) (SEQ ID NO: 9), Cwa (SEQ ID NO: 10), Mcht(PCC7420) (SEQ ID NO: 12), Oli (SEQ ID NO: 13), Ter (SEQ ID NO: 17) and Tvu (SEQ ID NO: 18). In some cases, the split intein N-fragment has a sequence comprising a consensus sequence of SEQ ID NO: 19:

(CLSYDTEILTVEYGAVPIGKIVEENIECTVYSVDENGFVYTQPIAQWHD

RGEQEVFEYCLEDGSTIRATKDHKFMTEDGEMLPIDEIFEQGLDLKQVKG

LPD).

As used herein, a variant of a split intein N-fragment is a mutated split intein N-fragment as disclosed herein that maintains the activity of the split intein N-fragment (e.g., its ability to bind to a split intein C-fragment and/or catalyze nucleophilic attack of the polypeptide fused to it). Contemplated variants of a split intein N-fragments disclosed herein include mutation of one or more C residues, except for Cys1, to an aliphatic residue, such as an A, I, L, or F, or to a S residue. One such variant contemplated is a mutant Npu with Cys28 and Cys59 mutated to Ser, SEQ ID NO: 20

(CLSYETEILTVEYGLLPIGKIVEKRIESTVYSVDNNGNIYTQPVAQWHD

RGEQEVFEYSLEDGSLIRATKDHKFMTVDGQMLPIDEIFERELDLMRVDN

LPN).

Mutated Split Intein C-Fragments and Binding to a Support

The split intein C-fragments disclosed herein are mutated from the naturally occurring sequences to mutate the N137 and C+1 residues to a residue other than Asn or Gln for N137 and a residue other than Cys for C+1 (SEQ ID NOs: 129-146). In some cases, the mutations at these two positions are to a hydrophobic residue, e.g., not containing a free SH thiol (Cys), a carboxylic acid (Asp, Glu), or a base (Arg, His, Lys) or other undesired group (e.g., Asn, Gln) on the side chain. In various cases, the two mutated aliphatic residues can be the same or different and can be A, V, I, S, M, H, L, F, Y, G, or W or can be a unnatural (e.g., not encoded by genetic code) aliphatic amino acid residue such as norleucine, 2-aminobutyric acid, nor-valine, 2-aminopentoic acid, or 2-aminohexaanoic acid (SEQ ID NOs: 219-236). Specifically contemplated are mutations where both residues are selected from A, I, V, L, Y, G and F (SEQ ID NOs: 309-326). In various cases, at least one of the two mutated residues is A.

Thus, provided herein is a mutated split intein C-fragment comprising a mutation at N137 and Cys+1 of Npu (SEQ ID NOs: 129, 147, 165, 183, 201, 219, 237, 255, 273, 291, 309, 327, 345, 363, 381 and 399), Ssp (SEQ ID NOs: 130, 148, 166, 184, 202, 220, 238, 256, 274, 292, 310, 328, 346, 364, 382 and 400), Aha (SEQ ID NOs: 131, 149, 167, 185, 203, 221, 239, 257, 275, 293, 311, 329, 347, 365, 383 and 401), Aov (SEQ ID NOs: 132, 150, 168, 186, 204, 222, 240, 258, 276, 294, 312, 330, 348, 366, 384 and 402), Asp (SEQ ID NOs: 133, 151, 169, 187, 205, 223, 241, 259, 277, 295, 313, 331, 349, 367, 385 and 403), Ava (SEQ ID NOs: 134, 152, 170, 188, 206, 224, 242, 260, 278, 296, 314, 332, 350, 368, 386 and 404), Cra(CS505) (SEQ ID NOs: 135, 153, 171, 189, 207, 225, 243, 261, 279, 297, 315, 333, 351, 369, 387 and 405), Csp (CCY0110) (SEQ ID NOs: 136, 154, 172, 190, 208, 226, 244, 262, 280, 298, 316, 334, 352, 370, 388 and 406), Csp(PCC8801) (SEQ ID NOs: 137, 155, 173, 191, 209, 227, 245, 263, 281, 299, 317, 335, 353, 371, 389 and 407), Cwa (SEQ ID NOs: 138, 156, 174, 192, 210, 228, 246, 264, 282, 300, 318, 336, 354, 372, 390 and 408), Maer (NIES843) (SEQ ID NOs: 139, 157, 175, 193, 211, 229, 247, 265, 283, 301, 319, 337, 355, 373, 391 and 409), Mcht (PCC7420) (SEQ ID NOs: 140, 158, 176, 194, 212, 230, 248, 266, 284, 302, 320, 338, 356, 374, 392 and 410), Oli (SEQ ID NOs: 141, 159, 177, 195, 213, 231, 249, 267, 285, 303, 321, 339, 357, 375, 393 and 411), Sel(PC7942) (SEQ ID NOs: 142, 160, 178, 196, 214, 232, 250, 268, 286, 304, 322, 340, 358, 376, 394 and 412), Ssp(PCC7002) (SEQ ID NOs: 143, 161, 179, 197, 215, 233, 251, 269, 287, 305, 323, 341, 359, 377, 395 and 413), Tel (SEQ ID NOs: 144, 162, 180, 198, 216, 234, 252, 270, 288, 306, 324, 342, 360, 378, 396 and 414), Ter (SEQ ID NOs: 145, 163, 181, 199, 217, 235, 253, 271, 289, 307, 325, 343, 361, 379, 397 and 415), or Tvu (SEQ ID NOs: 146, 164, 182, 200, 218, 236, 254, 272, 290, 308, 326, 344, 362, 380, 398 and 416), where the mutation at N137 and Cys+1 is a naturally occurring or unnatural hydrophobic residue. In some specific cases, at least one of the mutations is A (SEQ ID NOs: 183-200, 255-272, 327-344, and 345-416) and in more specific cases, both mutations are A (SEQ IS NOs: 399-416).

A variety of supports can be used. Generally, the solid support is a polymer or substance that allows for linkage of the split intein C-fragment, optionally via a linker. The linker can be further amino acid residues engineered to the C-terminus of the split intein C-fragment or can be other known linkers for attachment of a peptide to a support. One contemplated linker is a small peptide -SGGC (SEQ ID NO: 705), where the thiol of the C-terminal Cys can be used to attach the split intein C-fragment to the support. Thus, specifically contemplated are mutated split intein C-fragments of the Npu, Ssp, etc. sequences noted above having a -SGGC peptide linker (SEQ ID NO: 705) (e.g., specifying the residues starting at the N137 position: AAFN-SGGC) (SEQ ID NO:706). The length of a peptide linker can be modified to provide varying lengths and flexibility in any individual situation (e.g., more than 2 Gly residues). It will also be apparent that the C-terminus residue of a peptide linker can be modified to introduce an appropriately reactive functional group to attach the split intein C-fragment to a surface of choice (e.g., Lys to react via an amine, Cys to react via a thiol, or Asp or Glu to react via a carboxylic acid). Other, unnatural amino acid residues are also contemplated for use in a peptide linker to provide other functional group moieties to allow for different attachment chemistry of the C-fragment to a support of interest (e.g., azide, alkynes, carbonyls, amino-oxy, cyano-benzothiazoles, tetrazoles, alkenes, alkyl-halides). The linker can alternatively be a polymeric linker.

Based upon an analysis of the sequences of the highly active split intein C-fragments investigated, a consensus sequence for the split intein C-fragment is derived: SEQ ID NO: 707 (VKIISRQSLGKQNVYDIGVEKDHNFLLAN-GLIASN), as well as a mutated version where the N137 is mutated to other than Asn or Gln (SEQ ID NO:708), or more specifically, N137 is mutant to a naturally occurring or unnaturally occurring hydrophobic residue, such as A, V, I, M, H, L, F, Y, G, S, H, or W or can be a unnatural (e.g., not encoded by genetic code) aliphatic amino acid residue such as norleucine, 2-aminobutyric acid, nor-valine, 2-aminopentanoic acid, or 2-aminohexanoic acid (SEQ ID NO: 709). Specifically contemplated mutations at N137 for the consensus sequences include A, I, V, L, Y, G, and F (SEQ ID NO: 710). Also contemplated is where N137 is mutated to A (SEQ ID NO: 711).

Further contemplated are variants of the consensus sequence having a residue at the +1 position other than Cys (SEQ ID NOs: 712, 716, 720, and 724). More specifically the +1 position can be a naturally occurring or unnaturally occurring hydrophobic residue such as A, V, I, M, H, L, F, Y, G, S, H, or W or can be a unnatural (e.g., not encoded by genetic code) aliphatic amino acid residue such as norleucine, 2-aminobutyric acid, nor-valine, 2-aminopentanoic acid, or 2-aminohexanoic acid (SEQ ID NOs: 713, 717, 721, and 725). Specifically contemplated are mutation at +1 position is selected from A, I, V, L, Y, G, and F (SEQ ID NOs: 714, 718, 722, and 726). In various cases, at least one of the mutated residues of the consensus sequence is A (SEQ ID NOs: 715, 719, and 723). In some cases, the consensus C-fragment sequence has both mutations as Ala (SEQ ID NO:727). Further contemplated is a consensus sequence comprising FN at the +2 and +3 positions (SEQ ID NO:728-743. Also contemplated is a consensus sequence comprising a peptide linker for attachment to a solid support, and one embodiment is -SGGC at positions +4-+7 (SEQ ID NO: 744-759).

The split intein C-fragment or variant thereof as disclosed herein can be attached to a solid support via a linker. In various cases, the linker is a polymer, including but not limited to a water-soluble polymer, a nucleic acid, a polypeptide, an oligosaccharide, a carbohydrate, a lipid, or combinations thereof. It is not critical what the linker's chemical structure is, since it serves primarily as a linker. The linker should be chosen so as not to interfere with the activity of the C-fragment. The linker can be made up of amino acids linked together by peptide bonds. Thus, in some embodiments, the linker comprises $Y_n$, wherein Y is a naturally occurring amino acid or a steroisomer thereof and "n" is any one of 1 through 20. The linker is therefore can be made up of from 1 to 20 amino acids linked by peptide bonds, wherein the amino acids are selected from the 20 naturally-occurring amino acids. In some cases, the 1 to 20 amino acids are selected from Gly, Ala, Ser, Cys. In some cases, the linker is made up of a majority of amino acids that are sterically un-hindered, such as Gly.

Non-peptide linkers are also possible. For example, alkyl linkers such as —HN—(CH$_2$)$_s$—CO—, wherein s=2-20 can be used. These alkyl linkers may further be substituted by any non-sterically hindering group such as lower alkyl (e.g., C$_1$-C$_6$), halogen (e.g., Cl, Br), CN, NH$_2$, phenyl, etc.

Another type of non-peptide linker is a polyethylene glycol group, such as: —HN—(CH$_2$)$_2$—(O—CH$_2$—CH$_2$)$_n$—O—CH$_2$—CO, wherein n is such that the overall molecular weight of the linker ranges from approximately 101 to 5000, preferably 101 to 500.

In some cases, the linker has a length of about 0-14 sub-units (e.g., amino acids).

In instances wherein the linker is a polynucleotide, the length of the linker in various embodiments is at least about 10 nucleotides, 10-30 nucleotides, or even greater than 30 nucleotides. In various aspects, the bases of the polynucleotide linker are all adenines, all thymines, all cytidines, all guanines, all uracils, or all some other modified base.

In another embodiment, a non-nucleotide linker of the invention comprises a basic nucleotide, polyether, polyamine, polyamide, peptide, carbohydrate, lipid, polyhydrocarbon, or other polymeric compounds. Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, the disclosures of which are all incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In various aspects, linkers contemplated include linear polymers (e.g., polyethylene glycol, polylysine, dextran, etc.), branched chain polymers (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); lipids; cholesterol groups (such as a steroid); or carbohydrates or oligosaccharides. Other linkers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Other useful polymers as linkers known in the art include monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

In still other aspects, oligonucleotide such as poly-A or hydrophilic or amphiphilic polymers are contemplated as linkers, including, for example, amphiphiles (including oligonucletoides).

Contemplated solid supports include resins, particles, and beads. More specific solid supports include polyhydroxy polymers, e.g. based on polysaccharides, such as agarose, dextran, cellulose, starch, pullulan, or the like, and synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinyl alcohols and polymers based on styrenes and divinylbenzenes, and copolymers in which two or more of the monomers corresponding to the above-mentioned polymers are included. Specific solid supports contemplated include agarose, sepharose, cellulose, polystyrene, polyethylene glycol, derivatized agarose, acrylamide, sephadex, sepharose, polyethyleneglycol (PEG)-acrylamide, and polystyrene-PEG based supports. In some cases, the solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYMPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden). In various embodiments, the solid support can be a magnetic bead, a glass slide, a glass bead, or a metal or inorganic particle (e.g., gold, silica, iron, or mixture thereof).

Methods of Purifying and Modifying Polypeptides

Site-specific modification of proteins is an invaluable tool to study the molecular details of protein function (19). Moreover, its potential for the discovery and development of protein therapeutics has also been recently acknowledged (20). Several methods have been developed over the years to generate site-specifically modified proteins; one of the most widely used is Expressed Protein Ligation (EPL), which has been applied to many different proteins in a variety of studies to address fundamental questions of protein function. EPL was first described in 1998 (21), as an expansion to recombinant proteins of Native Chemical Ligation (NCL) (19,22), and it consists on the reaction between a C-terminal recombinant protein α-thioester with a synthetic peptide containing a Cys at its N-terminus through the formation of a new native peptide bond between the two fragments. The synthetic nature of the Cys containing peptide allows for the incorporation of almost any chemical modification into the protein of interest.

In order to apply EPL to any given protein the generation of protein C-terminal thioesters in good yields and high purity is an absolute requirement. A family of single turnover enzymes, named inteins, has been used since the dawn of EPL for the generation of such thioesters. Inteins are able to catalyze protein splicing, a naturally occurring post-translational modification by which they excise themselves from the polypeptide in which they are embedded, concomitantly forming a new peptide bond between their flanking protein regions (23). Importantly, this reaction occurs via several protein α-thioesters, which can be trapped through a trans-thioesterification reaction with an exogenous thiol.

Inteins, such as GyrA or VMA, have been successfully harnessed to prepare a wide variety of protein thioesters. In order to isolate the desired protein thioesters inteins are usually fused to affinity tags such as the chitin binding domain or the hexa-His tag. However, despite the notable success of this strategy, the reaction conditions required for efficient thiolysis (reducing agents, large concentration of thiols and long incubation times) affect the performance of such tags and subsequent additional purification steps are often required to obtain the desired pure product for ligation (24-26). Moreover, depending on the identity of the C-terminal residue of the protein of interest, significant levels of in vivo premature cleavage can occur, significantly reducing the final product yield.

Figure 7:

An ideal system should combine the thioester formation capabilities of inteins with a built-in affinity purification strategy (fully compatible with the thiolysis reaction conditions) and reduced risk of premature cleavage. Naturally split-inteins were investigated, which can perform a reaction analogous to protein splicing but in which the intein itself is split into two different polypeptides. Each of the two intein fragments are completely inactive by themselves but have a strong affinity for each other and, upon binding, they adopt their splicing competent active conformation and are able to carry out protein trans-splicing. Recently, an artificially split version of the DnaB intein has been reported for the purification of unmodified proteins (27). Thus, a purification strategy is provided using naturally split-inteins instead and to harness them for the one pot purification and generation of recombinant protein α-thioesters (FIG. 7) directly from cell lysates.

Due to the extremely fast reaction kinetics of naturally split inteins, several mutations were introduced to allow efficient thioester formation and minimize in vivo and in vitro undesired cleavage reactions. Specifically, both the C-intein C-terminal catalytic Asn137 and the Cys+1 residues had to be mutated to Ala to prevent premature C- and N-terminal cleavage, respectively. Mutation to two sequential aliphatic residues, natural or unnatural, is also expected to yield comparable results as the AA mutation. Other mutated split intein C-fragments as described above can be used in the described purification and/or modification methods, and are specifically contemplated.

To develop a split-intein based purification and thioester formation strategy the Npu split-intein was chosen, which is one of the fastest DnaE split-inteins previously known [10]. Initially the ability of split Npu to generate protein thioesters in solution was tested by mixing the model protein ubiquitin fused to NpuN with a mutant NpuC (Asn137 and Cys+1 to Ala) in the presence (and absence) of the thiol MESNa. SDSPAGE, HPLC and MS analysis of the reactions showed the formation of the desired ubiqutin C-terminal α-thioester in a few hours. Encouraged by these results an affinity purification strategy was designed based on the covalent immobilization of the NpuC intein mutant onto a solid support. The immobilized mutated NpuC could then be used to purify NpuN tagged proteins from complex mixtures and addition of an exogenous thiol would cleave off the desired protein α-thioester, which would elute from the column in a highly purified form. Other split intein N-fragments as described above can be used in the methods disclosed herein, and are specifically contemplated.

Figure 8:
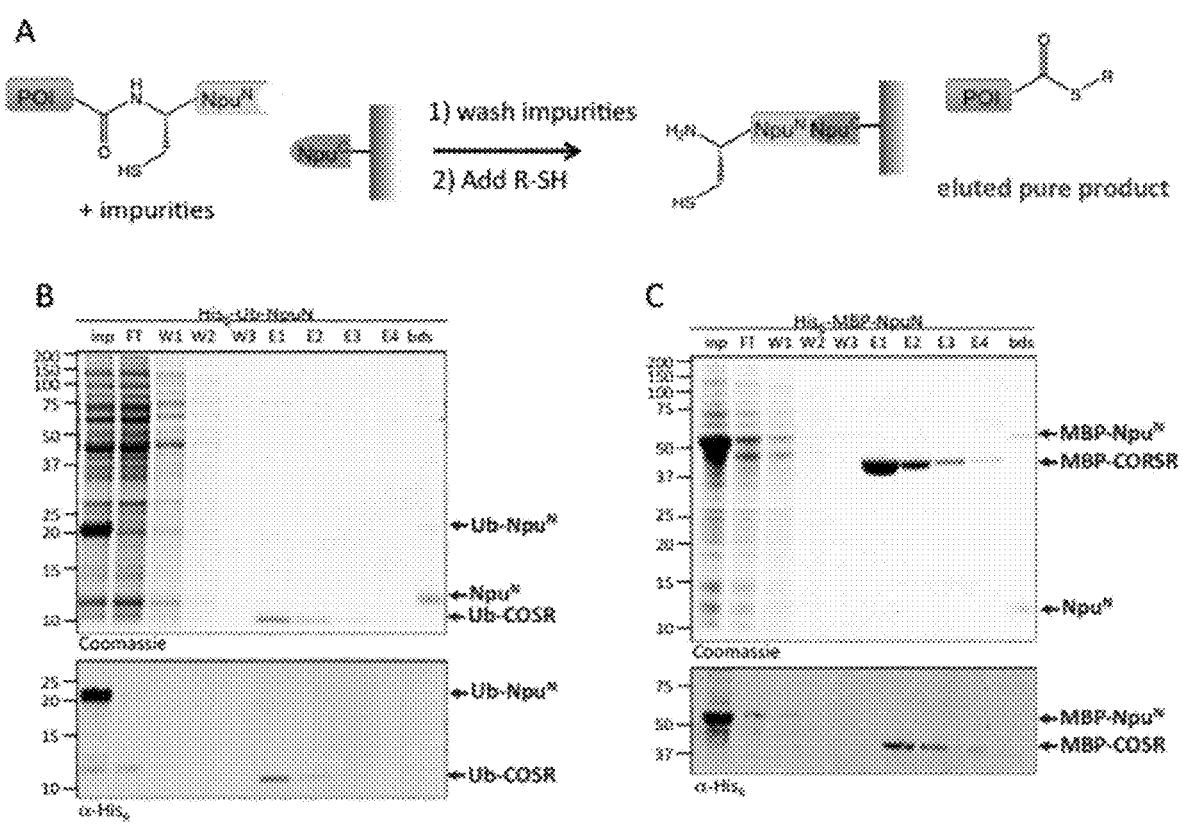
Figure 9:
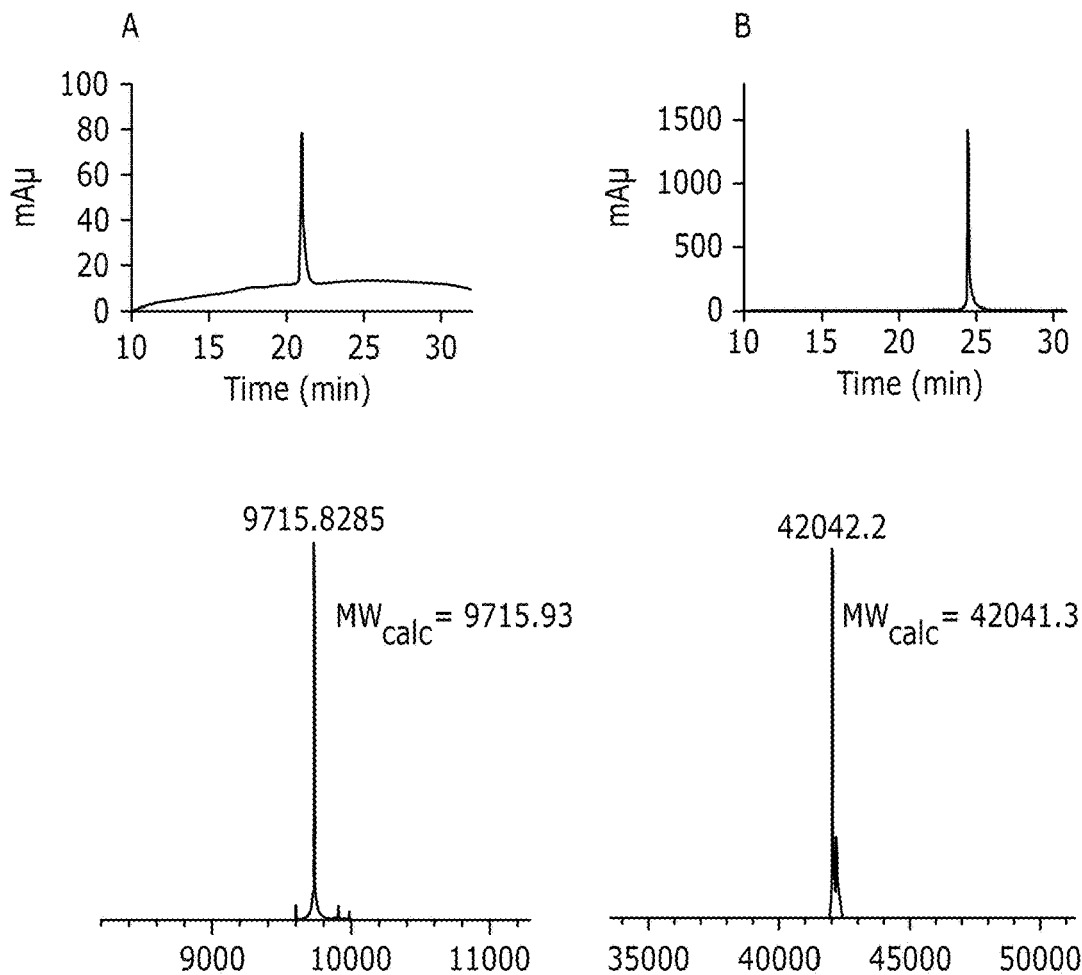
Figure 13:
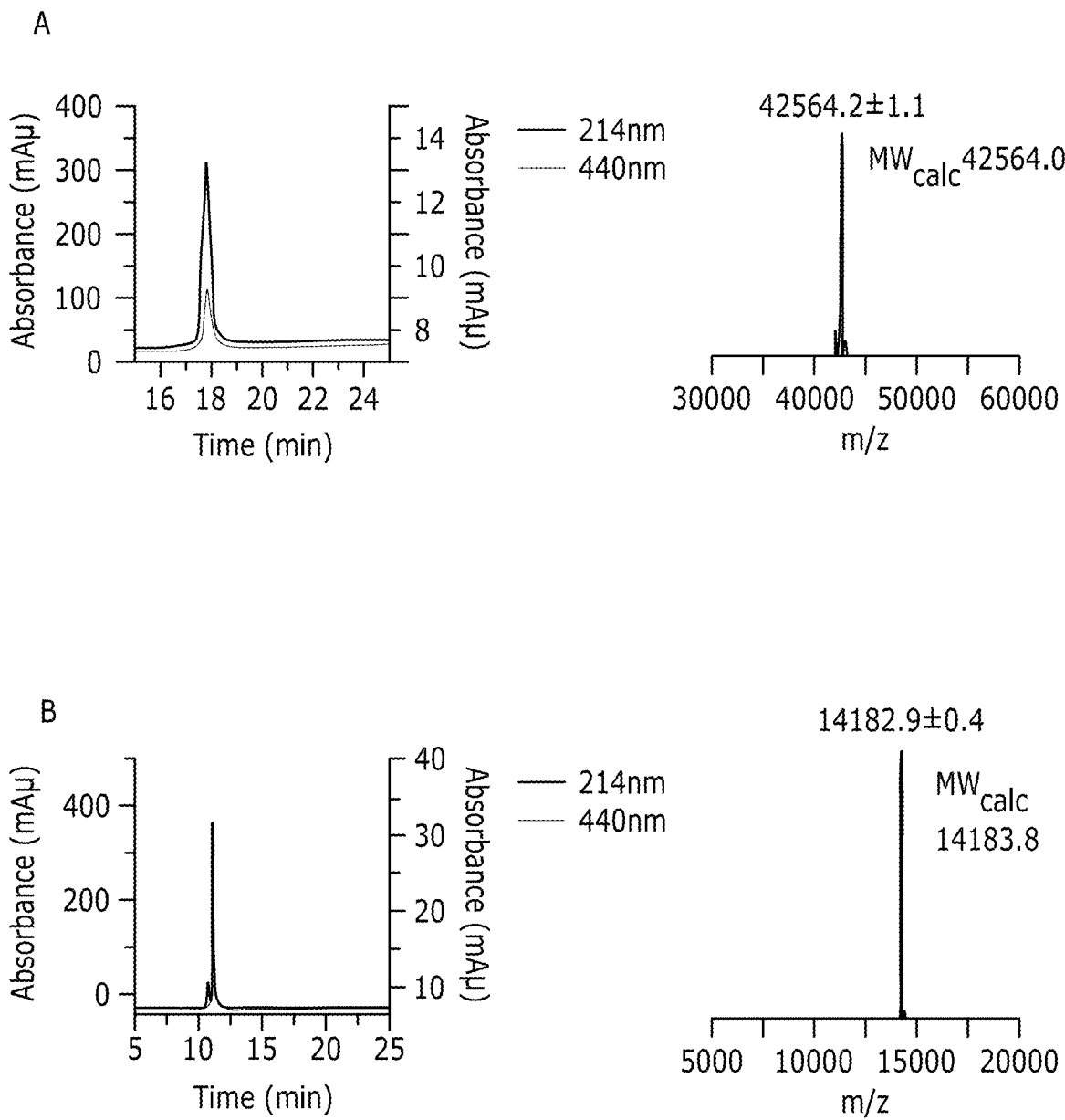
Figure 14:
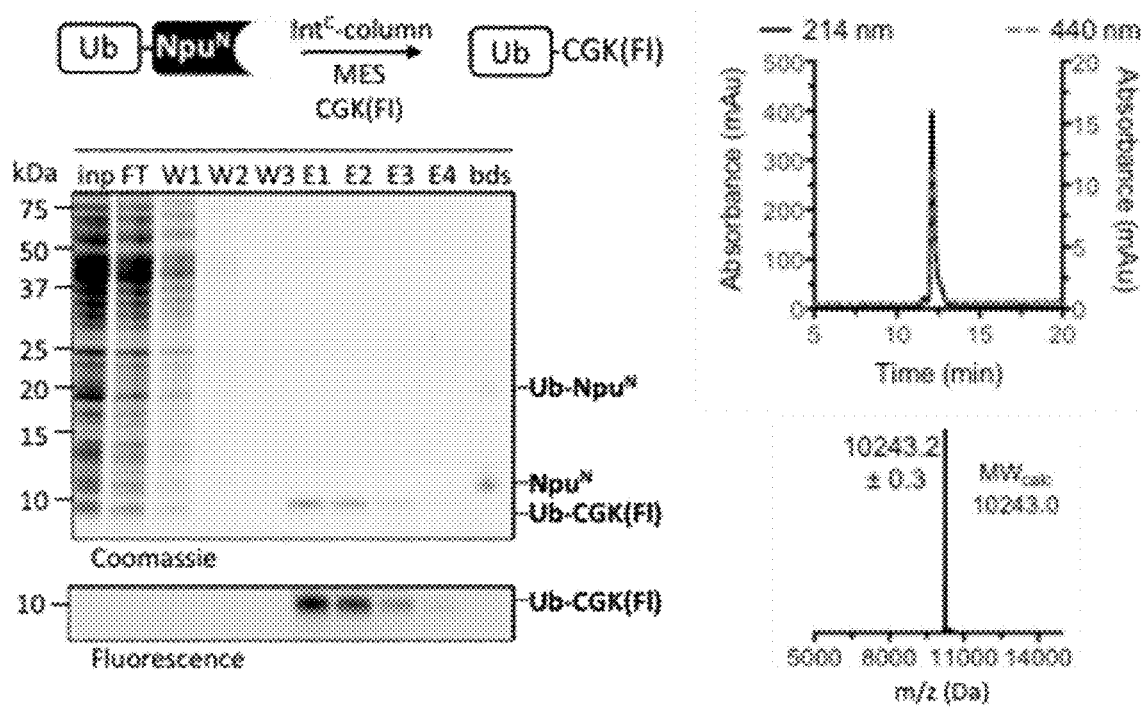

An NpuC mutant (Asn$^{137}$ and Cys$^{+1}$ mutated to Ala, NpuC-AA (SEQ. ID NO: 777) was prepared with a Cys residue at the C-terminus of its C-extein, which was used to immobilize the peptide onto a iodoacetyl resin. With the NpuC-AA affinity resin in hand, it was shown that several protein C-terminal α-thioesters (Ubiquitin, MBP, PHPT1) could be easily produced and purified out of cell lysates (FIG. 8). HPLC and MS analysis confirmed the formation of the desired protein thioesters with very low levels of undesired hydrolysis (FIG. 9). Recovery yields varied between 75 and 95% and the NpuC-AA resin had a consistent loading capacity of 3-6 mg of protein per mL. The utility of the α-thioester derivatives of Ub, MBP, and PHPT1 obtained from the column was demonstrated by ligating each of them to an N-terminal Cys-containing fluorescent peptide (CGK (Fl)) to give the corresponding semisynthetic products in excellent yield (FIG. 13). Importantly, one-pot thiolysis/ligation reactions can be carried out, which provides a site-specifically modified protein directly from cell lysates without isolating the intermediate thioester (FIG. 14).

Figure 10:
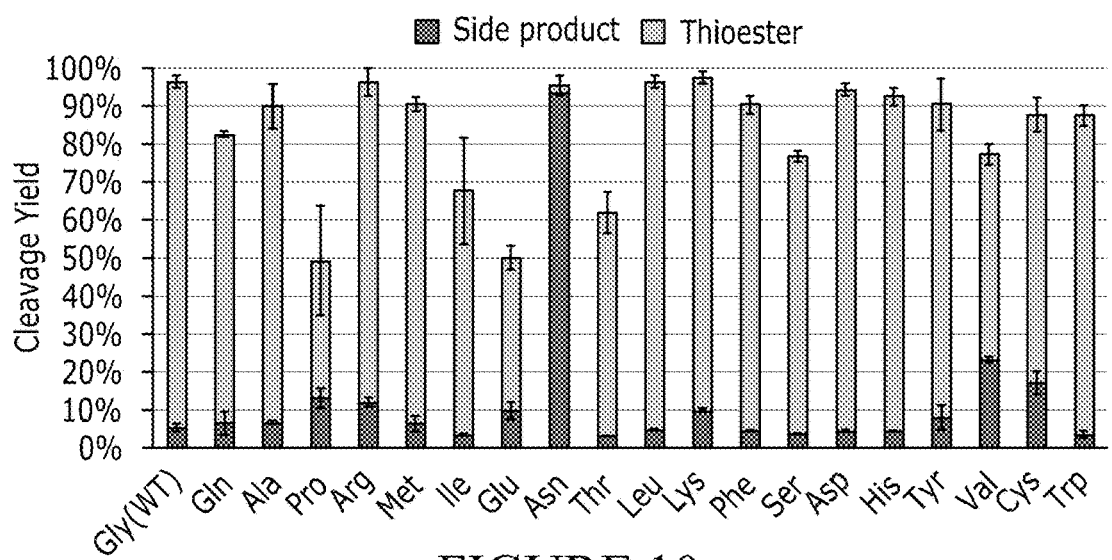

A concern when working with split-inteins (and also inteins) is the effect of the flanking amino acid sequences on splicing and/or thiolysis activity. Although the N-terminal junction is regarded as more tolerant towards deviations from the native N-extein residues it was important to evaluate the effect that the C-terminal amino acid of the protein of interest (−1 residue according to intein numbering conventions) would have on the yields of thioester formation. A complete library of Ub-X-NpuN fusion proteins was constructed where the C-terminal Ub residue (X) was varied from its native Gly to all other 19 proteinogenic amino acids. Proteins were expressed in *E. coli* and cell lysates, applied to the NpuC-AA affinity resin and purified. Protein yields were estimated from the SDSPAGE analysis for each purification and hydrolysis levels from RP-HPLC and MS analysis of the elution fractions (FIG. 10). Results show similar trends to those known for non-split inteins, such as GyrA (29), and most amino acids display high yields of cleavage after overnight incubation with MESNa, the exceptions being Pro and Glu, for which recovery were 49 and 50%, respectively. As expected, the Asn α-thioester could not be isolated due to the well-known reaction of its side-chain with the adjacent α-thioester to form a succinimide.

This purification strategy was very successful for the purification of several soluble proteins under native conditions. However, protein fragments required for EPL sometimes suffer from poor solubility and high toxicity and tend to accumulate in cellular inclusion bodies during expression. The Npu split-intein has been shown to retain a significant level of activity in the presence of denaturants (28), which suggested that this strategy would be compatible under such conditions. Using the model Ub-NpuN protein fusion it was confirmed that both, binding to the NpuC-AA-resin and thioester formation, worked well in the presence of 2 and 4 M urea. Similar levels of both, binding and thiolysis, were obtained than in the absence of denaturant and same reaction conditions.

Figure 11:
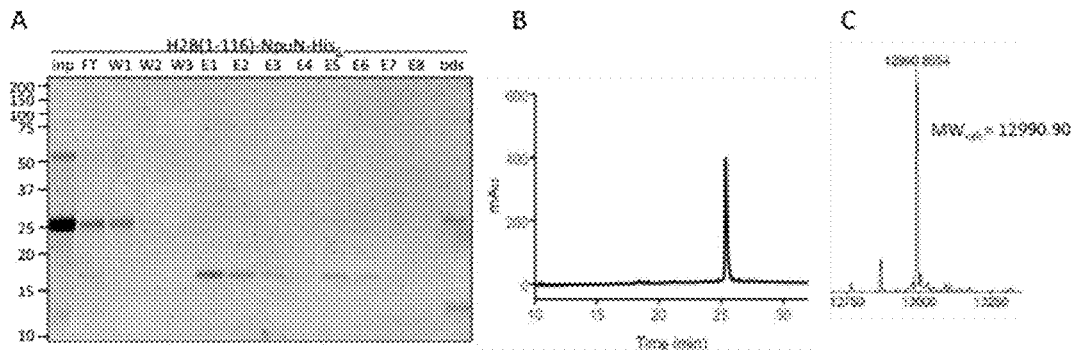

The system was next tested for the purification from inclusion bodies of a fragment of the histone H2B. Preparation of site-specifically modified histones using EPL is a topic of major interest due to their crucial role in the understanding of epigenetic regulation. However, histone fragments are remarkably poorly behaved and the preparation of their recombinant C-terminal α-thioesters particularly challenging. A H2B(1-116) fragment fused to NpuN was expressed in *E. coli* and the inclusion bodies extracted with 6 M urea. The H2B-NpuN fusion was subsequently diluted into a 3 M urea buffer and the corresponding C-terminal α-thioester generated concomitant with purification over the NpuC-AA affinity resin (FIG. 11). Due to its tendency of aggregation, very dilute protein solutions bound more efficiently to the resin, and also longer reaction times were required for efficient thioester generation, obviously, these are parameters that would need to be optimized on a protein to protein basis. Using these conditions, H2B(1-116) C-terminal thioester was obtained in excellent purity (>90% by RP-HPLC) and isolated yield (~20 mg per L of culture).

Figure 15:
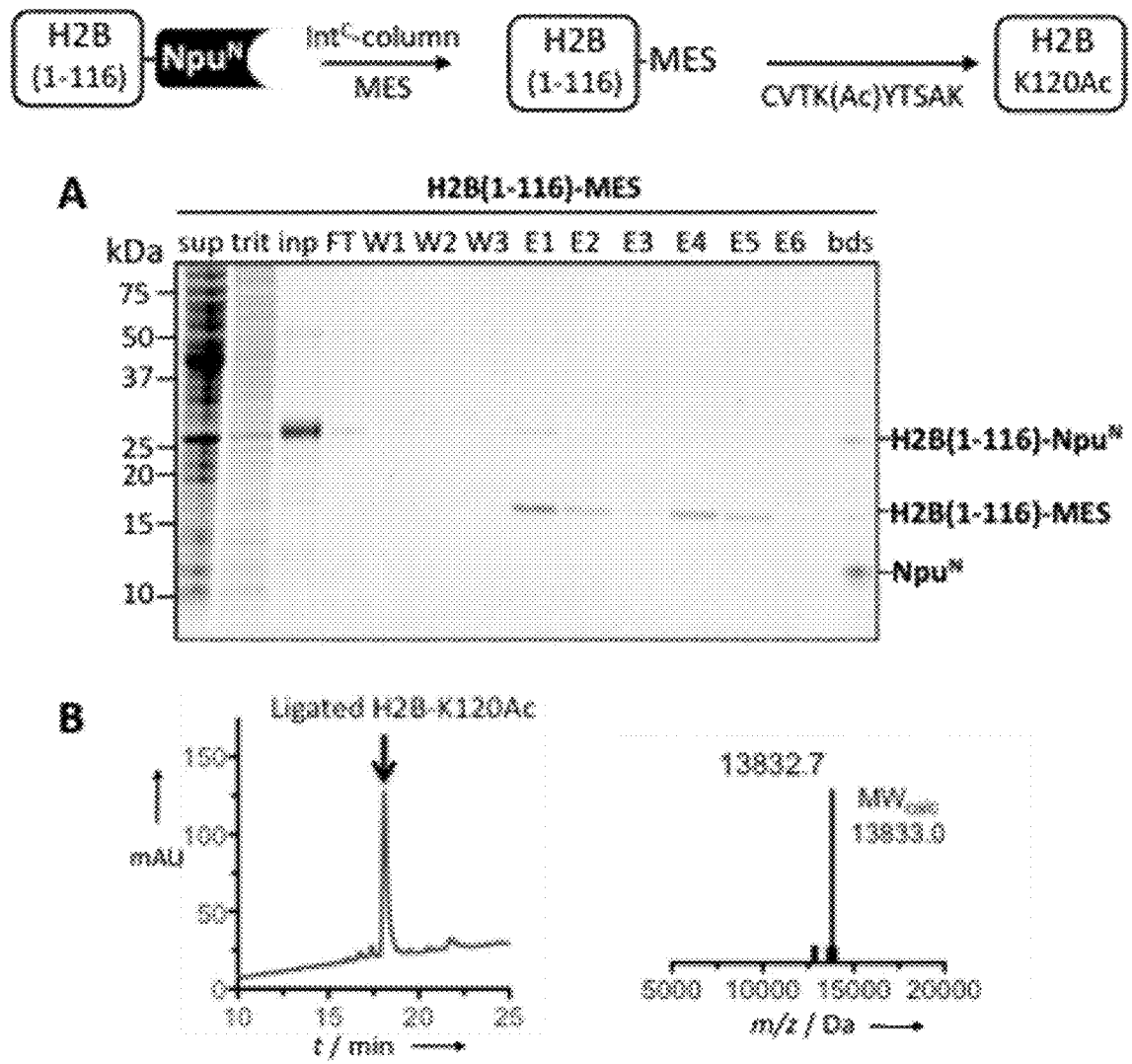
Figure 16:
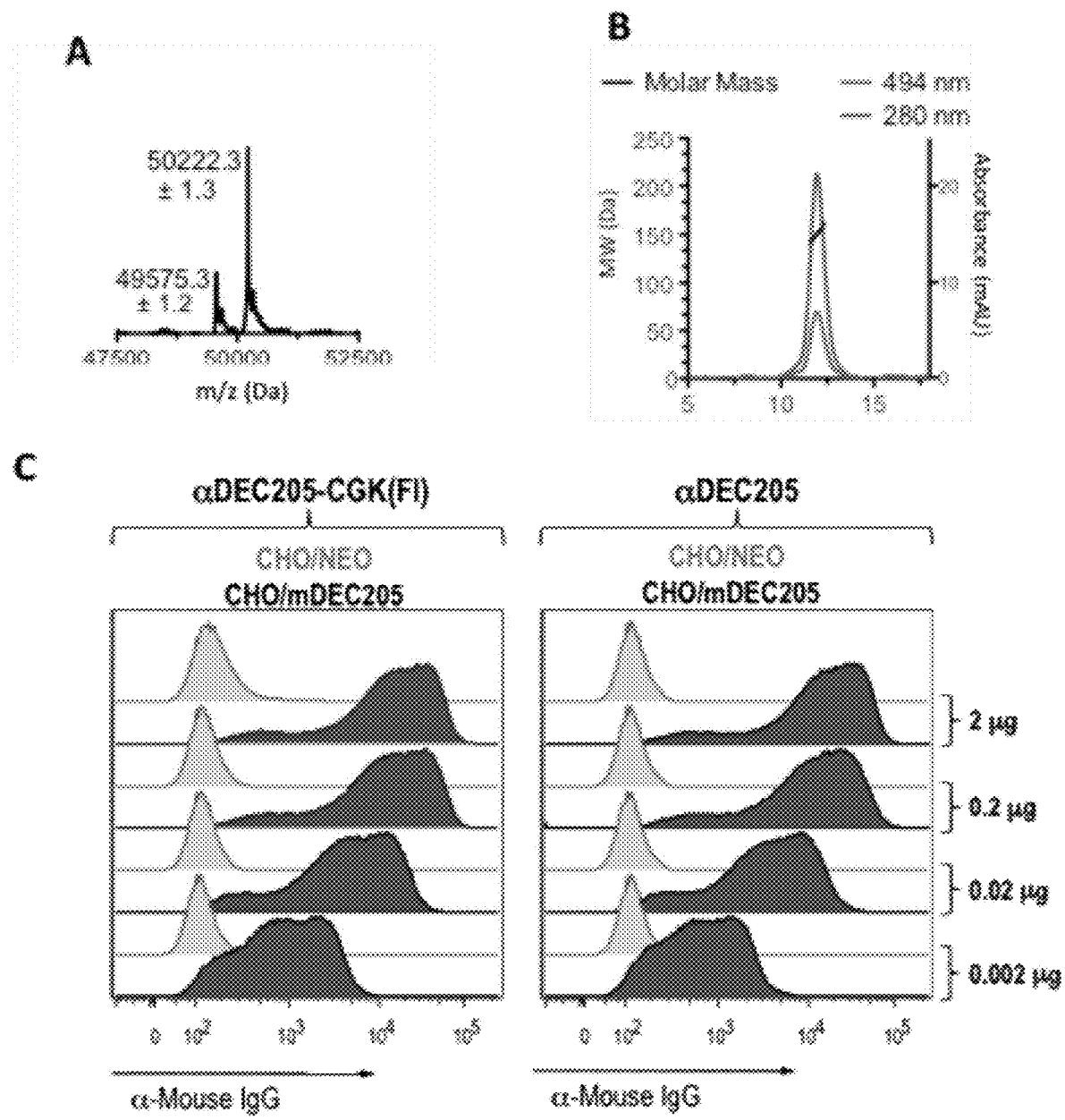
Figure 17:
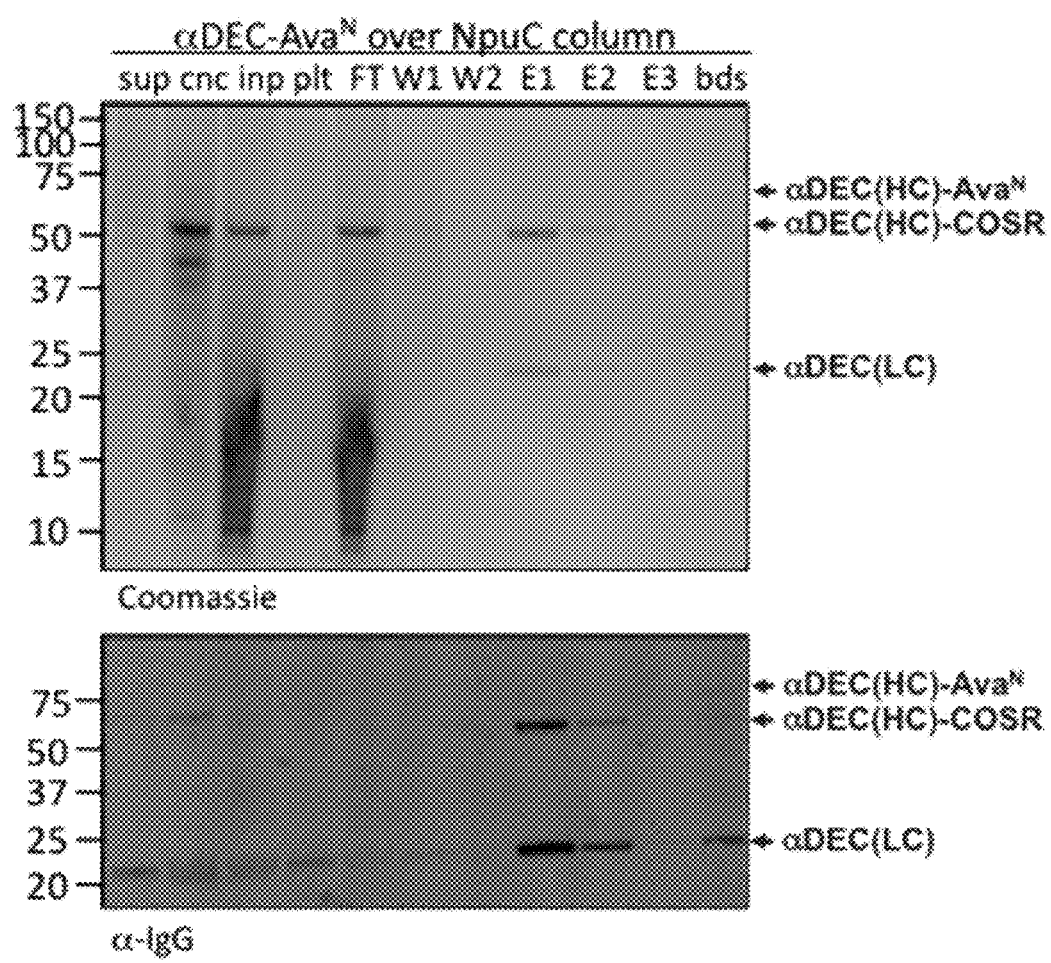
Figure 18:
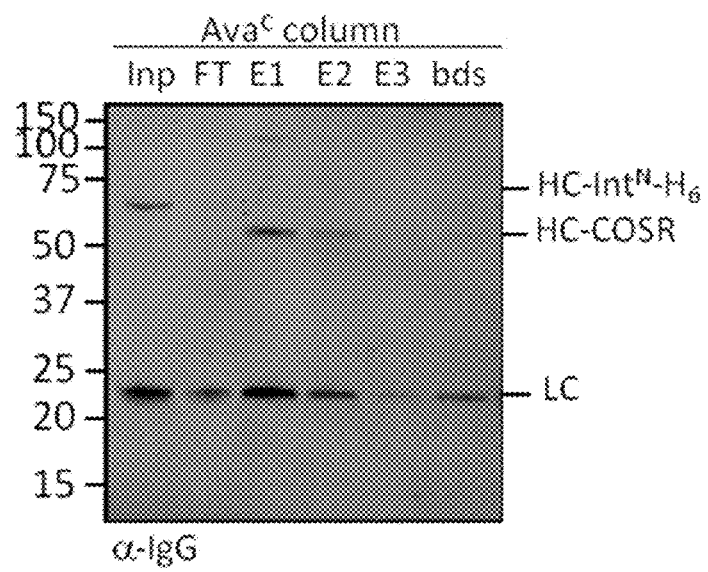
FIG. 18 shows purification of αDEC thioesters using an Ava$^C$ split-intein column and Western blot analysis of the purification of αDEC thioesters from mammalian cell supernatants using an Ava$^C$-column.
Figure 19:
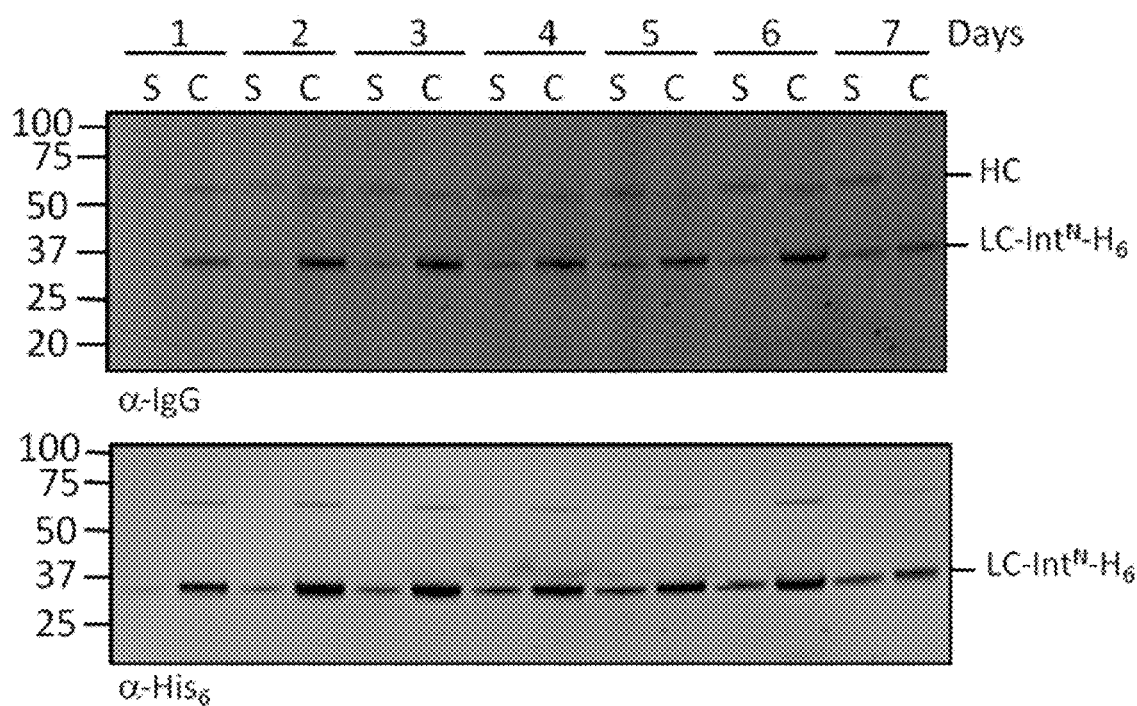
FIG. 19 shows expression tests of αDEC205 antibody fused to Ava$^N$ split intein through the C-terminus of the antibody light chain and western blot analysis of CHO cell supernatants expressing the αDEC205-AvaN fusion at different timepoints.

This represents a significant improvement over previous protocols which afford less protein (4 mg per L of culture) and require the use of multiple chromatographic purification steps including RP-HPLC. Importantly, the H2B(1-116)-MES thioester obtained from the IntC-column can be directly used in EPL reactions without further purification. Accordingly, the protein was successfully ligated to a synthetic H2B(117-125) peptide containing an acetylated Lys at position 120 to yield semi-synthetic H2B-K120Ac (FIG. 15).

The potential of this thioester formation purification strategy was demonstrated by applying it to the site-specific modification of a monoclonal antibody. Thus, specifically contemplated is a method of purifying an antibody by using a fusion protein of an antibody and a split intein N-fragment as disclosed herein and a mutated split intein C-fragment as disclosed herein.

Figure 12:
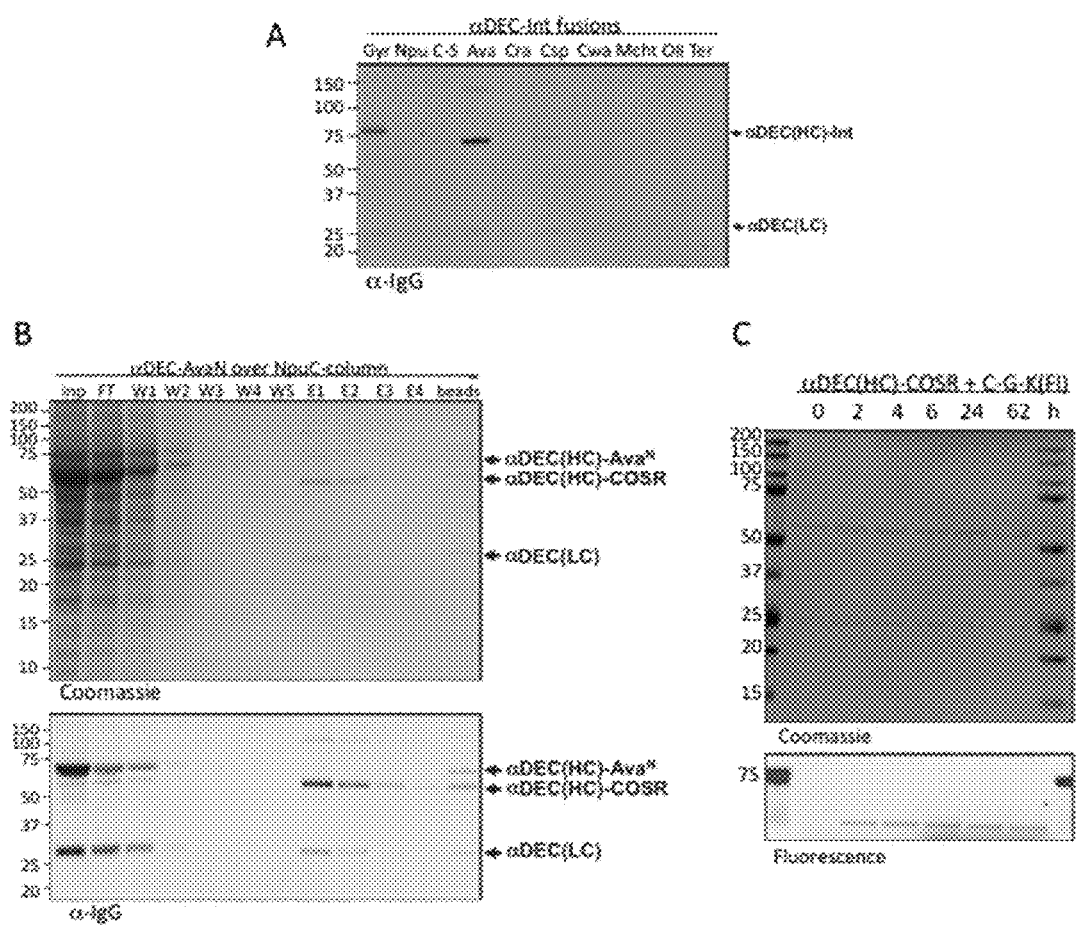

The modification of antibodies is a field of intense research, specially focused on the development of therapeutic antibody-drug-conjugates (30). The identity of the N-intein could have a significant effect on the expression levels of its fusion to a given protein of interest. The N-fragment of several of the fastest split DnaE inteins cross-reacted with NpuC, allowing one to use any of them with the same NpuC based affinity column. Accordingly, the expression levels of a model antibody (αDEC, antibody against the DEC205 receptor) were tested and found the highest levels of expression were obtained when αDEC was fused to the AvaN intein (FIG. 12A). αDEC-AvaN fusions were transfected into 293T cells and after 4 days of culture the supernatants were collected and purified over the NpuC-AA-column. The presence of a C-terminal thioester in the purified αDEC was confirmed by reacting it with a short fluorescent peptide with an N-terminal Cys residue (FIGS. 12B and C). MS of the deglycosylated and reduced αDEC-fluorophore conjugate was used to confirm its identity and SEC-MALS demonstrate the product was monodisperse and of the expected size for an IgG antibody.

Split-inteins can be engineered for the preparation of protein α-thioesters and that the strong affinity between the two split-intein fragments provides a powerful handle for their purification. The generality of the approach is demonstrated by using it to generate highly pure thioesters of both soluble (ubiqutin, MBP, PHPT) and insoluble proteins (H2B fragment) as well as monoclonal antibodies (αDEC). Moreover, several N-inteins can be tested for optimal expression levels of the protein of interest and used with one single NpuC-column.

Thus, the split inteins disclosed herein can be used to purify and modify a polypeptide of interest. A polypeptide of interest is provided in a fusion protein with a split intein N-fragment, e.g., via well-known recombinant protein methods. The fusion protein is then contacted with a corresponding split intein C-fragment under conditions that allow binding of the N-fragment and C-fragment to form an intein intermediate. The split intein C-fragment can be bound to a support (e.g., a solid support such as a resin) or can subsequently (e.g., after binding to the split intein N-fragment to form the intein intermediate) be bound to a support. This allows for the removal via washing of components that were in the mixture due to the recombinant protein synthesis, allowing the fusion protein to be isolated from the other components. Washes can include detergents, denaturing agents and salt solutions (e.g., NaCl).

Then, the intein intermediate can be reacted with a nucleophile to release the polypeptide of interest from the bound N- and C-fragment inteins wherein the C-terminus of the polypeptide is modified by the nucleophile added. The nucleophile can be a thiol to directed yield the polypeptide as an α-thioester, which in turn can be further modified, e.g., with a different nucleophile (e.g., a drug, a polymer, another polypeptide, a oligonucleotide), or any other moiety using the well-known α-thioester chemistry for protein modification at the C-terminus. One advantage of this chemistry is that only the C-terminus is modified with a thioester for further modification, thus allowing for selective modification only at the C-terminus and not at any other acidic residue in the polypeptide.

The nucleophile that is used in the methods disclosed herein either with the intein intermediate or as a subsequent nucleophile reacting with, e.g., a α-thioester, can be any compound or material having a suitable nucleophilic moiety. For example, to form a α-thioester, a thiol moiety is contemplaed as the nucleophile. In some cases, the thiol is a 1,2-aminothiol, or a 1,2-aminoselenol. An α-selenothioester can be formed by using a selenothiol (R-SeH). Alternative nucleophiles contemplated include amines (i.e. aminolysis to give amides directly), hydrazines (to give hydrazides), amino-oxy groups (to give hydroxamic acids). Additionally, the nucleophile can be a functional group within a compound of interest for conjugation to the polypeptide of interest (e.g., a drug to form a protein-drug conjugate) or could alternatively bear an additional functional group for subsequent known bioorthogonal reactions such as an azide or an alkyne (for a click chemistry reaction between the two function groups to form a triazole), a tetrazole, an α-ketoacid, an aldehyde or ketone, or a cyanobenzothiazole.

Additional aspects and details of the invention will be apparent from the following examples, which are intended to be illustrative rather than limiting.

EXAMPLES

Materials

All buffering salts, isopropyl-β-D-thiogalactopyranoside (IPTG), and N,N-diisopropylethylamine (DIPEA) were purchased from Fisher Scientific (Pittsburgh, PA). Kanamycin sulfate (Kan), β-Mercaptoethanol (BME), DL-dithiothreitol (DTT), sodium 2-mercaptoethanesulfonate (MESNa), ethanedithiol (EDT), Coomassie brilliant blue, N,N-dimethylformamide (DMF), Tetrakis(triphenylphosphine)palladium (0) (Pd(PPh$_3$)$_4$), phenylsilane, triisopropylsilane (TIS), sodium diethyldithiocarbamate trihydrate, and 5(6)-carboxyfluorescein were purchased from Sigma-Aldrich (St. Louis, MO). Tris(2-carboxyethyl)phosphine hydrochloride (TCEP) was purchased from Thermo Scientific (Rockford, IL). Fmoc-Gly-OH, Fmoc-Lys(Alloc)-OH, and Boc-Cys (Trt)-OH were purchasd from Novabiochem (Laufelfingen, Switzerland). Piperidine was purchased from Alfa Aesar (Ward Hill, MA). Dichloromethane (DCM) and rink amide resin were purchased from EMD Chemicals (Billerica, MA). 1-Hydroxybenzotriazole hydrate (HOBt) was purchased from AnaSpec (Fremont, Ca). Trifluoroacetic acid (TFA) was purchased from Halocarbon (North Augusta, SC). Complete protease inhibitor tablets were purchased from Roche Diagnostics (Mannheim, Germany). Nickel-nitrilotriacetic acid (Ni-NTA) resin was from Novagen (Gibbstown, NJ). The QuikChange XL II site directed mutagenesis kit was from Agilent (La Jolla, CA). DpnI and the Phusion High-Fidelity PCR kit were from New England Biolabs (Ipswich, MA). DNA purification kits (QIAprep spin minikit, QIAquick gel extraction kit, QIAquick PCR purification kit) were from Qiagen (Valencia, CA). Sub-cloning efficiency DH5□ competent cells and One Shot BL21(DE3) chemically competent *E. coli* were purchased from Invitrogen (Carlsbad, CA) and used to generate "in-house" high-competency cell lines. Oligonucleotides were purchased from Integrated DNA Technologies (Coralville, IA). The new intein genes were generated synthetically and purchased from GENEWIZ (South Plainfield, NJ). All plasmids used in this study were sequenced by GENEWIZ.

Criterion XT Bis-Tris gels (12%), Immun-blot PVDF membrane (0.2 µm), and Bradford reagent dye concentrate were purchased from Bio-Rad (Hercules, CA). 20×MES-SDS running buffer was purchased from Boston Bioproducts (Ashland, MA). Mouse anti-myc monoclonal antibody (α-myc) was purchased from Invitrogen (Carlsbad, CA). Anti-His Tag, clone HIS.H8 mouse monoclonal antibody (α-His6) was purchased from Millipore (Billerica, MA). Mouse HA.11 monoclonal antibody (α-HA) was purchased from Covance (Princeton, NJ). IRDye 800CW goat anti-Mouse IgG secondary antibody (Licor mouse 800) and Licor Blocking Buffer were purchased from LI-COR Biotechnology (Lincoln, NE).

Equipment

Size-exclusion chromatography was carried out on an ÄKTA FPLC system from GE Healthcare. Both preparative and analytical FPLC were carried out on a Superdex 75 10/300 or S200 10/300 column. For all runs, proteins were eluted over 1.35 column volumes of buffer (flow rate: 0.5 mL/min). Analytical RP-HPLC was performed on Hewlett-Packard 1100 and 1200 series instruments equipped with a C18 Vydac column (5 µm, 4.6×150 mm) at a flow rate of 1 mL/min. Preparative RP-HPLC was performed on a Waters prep LC system comprised of a Waters 2545 Binary Gradient Module and a Waters 2489 UV detector. Purifications were carried out on a C18 Vydac 218TP1022 column (10 µM; 22×250 mm). All runs used 0.1% TFA (trifluoroacetic acid) in water (solvent A) and 90% acetonitrile in water with 0.1% TFA (solvent B). For all runs, a two minute isocratic period in initial conditions was followed by a 30 minute linear gradient with increasing buffer B concentration. Electrospray ionization mass spectrometric analysis (ESI-MS) was performed on a Bruker Daltonics MicrOTOF-Q II mass spectrometer. In vivo intein activity assays were carried out on a VersaMax tunable microplate reader from Molecular Devices. Cells were lysed using an S-450D Branson Digital Sonifier. Western blots and coomassie-stained in vitro splicing assay gels were imaged on a LI-COR Odyssey Infrared Imager. Fluorescent fluorescein-containing gels were imaged using the GE ImageQuant LAS 4000 imager.

Compilation of the DnaE Sequence Library and Sequence Analysis

Protein sequences of the split DnaE inteins were obtained from the NEB InBasel. This list consisted of 23 entries as of May 2011. Of these entries, two were discarded from the study as they did not have a C-intein sequence: Csp (PCC7822) and Nosp(CCY9414). Two pairs of inteins had identical sequences: Nsp(PCC7120) with Asp (these are most likely the same organism with two different names) and Sel(PCC6301) with Sel(PCC7942). Thus, Nsp(PCC7120) and Sel(PCC6301) were removed from the library. The Mcht (PCC7420) and Oli C-intein sequences were identical, but both inteins were kept in the library as their N-intein sequences were different. In the InBase, the Aov intein had an "X" at position 87 in place of an absolutely conserved isoleucine (I), so 187 was utilized at this position. The plasmid for the kanamycin resistance assays bearing the Csp(PCC7424) intein proved to be unstable and yielded highly variable results; thus this intein was excluded from the analyses. The final library contained 18 inteins, Table 1.

TABLE 1

| DnaE Intein Name | Genus | Species | Strain |
|---|---|---|---|
| Npu | *Nostoc* | *punctiforme* | PCC73102 |
| Ssp | *Synechocystis* | species | PCC6803 |
| Aha | *Aphanothece* | *halophytica* | |
| Aov | *Aphanizomenon* | *ovalisporum* | |
| Asp | *Anabaena* | species | PCC7120 |
| Ava | *Anabaena* | *variabilis* | ATCC29413 |
| Cra(CS505) | *Cylindrospermopsis* | *raciborskii* | CS-505 |
| Csp(CCY0110) | *Cyanothece* | species | CCY0110 |
| Csp(PCC8801) | *Cyanothece* | species | PCC8801 |
| Cwa | *Crocosphaera* | *watsonii* | WH 8501 |
| Maer(NIES843) | *Microcystis* | *aeruginosa* | NIES-843 |
| Mcht (PCC7420)-2 | *Microcoleus* | *chthonoplastes* | PCC7420 |
| Oli | *Oscillatoria* | *limnetica* | Solar Lake |
| Sel(PC7942) | *Synechococcus* | *elongatus* | PC7942 |
| Ssp(PCC7002) | *Synechococcus* | species | PCC7002 |
| Tel | *Thermosynechococcus* | *elongatus* | BP-1 |
| Ter-3 | *Trichodesmium* | *erythraeum* | IMS101 |
| Tvu | *Thermosynechococcus* | *vulcanus* | |

Given the high homology of DnaE intein sequences, the N- and C-inteins were manually aligned using the multiple alignment software Jalview2. All N-intein sequences were "left-justified" to align the first cysteine residue, and the variable N-intein tail region was not aligned. All C-intein sequences were "right-justified" to align the C-terminal asparagine. The residue numbering used in this study is based on the numbering for the NMR structure of a fused Npu intein (PDB code 2KEQ). Thus, the variable N-intein tail region after residue 102 (the last residue of NpuN) is excluded from the numbering, as is the N-terminal methionine of the C-intein. The C-intein numbering starts at 103, except for the Tel and Tvu inteins, which have a gap at this position and start at 104. For the sequence logos (FIG. 6), the N- and C-intein alignments were each separated into two alignments based on high and low activity. The high activity sequence logos were comprised of Cwa, Cra(CS505), Csp (PCC8801), Ava, Npu, Csp(CCY0110), Mcht(PCC7420), Maer(NIES843), Asp, Oli, and Aha (which was included based on the high activity of the C120G mutant). The low activity sequence logos were comprised of Aov, Ter, Ssp (PCC7002), Tvu, Tel, Ssp, and Sel(PC7942). The sequence logos were generated using WebLogo. (4) Heat maps were generated using the statistical computing and graphics program "R".

Cloning of Plasmids for In Vivo Screening

The aminoglycoside phosphotransferase (KanR) and Npu gene fragments were cloned into a pBluescript KS (+) vector between KpnI and SacI restriction sites as previously described (36,37). This construct contained the following architecture:

[KanR promoter]-[RBS]-[myc-KanRN]-[IntN]-
    [iRBS]-[IntC]-[CFN-KanRC]

where the KanR promoter is the constitutive promoter found in most kanamycin-resistant plasmids, RBS is a common *E. coli* ribosomal binding site, iRBS is an intervening ribosomal binding site preceded by a linker, myc encodes for a c-myc epitope tag (EQKLISEEDL) (SEQ ID NO: 760), KanRN and KanRC are fragments of the KanR protein, and IntN and IntC are split intein fragments. An analogous Ssp plasmid was also constructed as previously described (36, 37). These plasmids are referred to as myc-KanR-NpuDnaE-Split and myc-KanR-SspDnaE-Split. To generate the screening vectors for the remaining split inteins, synthetic genes were designed and purchased from GENEWIZ containing the following architecture:

[5' overhang]-[IntN]-[iRBS]-[IntC]-[3' overhang]

where the 5' and 3' overhangs were the exact 39 bp found upstream of NpuN and 25 bp found downstream of NpuC, respectively, in the myc-KanR-NpuDnaE-Split plasmid. For all inteins, the purchased gene sequences were codon-optimized with the default E. coli codon usage table generated based on all E. coli coding sequences in GenBank8. The synthetic genes were received in pUC57 vectors.

To clone the screening plasmids, the entire synthetic gene was amplified with Phusion High-Fidelity Polymerase using primers annealing to the 5' and 3' overhangs. The resulting megaprimer was inserted into the myc-KanR plasmid in place of Npu by overlap-extension PCR with Phusion polymerase (39). This resulted in 18 homologous plasmids containing identical backbones, promotors, and KanR genes, but with different codon-optimized intein genes. The plasmids are named as: myc-KanR-XyzDnaE-Split (where Xyz indicates the intein name as given in Table 1). Specific point mutations were made to various inteins using a QuikChange Site-Directed Mutagenesis kit with the standard recommended protocol.

In Vivo Screening of Relative Intein Activities

96-Well Plate Assay:

Intein activity-coupled kanamycin resistance (KanR) assays were conducted in 96-well plate format as previously described (36,37). Typically, plasmids were transformed into 15 µL of sub-cloning efficiency DH5a cells by heat shock, and the transformed cells were grown for 18 hours at 37° C. in 3 mL of Luria-Bertani (LB) media with 100 µg/mL of ampicillin (LB/amp). The over-night cultures were diluted 250-fold into LB/amp solutions containing 8 different kanamycin concentrations (150 µL per culture). The cells were grown at 30° C. on a 96-well plate, monitoring optical density (OD) at 650 nm every 5 minutes for 24 hours while shaking for one minute preceding each measurement. The endpoint of this growth curve (typically in the stationary phase) was plotted as a function of kanamycin concentration to visualize the dose-response relationship and fitted to a variable-slope dose-response equation to determine $IC_{50}$ values.

$$OD_{Obs} = OD_{Min} + \frac{(OD_{Max} - OD_{Min})}{1 + 10^{[(logIC_{50} - log[Kan]) \cdot HillSlope]}}$$

In each regression analysis, typically three or four independent dose response curves were collectively fit to the equation above using the GraphPad Prism software. In each fit, $OD_{min}$ was fixed to the background absorbance at 650 nm, and all other parameters were allowed to vary. The reported error bars for the $IC_{50}$ bar graphs (FIG. 1b) represent the standard error in the best-fit $IC_{50}$ value from three or four collectively fit dose-response curves.

Western Blot Analysis of In Vivo Splicing:

For the western blot analyses, DH5a cells were transformed with the assay plasmids identically as for the 96-well plate setup and grown for 18 hours at 37° C. while shaking. The overnight cultures were used to inoculate 3 mL of fresh LB/amp at a 1:300 dilution, and the cells were incubated at 30° C. for 24 hours. The ODs of the 30° C. cultures were measured at 650 nm to assess relative bacterial levels, then 150 µL of each culture was transferred to an Eppendorf tube and centrifuged at 17,000 rcf for 2 minutes. The supernatant was aspirated off, and the cell pellets were resuspended/lysed in ~200 µL of 2×SDS gel loading dye containing 4% BME (the resuspension volumes were varied slightly to normalize for differences in OD). The samples were boiled for 10 minutes, then centrifuged at 17,000 rcf for 1 minute. Each sample (5 µL) was loaded onto a 12% Bis-Tris gel and run in MES-SDS running buffer. The proteins were transferred to PVDF membrane in Towbin transfer buffer (25 mM Tris, 192 mM glycine, 15% methanol) at 100V for 90 minutes. Membranes were blocked with 4% milk in TBST, then the primary antibody (α-myc, 1:5000) and secondary antibody (Licor mouse 800, 1:15,000) were sequentially applied in 4% milk in TBST. The blots were imaged using the Licor Odyssey scanner.

Cloning of Plasmids for In Vitro Splicing Assays

Ub-IntN Plasmids:

The N-intein expression plasmids were derived from a previously described NpuN plasmid, pMR-Ub-NpuN(WT) (36,37). This plasmid encoded for the following protein sequence:

(SEQ ID NO: 761)

MHHHHHHGGMQIFVKTLTGKTITLEVESSDTIDNVKSKIQDKEGIPPDQQ

ELIFAGKQLEDGRTLSDYNIQKESTLHLVLRLRGGGGGG<u>KFAEY</u>CLSYET

EILTVEYGLLPIGKIVEKRIECTVYSVDNNGNIYTQPVAQWHDRGEQEVF

EYCLEDGSLIRATKDHKFMTVDGQMLPIDEIFERELDLMRVDNLPN where the NpuN sequence is given in bold, the immediate native local extein residues are underlined, and these residues are preceded by $His_6$-Ub with a $Gly_4$ linker. Significant in vivo proteolysis was previously observed during expression of this construct, so this plasmid was modified using QuikChange to remove the $Gly_4$ sequence. The resulting plasmid, pMR-Ub-NpuN-ΔGly$_4$ was used as the template for all other Ub-IntN plasmids and encoded for the following protein sequence:

(SEQ ID NO: 762)

MHHHHHHGGMQIFVKTLTGKTITLEVESSDTIDNVKSKIQDKEGIPPDQQ

ELIFAGKQLEDGRTLSDYNIQKESTLHLVLRLRGG<u>KFAEY</u>CLSYETEILT

VEYGLLPIGKIVEKRIECTVYSVDNNGNIYTQPVAQWHDRGEQEVFEYCL

EDGSLIRATKDHKFMTVDGQMLPIDEIFERELDLMRVDNLPN

All other IntN plasmids were cloned using overlap-extension PCR to generate Ub-IntN fusion genes in homologous plasmids in a traceless manner (39). Specifically, N-intein genes were amplified by Phusion polymerase from the synthetic gene plasmids using primers with overhangs that anneal to the plasmid sequences surrounding NpuN in pMR-Ub-NpuN-ΔGly$_4$. The resulting megaprimer was then used to insert the new N-intein gene in place of NpuN to generate a new plasmid called pMR-Ub-IntN that was identical to the NpuN plasmid except for the N-intein gene.

IntC-SUMO Plasmids:

The C-intein plasmids were all derived from a previously described NpuC plasmid, pET-NpuC(WT)-SUMO (37). This plasmid encoded for the following protein sequence:

(SEQ ID NO: 763)
MGSSHHHHHHGENLYFQ|GIKIATRKYLGKQNVYDIGVERDHNFALKNGF

IASNCFNSGLVPRGSASMSDSEVNQEAKPEVKPEVKPETHINLKVSDGSS

EIFFKIKKTTPLRRLMEAFAKRQGKEMDSLRFLYDGIRIQADQTPEDLDM

EDNDIIEAHREQIGGYPYDVPDYA where the NpuC sequence is given in bold, and the immediate native local extein residues are underlined, followed by a linker sequence and SUMO-HA. This construct is preceded by a His$_6$-tag and a tobacco etch virus (TEV) protease recognition sequence. The TEV protease cleavage site is indicated by "|" and leaves behind a glycine residue in place of an N-terminal IntC methionine.

All other IntC plasmids were cloned using overlap-extension PCR to generate IntC-SUMO fusion genes in homologous plasmids in a traceless manner (39). Specifically, C-intein genes were amplified by Phusion polymerase from the synthetic gene plasmids using primers with overhangs that anneal to the plasmid sequences surrounding NpuC in pET-NpuC(WT)-SUMO. The resulting megaprimer was then used to insert the new C-intein gene in place of NpuC to generate a new plasmid called pET-IntC-SUMO that was identical to the NpuC plasmid except for the C-intein gene.

Purification of Proteins for In Vitro Splicing Assays

Over-Expression and Purification of Ub-IntN Constructs (Except Ub-CwaN):

E. coli BL21(DE3) cells transformed with each N-intein plasmid were grown in 1 L of LB containing 100 µg/mL of ampicillin at 37° C. until OD$_{600}$=0.6. The cells were then cooled down to 18° C., and expression was induced by addition of 0.5 mM IPTG for 16 hours at 18° C. After harvesting the cells by centrifugation (10,500 rcf, 30 min), the cell pellets were transferred to 50 mL conical tubes with 5 mL of lysis buffer (50 mM phosphate, 300 mM NaCl, 5 mM imidazole, 2 mM BME, pH 8.0) and stored at -80° C. The cell pellets were resuspended by adding an additional 15 mL of lysis buffer supplemented with Complete protease inhibitor cocktail. Cells were lysed by sonication (35% amplitude, 8×20 second pulses separated by 30 seconds on ice). The soluble fraction was recovered by centrifugation (35,000 rcf, 30 min). The soluble fraction was mixed with 2 mL of Ni-NTA resin and incubated at 4° C. for 30 minutes. After incubation, the slurry was loaded onto a fitted column. After discarding the flow-through, the column was washed with 5 column volumes (CV) of lysis buffer, 5 CV of wash buffer 1 (lysis buffer with 20 mM imidazole), and 3 CV of wash buffer 2 (lysis buffer with 50 mM imidazole). The protein was eluted with elution buffer (lysis buffer with 250 mM imidazole) in four 1.5 CV elution fractions. The wash and elution fractions were analyzed by SDS-PAGE.

After enrichment over the Ni-NTA column, the proteins were purified by gel filtration. The wash and elution fractions were all treated with 50 mM DTT for 30 minutes on ice. For well-expressing proteins, the first elution fraction was then directly injected on an S75 10/300 gel filtration column (3×1 mL injections) and eluted over 1.35 CV in freshly prepared, degassed splicing buffer (100 mM phosphates, 150 mM NaCl, 1 mM DTT, 1 mM EDTA, pH 7.2). For the more dilute, low-yielding proteins, typically the 50 mM imidazole wash fraction and the first two elution fractions were pooled and concentrated four-fold to 3 mL. Then, the concentrated protein was purified by gel filtration identically to the high-yielding constructs. FPLC fractions were analyzed by SDS-PAGE, and the purest fractions were pooled and analyzed by analytical gel filtration, analytical RP-HPLC, and mass spectrometry. The concentration of pure proteins were determined by UV A280 nm and by the Bradford assay.

Over-Expression and Purification of Ub-CwaN:

The Ub-CwaN protein did not express well in the soluble fraction, and all of the enriched protein was aggregated, as observed by gel filtration analysis. Thus, after expression, cell lysis, and fractionation, as described above, the protein was extracted from the insoluble fraction of the lysate as follows. First, the lysate pellet was resuspended in 20 mL of Triton wash buffer (lysis buffer with 0.1% Triton X-100) and incubated at room temperature for 30 minutes. The Triton wash was centrifuged at 35,000 rcf for 30 minutes, and the supernatant was discarded. Next, the pellet was resuspended in 20 mL of lysis buffer containing 6 M urea, and the mixture was incubated overnight at 4° C. The mixture was centrifuged at 35,000 rcf for 30 minutes, and then the supernatant was mixed with 2 mL of NiNTA resin. The Ni column was run identically as for the native purifications described above, except that every buffer had a background of 6 M urea. Following enrichment over a Ni-NTA column, the 50 mM imidazole wash and the first two elution fractions were pooled and diluted to 0.2 mg/mL. The diluted protein was refolded into lysis buffer (without urea) by step-wise dialysis removal of the urea at 4° C. The protein was concentrated four-fold to 3 mL and immediately purified by gel filtration as indicated for the native purifications above. The pure protein was analyzed by analytical gel filtration, analytical RP-HPLC, and mass spectrometry. Note that this construct was highly susceptible to aggregation. When re-folded at 2 mg/mL rather than 0.2 mg/mL, less than 10% of the obtained protein was monomeric, whereas more dilute refolding yielded roughly 50% monomeric protein. The obtained protein was 80% monomeric, and the monomer to aggregate ratio did not change after 24 hours of storage at 4° C. The concentration of pure protein was determined by the Bradford assay.

Over-Expression and Purification of IntC-SUMO Constructs:

E. coli BL21(DE3) cells transformed with each C-intein plasmid were grown in 1 L of LB medium containing kanamycin (50 µg/mL) at 37° C. until OD$_{600}$=0.6. Then, expression was induced by addition of 0.5 mM IPTG for 3 hours at 37° C. The cells were lysed, and the desired protein was enriched over Ni-NTA resin identically as for the natively purified Ub-IntN proteins. The AvaC-SUMO and Csp(PCC8801)C-SUMO proteins did not express well at 37° C., so the proteins were re-expressed by induction at 18° C. for 16 hours. For each protein, the 50 mM imidazole wash and the first two elution fractions were pooled and dialyzed into TEV cleavage buffer (50 mM phosphate, 300 mM NaCl, 5 mM imidazole, 0.5 mM EDTA, 0.5 mM DTT, pH 8.0) then treated with 40 µg of His-tagged TEV protease overnight at room temperature. The cleavage was confirmed by RP-HPLC/MS, after which the reaction solution was incubated with Ni-NTA resin at room temperature for 30 min. The flow-through and two 1.5 CV washes with wash buffer 1 were collected and pooled. The protein was then concentrated to 3-4 mL, injected onto the S75 10/300 gel filtration column (3×1 mL injections), and eluted over 1.35 CV in freshly prepared, degassed splicing buffer (100 mM phosphates, 150 mM NaCl, 1 mM DTT, 1 mM EDTA, pH 7.2).

FPLC fractions were analyzed by SDS-PAGE, and the purest fractions were pooled and analyzed by analytical gel filtration, analytical RP-HPLC, and mass spectrometry. The concentration of pure protein was determined by UV $A_{280nm}$ and by the Bradford assay.

Usage and Storage of the Ub-IntN and IntC-SUMO Constructs:

All of the purified proteins were stored at 4° C. and used within two days for splicing assays with their cognate IntC-SUMO. The remaining protein (2 vol. eq.) was mixed with splicing buffer containing 60% glycerol (1 vol. eq.) to yield a 20% glycerol stock that was aliquoted and flash frozen in liquid $N_2$. The protein aliquots were stored at $-80°$ C. The proteins were fully functional after thawing on ice and could be flash-frozen and re-thawed at least once without detectable loss of function.

In Vitro Splicing Assays

Kinetic Assay Procedure:

For a typical assay, individual protein stock solutions of Ub-IntN and IntC-SUMO constructs were prepared in filtered splicing buffer (100 mM phosphate, 150 mM NaCl, 1 mM DTT, 1 mM EDTA, pH 7.2) at 2× the final concentration (e.g. 2.0 µM stock solution for a 1.0 µM reaction). 1 mM TCEP was added (from a pH-neutralized 100 mM stock solution) to each protein solution, and the proteins were incubated at 30° C. or 37° C. for 5 min depending on the reaction temperature. To initiate a reaction, the N- and C-intein were mixed at equal volumes (i.e. equimolar ratios). A typical reaction volume was 300 µL and was carried out in an Eppendorf tube on a heat block. During the reaction, 20 µL aliquots of the reaction solution were removed at the desired time points and quenched in 20 µL of 2× concentrated SDS gel loading dye on ice to afford a final quenched solution with 40 mM Tris (~pH 7.0), 10% (v/v) glycerol, 1% (w/v) SDS, 0.02% (w/v) bromophenol blue, and 2% (v/v) BME. For each reaction, an artificial zero time point was taken by mixing equivalent amounts of starting materials directly into the quencher solution. Samples were boiled for 10 minutes then centrifuged at 17,000 rcf for 1 minute. Aliquots of starting materials and time points (15 µL) were loaded onto Bis-Tris gels and run in MES-SDS running buffer. The gels were Coomassie-stained then imaged using the Licor Odyssey scanner.

Note that for the reactions with a CGN C-extein sequence, no BME was used in the quencher solution. Furthermore, before boiling the samples, each sample was treated with 1 µL of 2 N HCl. After boiling and cooling the samples, they were treated with 1 µL of 2 N NaOH. This procedure prevented undesired hydrolysis or thiolysis of the branched intermediate.

Determination of Kinetic Parameters:

To determine reaction rates, each lane of a gel was analyzed using the Licor Odyssey quantification function or ImageJ. Given the close proximity of the starting material bands, these bands were typically integrated together. To normalize for loading error, the integrated intensity of each band in a lane was expressed as a fraction intensity of the total band intensity in that lane (which remained relatively constant between lanes). These normalized intensities were plotted as a function of time, and data from three independent reactions were collectively fit to first-order rate equations using the GraphPad Prism software:

For reactant depletion: $Y = S \cdot (e^{-k_{obs} \cdot t}) + Z$

For product formation: $Y = Y_{max} \cdot (1 - e^{-k_{obs} \cdot t})$

Y is the fractional intensity of a species, t is time in minutes, S is a scaling factor for reactant depletion (allowed to vary), Z indicates the fraction of reactant remaining at the reaction endpoint (allowed to vary), $Y_{max}$ is a scaling factor for product formation, and $k_{obs}$ is the observed first-order rate constant for the splicing reaction (allowed to vary). Half-lives were calculated from the best-fit value for the first-order rate constant:

$$t_{1/2} = \frac{\ln 2}{k_{obs}}$$

For reactions with no detectable side product formation, the rate of product (Ub-SUMO) and IntN formation were consistent with the rate of starting material depletion.

Western Blot Analysis of Reactions:

Western blots of the zero time point and reaction endpoint were carried out to confirm the identities of the observed bands. The quenched time points from the reactions described above were loaded onto 12% Bis-Tris gels (5 µL per sample, two identical gels) and run in MES-SDS running buffer. The resolved proteins were transferred from the gel onto PVDF membrane in CAPS transfer buffer (10 mM N-cyclohexyl-3-aminopropanesulfonic acid, 10% (v/v) methanol, pH 10.5) at 100 V for 60 minutes. Membranes were blocked with Licor Blocking Buffer, then the primary antibody (α-His$_6$, 1:3000, or α-HA, 1:25,000) was applied in Licor Blocking Buffer. The secondary antibody (Licor mouse 800, 1:15,000) was applied in 4% milk in TBST. The blots were imaged using the Licor Odyssey scanner. Blots from the 30° C. and 37° C. reactions were virtually identical.

HPLC/MS Analysis of Npu-CGN and Cra(CS505)-CGN Reactions

For the HPLC/MS analysis of Npu-CGN and Cra(CS505)-CGN, individual protein stock solutions of Ub-IntN and IntC-CGN-SUMO were prepared in filtered splicing buffer (100 mM phosphate, 150 mM NaCl, 1 mM DTT, 1 mM EDTA, pH 7.2) at 8.0 µM. 1 mM TCEP was added (from a pH-neutralized 100 mM stock solution) to each protein solution, and the proteins were incubated at 30° C. for 5 min. To initiate a reaction, the N- and C-intein were mixed at equal volumes (i.e. equimolar ratios) and incubated at 30° C. During the reaction, 90 µL aliquots of the reaction solution were removed at the desired time points and quenched in 30 µL of a quenching solution (6 M guanidine hydrochloride with 4% trifluoroacetic acid). 100 µL of each quenched time point were injected onto an analytical C18 RP-HPLC column and eluted over a 25-73% buffer B gradient in 30 minutes, preceded by a two minute isocratic phase in 25% buffer B (see Equipment section for column and running buffer specifications). At different time points, various HPLC peaks were collected and their identities were confirmed by mass spectrometry. The IntC-(Ub)SUMO species were identified by MS, verifying branched intermediate formation and depletion.

Kinetic Modeling

When comparing the Npu, Cra(CS505), and Cwa reactions in the presence of CGN, higher amounts of cleaved ubiquitin (i.e. N-extein cleavage) were obtained than splice product, despite the fact that the rate of the former was slower than the latter. This observation is inconsistent with N-extein cleavage and splice product formation only occurring from the branched intermediate, since in this scenario splicing and cleavage would be competing first-order reactions occurring from the same reactant (the branched intermediate), leading to more splice product than cleavage (the opposite of that observed). In an attempt to reconcile these observations, a series of kinetic modeling simulations were carried out. All modeling was carried out using the kinetic modeling applet from BPReid (40). The models have three basic assumptions about the splicing pathway:
1. The forward and reverse reactions in the first equilibrium are fast. In addition, the position of this equilibrium lies slightly towards the amide.
2. The second equilibrium is also fast and should have $K_{eq}$ close to 1, since both intermediates are cysteinyl thioesters.
3. For fast inteins, the rate of branched intermediate resolution ($k_5$) is on the same order—of magnitude as the rates of the first two reversible steps, whereas the cleavage rates from L ($k_6$) and B ($k_7$) are relatively slow. For slow inteins, branched intermediate resolution ($k_5$) is also slow, on the same order of magnitude as the cleavage.

With these assumptions, six scenarios were devised that assess how the relative rates of cleavage and branched intermediate resolution and the equilibrium between the linear and branched intermediates could affect the rates and extents of formation of the cleavage and spliced products. For slow inteins, such as those bearing exogenous C-extein residues, the rate of branched intermediate resolution is similar to the rate of N-extein cleavage. Under these circumstances, three factors are important:
1. The relative rates of cleavage from L versus B ($k_6$ vs. $k_7$).
2. The relative rates of branched intermediate resolution versus cleavage ($k_5$ vs. $k_6+k_7$).
3. Most importantly, the rates of exchange between the linear and branched intermediates ($k_3/k_4$).
These analyses suggest not only that cleavage should be occurring both from the linear and branched intermediate, but also that cleavage at the linear intermediate may be favored.

Protein Thiolysis and Ligation from Fused DnaE Inteins and MxeGyrA

Solid-Phase Synthesis and Purification of H-Cys-Gly-Lys (Fluorescein)-$NH_2$ (CGK-Fluorescein):

Fmoc-based solid phase peptide synthesis (SPPS) was used to produce a peptide with the sequence H-Cys-Gly-Lys(Fluorescein)-$NH_2$. The peptide was synthesized on Rink amide resin at a 0.2 mmol scale as follows: 20% piperidine in DMF was used for Fmoc deprotection using a one minute equilibration of the resin followed by a 20 minute incubation. After Fmoc deprotection, amino acids were coupled using DIC/HOBt as activating agents. First, the amino acid (1.1 mmol) was dissolved in 50:50 DCM:DMF (2 mL) and was activated with DIC (1.0 mmol) and HOBt (1.2 mmol) at 0° C. for 15 minutes. The mixture was added to the N-terminally deprotected resin and coupled for 10 minutes at room temperature.

After the cysteine was coupled, the lysine side chain was deprotected by treatment with Pd(Ph$_3$)$_4$ (0.1 eq.) and phenylsilane (25 eq.) in dry DCM for 30 minutes. The peptidyl resin was washed with DCM (2×5 mL) and DMF (2×5 mL) followed by two washes with 0.5% DIPEA in DMF (v/v) and two washes with 0.5% sodium diethyldithiocarbamate trihydrate in DMF (w/v) to remove any remaining traces of the Pd catalyst. 5(6)-Carboxyfluorescein was then coupled to the lysine side chain using the DIC/HOBt activation method overnight at room temperature. Finally, the peptide was cleaved off the resin using 94% TFA, 1% TIS, 2.5% EDT, and 2.5% H$_2$O (6.5 mL) for one hour. After cleavage, roughly half of the TFA was evaporated under a stream of nitrogen. The crude peptide was precipitated with cold ether and washed with cold ether twice. Finally, the peptide was purified by RP-HPLC on C18 prep column over a 15-80% buffer B gradient in 40 minutes. The purified peptide was analyzed by analytical RP-HPLC and ESI-MS to confirm its identity. Note that no attempt was made to separately isolate the 5-carboxyfluorescein and 6-carboxyfluorescein conjugates, thus the peptide is a mixture of these two isomers.

Cloning of Ub-Intein Fusions:

All Ub-Intein fusions were cloned into a modified pTXB1 vector from NEB containing ubiquitin in which a His$_6$-tag and stop codon were inserted between the MxeGyrA intein and the chitin binding domain. This resulted in a plasmid, pTXB1-Ub-MxeGyrA-ATEA-H$_6$ that encodes for the following protein, called called Ub-MxeGyrA-ATEA-H$_6$:

(SEQ ID NO: 764)
MQIFVKTLTGKTITLEVEPSDTIENVKAKIQDKEGIPPDQQRLIFAGKQL

EDGRTLSDYNIQKESTLHLVLRLRGGCITGDALVALPEGESVRIADIVPG

ARPNSDNAIDLKVLDRHGNPVLADRLFHSGEHPVYTVRTVEGLRVTGTAN

HPLLCLVDVAGVPTLLWKLIDEIKPGDYAVIQRSAFSVDCAGFARGKPEF

APTTYTVGVPGLVRFLEAHHRDPDAQAIADELTDGRFYYAKVASVTDAGV

QPVYSLRVDTADHAFITNGFVSHAT<u>EA</u>HHHHHH in which the intein sequence for MxeGyrA (N198A) is shown in bold, preceded by ubiquitin and followed by the endogenous local C-extein sequence (underlined) and a His$_6$-tag.

This plasmid was modified to replace the MxeGyrA intein with a fused Npu intein. First, the myc-KanR-NpuDnaE-Split plasmid was modified by QuikChange to remove the iRBS sequence separating the NpuN and NpuC genes. The resulting plasmid, myc-KanR-NpuDnaE-Fused, was then used as a template to amplify megaprimers bearing the fused Npu intein with overhangs homologous to the sequences surrounding MxeGyrA in the modified pTXB1 vector. The Npu gene with the N137A mutation was inserted in place of MxeGyrA using overlap-extension PCR with the Phusion polymerase. (39) Importantly, this construct was modified to include the native C-extein residues of Npu (CFN) instead of those for MxeGyrA (TEA). The resulting plasmid, pTXB1-Ub-NpuDnaE-ACFN-H$_6$ encoded for the following protein:

(SEQ ID NO: 765)
MQIFVKTLTGKTITLEVEPSDTIENVKAKIQDKEGIPPDQQRLIFAGKQL

EDGRTLSDYNIQKESTLHLVLRLRGGCLSYETEILTVEYGLLPIGKIVEK

RIECTVYSVDNNGNIYTQPVAQWHDRGEQEVFEYCLEDGSLIRATKDHKF

MTVDGQMLPIDEIFERELDLMRVDNLPNIKIATRKYLGKQNVYDIGVERD

HNFALKNGFIASA<u>CFN</u>HHHHHH

This fusion showed substantial in vivo hydrolysis of ubiquitin when expressed in *E. coli*. Thus, it was further modified using QuikChange mutagenesis by mutating the +1 cysteine to alanine, generating the plasmid pTXB1-Ub-NpuDnaE-AAFN-H$_6$. This plasmid encoded for the following protein (Ub-NpuDnaE-AAFN-H$_6$) that was used for in vitro thiolysis experiments:

(SEQ ID NO: 766)
MQIFVKTLTGKTITLEVEPSDTIENVKAKIQDKEGIPPDQQRLIFAGKQL

EDGRTLSDYNIQKESTLHLVLRLRGGCLSYETEILTVEYGLLPIGKIVEK

RIECTVYSVDNNGNIYTQPVAQWHDRGEQEVFEYCLEDGSLIRATKDHKF

MTVDGQMLPIDEIFERELDLMRVDNLPNIKIATRKYLGKQNVYDIGVERD

HNFALKNGFIASAAFNHHHHHH

The pTXB1-Ub-AvaDnaE-AAFN-H$_6$ and pTXB1-Ub-MchtDnaE-AAFN-H$_6$ plasmids, encoding for the following protein sequences (Ub-AvaDnaE-AAFN-H$_6$ and Ub-MchtDnaE-AAFN-H$_6$, respectively), were cloned analogously by modifying the pTXB1-Ub-NpuDnaE-AAFN-H$_6$ plasmid.

Ub-AvaDnaE-AAFN-H$_6$
(SEQ ID NO: 767)
MQIFVKTLTGKTITLEVEPSDTIENVKAKIQDKEGIPPDQQRLIFAGKQL

EDGRTLSDYNIQKESTLHLVLRLRGGCLSYDTEVLTVEYGFVPIGEIVDK

GIECSVFSIDSNGIVYTQPIAQWHHRGKQEVFEYCLEDGSIIKATKDHKF

MTQDGKMLPIDEIFEQELDLLQVKGLPEIKIASRKFLGVENVYDIGVGRD

HNFFVKNGLIASAAFNHHHHHH

Ub-MchtDnaE-AAFN-H$_6$
(SEQ ID NO: 768)
MQIFVKTLTGKTITLEVEPSDTIENVKAKIQDKEGIPPDQQRLIFAGKQL

EDGRTLSDYNIQKESTLHLVLRLRGGCLSYDTQILTVEYGAVAIGEIVEK

QIECTVYSVDENGYVYTQPIAQWHNRGEQEVFEYLLEDGATIRATKDHKF

MTDEDQMLPIDQIFEQGLELKQVEVLQFVFVKIVRRQSLGVQNVYDIGVE

KDHNFCLASGEIASAAFNHHHHHH

As a control for the removal of the +1 Cys residue in the DnaE intein constructs, the +1 Thr residue was mutated from the pTXB1-Ub-MxeGyrA-ATEA-H$_6$ plasmid by QuikChange mutagenesis to yield the plasmid pTXB1-Ub-MxeGyrA-AAEA-H$_6$, encoding for the protein Ub-MxeGyrA-AAEA-H$_6$.

(SEQ ID NO: 769)
MQIFVKTLTGKTITLEVEPSDTIENVKAKIQDKEGIPPDQQRLIFAGKQL

EDGRTLSDYNIQKESTLHLVLRLRGGCITGDALVALPEGESVRIADIVPG

ARPNSDNAIDLKVLDRHGNPVLADRLFHSGEHPVYTVRTVEGLRVTGTAN

HPLLCLVDVAGVPTLLWKLIDEIKPGDYAVIQRSAFSVDCAGFARGKPEF

APTTYTVGVPGLVRFLEAHHRDPDAQAIADELTDGRFYYAKVASVTDAGV

QPVYSLRVDTADHAFITNGFVSHAAEAHHHHHH

Cloning of Additional Fusions to Fused DnaE Inteins:

Several other proteins were fused to AvaDnaE or MchtDnaE to test the sequence dependence on thiolysis from these inteins. The proteins utilized were the N-terminal S113 domain of human Grb2 (AAs 1-55+/−an exogenous C-terminal Gly), the S112 domain of human Abl kinase (AAs 122-217), eGFP, and the catalytic domain of human PARP1 (AAs 657-1015). All plasmids were cloned using the aforementioned methods to yield plasmids encoding the following proteins:

SH3-AvaDnaE-AAFN-H$_6$
(SEQ ID NO: 770)
MEAIAKYDFKATADDELSFKRGDILKVLNEECDQNWYKAELNGKDGFIPK

NYIEMCLSYDTEVLTVEYGFVPIGEIVDKGIECSVFSIDSNGIVYTQPIA

QWHHRGKQEVFEYCLEDGSIIKATKDHKFMTQDGKMLPIDEIFEQELDLL

QVKGLPEIKIASRKFLGVENVYDIGVGRDHNFFVKNGLIASAAFNHHHHH

H

SH3-Gly-AvaDnaE-AAFN-H$_6$
(SEQ ID NO: 771)
MEAIAKYDFKATADDELSFKRGDILKVLNEECDQNWYKAELNGKDGFIPK

NYIEMGCLSYDTEVLTVEYGFVPIGEIVDKGIECSVFSIDSNGIVYTQPI

AQWHHRGKQEVFEYCLEDGSIIKATKDHKFMTQDGKMLPIDEIFEQELDL

LQVKGLPEIKIASRKFLGVENVYDIGVGRDHNFFVKNGLIASAAFNHHHH

HH

SH3-MchtDnaE-AAFN-H$_6$
(SEQ ID NO: 772)
MEAIAKYDFKATADDELSFKRGDILKVLNEECDQNWYKAELNGKDGFIPK

NYIEMCLSYDTQILTVEYGAVAIGEIVEKQIECTVYSVDENGYVYTQPIA

QWHNRGEQEVFEYLLEDGATIRATKDHKFMTDEDQMLPIDQIFEQGLELK

QVEVLQPVFVKIVRRQSLGVQNVYDIGVEKDHNFCLASGEIASAAFNHHH

HHH

SH2-AvaDnaE-AAFN-H$_6$
(SEQ ID NO: 773)
MLEKHSWYHGPVSRNAAEYLLSSGINGSFLVRESESSPGQRSISLRYEGR

VYHYRINTASDGKLYVSSESRFNTLAELVHHHSTVADGLITTLHYPACLS

YDTEVLTVEYGFVPIGEIVDKGIECSVFSIDSNGIVYTQPIAQWHHRGKQ

EVFEYCLEDGSIIKATKDHKFMTQDGKMLPIDEIFEQELDLLQVKGLPEI

KIASRKFLGVENVYDIGVGRDHNFFVKNGLIASAAFNHHHHHH eGFP-AvaDnaE-AAFN-H$_6$
(SEQ ID NO: 774)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKCLSYDTEVLTV

EYGFVPIGEIVDKGIECSVFSIDSNGIVYTQPIAQWHHRGKQEVFEYCLE

DGSIIKATKDHKFMTQDGKMLPIDEIFEQELDLLQVKGLPEIKIASRKFL

GVENVYDIGVGRDHNFFVKNGLIASAAFNHHHHHH

PARP$_C$-AvaDnaE-AAFN-H$_6$
(SEQ ID NO: 775)
MVNPGTKSKLPKPVQDLIKMIFDVESMKKAMVEYEIDLQKMPLGKLSKRQ

IQAAYSILSEVQQAVSQGSSDSQILDLSNRFYTLIPHDFGMKKPPLLNNA

DSVQAKAEMLDNLLDIEVAYSLLRGGSDDSSKDPIDVNYEKLKTDIKVVD

RDSEEAEIIRKYVKNTHATTHNAYDLEVIDIFKIEREGECQRYKPFKQLH

NRRLLWHGSRTTNFAGILSQGLRIAPPEAPVTGYMFGKGIYFADMVSKSA

NYCHTSQGDPIGLILLGEVALGNMYELKHASHISKLPKGKHSVKGLGKTT

PDPSANISLDGVDVPLGTGISSGVNDTSLLYNEYIVYDIAQVNLKYLLKL

-continued

KFNFKTSLWCLSYDTEVLTVEYGFVPIGEIVDKGIECSVFSIDSNGIVYT

QPIAQWHHRGKQEVFEYCLEDGSIIKATKDHKFMTQDGKMLPIDEIFEQE

LDLLQVKGLPEIKIASRKFLGVENVYDIGVGRDHNFFVKNGLIASA<u>AFNH</u>

HHHHH

Purification of Various Protein-Intein Fusions:

E. coli BL21(DE3) cells transformed with each Protein-Intein fusion plasmid were grown in 1 L of LB medium containing ampicillin (100 µg/mL) at 37° C. until $OD_{600}$=0.6. Then, expression was induced by addition of 0.5 mM IPTG and incubation for 3 hours at 37° C. or incubation for 16 hours at 18° C. All Ub fusions were expressed at 37° C., the eGFP fusion was expressed at 18° C., and the S113, S112, and $PARP_C$ fusions were expressed at both temperatures. After harvesting the cells by centrifugation (10,500 rcf, 30 min), the cell pellets were transferred to 50 mL conical tubes with 5 mL of lysis buffer (50 mM phosphate, 300 mM NaCl, 5 mM imidazole, No BME, pH 8.0) and stored at −80° C. The cell pellets were resuspended by adding an additional 15 mL of lysis buffer supplemented with Complete protein inhibitor cocktail. Cells were lysed by sonication (35% amplitude, 8×20 second pulses separated by 30 seconds on ice). The soluble fraction was recovered by centrifugation (35,000 rcf, 30 min). The soluble fraction was mixed with 2 mL of Ni-NTA resin and incubated at 4° C. for 30 minutes. After incubation, the slurry was loaded onto a fitted column. After discarding the flow-through, the column was washed with 5 column volumes (CV) of lysis buffer, 5 CV of wash buffer 1 (lysis buffer with 20 mM imidazole), and 3 CV of wash buffer 2 (lysis buffer with 50 mM imidazole). The protein was eluted with elution buffer (lysis buffer with 250 mM imidazole) in four 1.5 CV elution fractions. The wash and elution fractions were analyzed by SDS-PAGE with loading dye containing no thiols. The cleanest fractions were pooled and treated with 10 mM TCEP for 20 minutes on ice. Then, the solution was injected on an S75 or S200 10/300 gel filtration column (2×1 mL injections), and eluted over 1.35 CV in thiolysis buffer (100 mM phosphates, 150 mM NaCl, 1 mM EDTA, 1 mM TCEP, pH 7.2). The FPLC fractions were analyzed by SDS-PAGE with loading dye containing no thiols, and the purest fractions were pooled and analyzed by analytical RP-HPLC and mass spectrometry. The concentration of pure protein was determined by UV $A_{280nm}$.

Thiolysis of Ub-Intein Fusions and Ligation of Ubiquitin to a Small Fluorescent Peptide:

For each Ub-Intein fusion protein, four reactions were carried on a 100 µL scale at 30° C. In the first reaction to monitor background hydrolysis, the fusion protein (50 µM) was incubated in thiolysis buffer (100 mM phosphate, 150 mM NaCl, 1 mM EDTA, 1 mM TCEP, pH 7.2) supplemented with freshly added TCEP (an additional 5 mM). In the second and third reactions, the protein was incubated identically as for the first reaction, except that each reaction had either 100 mM MESNa or 1 mM CGK-Fluorescein. In the fourth reaction, both MESNa and the peptide were added. At various time points, 5 µL of reaction solution were removed and quenched in 30 µL 2×SDS loading dye containing no thiols. As time points were collected, they were stored at −20° C. until the end of the reaction. After the reaction, the 35 µL quenched time points were thawed, treated with 1 µL of a 1 M TCEP stock solution, boiled for 10 minutes, and centrifuged at 17,000 rcf for 1 minute. Time points (5 µL) were loaded onto 12% Bis-Tris gels and run in MES-SDS running buffer. The gels were first imaged on a fluorescence imager to visualize the Ub-CGK-Fluorescein ligation product. Then the gels were coomassie-stained and imaged using the Licor Odyssey scanner. In addition, the reaction endpoints were quenched by 20-fold dilution in $H_2O$ with 0.1% TFA and injected on an analytical C18 RP-HPLC column. The mixture was separated over a 2 minute isocratic phase in 0% B followed by a 0-73% B linear gradient in 30 minutes. The major peaks were collected and analyzed by MS.

Thiolysis of SH3-, SH2-, eGFP-, and $PARP_C$-Intein Fusions:

Thiolysis reactions with several other proteins fused to the AvaDnaE and MchtDnaE fused inteins were carried out analogously to the ubiquitin reactions described above. In a typical reaction, carried out on a 300 µL scale at 30° C., 10 µM fusion protein was treated with 5 mM TCEP in thiolysis buffer then incubated in the presence or absence of MESNa (either 100 mM or 200 mM) added from a pH-adjusted 1 M stock solution. At various time points, aliquots (15 µL) of the reaction solution were quenched in 30 µL of 2×SDS gel loading dye containing no thiols and stored at −20° C. until the end of the reaction. After the reaction, the 45 µL quenched time points were thawed, treated with 1 µL of a 1 M TCEP stock solution, boiled for 10 minutes, and centrifuged at 17,000 rcf for 1 minute. Time points (15 µL) were loaded onto 12% Bis-Tris gels and run in MES-SDS running buffer. Then the gels were coomassie-stained and imaged using the Licor Odyssey scanner. In addition, the reaction endpoints were quenched by 4-fold dilution in $H_2O$ with 0.1% TFA and injected on an analytical C18 RP-HPLC column. The mixture was separated over a 2 minute isocratic phase in 0% B followed by a 0-73% B linear gradient in 30 minutes. The product peaks were collected and analyzed by MS.

Observation of the Linear Thioester Intermediate in Fused DnaE Inteins

For Npu, Ava, and Mcht fusions to ubiquitin, three peaks were visible for the purified protein when directly injected onto a C18 RP-HPLC column from a neutral buffer. These peaks all had the same mass of the desired protein. When diluted 20-fold in $H_2O$ containing 0.1% TFA (pH 2) and incubated for at least two hours at room temperature, the first two peaks merged into the third peak (FIG. 4d). The same observation could not be made for MxeGyrA under identical conditions. To further confirm that an equilibrium between the precursor amide and linear thioester was occurring, the Ub-NpuDnaE-AAFN-$H_6$ protein was diluted 20-fold in thiolysis buffer containing 1% SDS. Before boiling, the two major peaks were visible. After boiling for 10 minutes, when the protein was unfolded, the first major peak partially converged into the second major peak, suggesting that the latter was the amide, which should be more stable in the unfolded intein. Additional evidence that the three peaks were in equilibrium came from pH titrations. The protein was diluted 20-fold into citric acid/phosphate buffers ranging from pH 2 to pH 8, incubated at room temperature for 3-4 hours, then analyzed by HPLC over a 30-73% B gradient in 30 minutes (FIG. 4d). The relative abundance of the three species was modulated and showed a bell-shaped pH dependence, similar to the activities of enzymes containing multiple ionizable functional groups in their active sites.

In addition to observing the desired protein mass from all three observed HPLC peaks, the presence of a −18 Da species was observed in the first two peaks. This mass change is characteristic of a dehydration reaction, and such a reaction has been previously reported by Mootz et. al. for a mutant form of the SspDnaB intein that cannot efficiently catalyze the initial N-to-S acyl shift. (41) Specifically, the tetrahedral intermediate of the forward and reverse acylation reactions can undergo acid-catalyzed dehydration to yield a thiazoline side product. For Mootz and co-workers, this species was an irreversible side-product for their mutant intein under normal reaction conditions, and it lead to low yields. In the systems herein, where the DnaE inteins can react to completion, this species is either an artifact of acidification during RP-HPLC or it is fully reversible under normal reaction conditions. It is noteworthy that the observation of the thiazoline by MS further validates the presence of detectable levels of the tetrahedral intermediate in the present reaction mixtures.

For the DnaE intein fusions to proteins other than ubiquitin, similar HPLC profiles were observed with multiple peaks at neutral pH, however the ratios of the three peaks varied depending on the sequence. Additionally, for sequences more similar to the endogenous "A-E-Y" DnaE N-extein (such as the SH3 fusions with an "I-E-M" sequence), substantial accumulation of a dehydrated product (as much as 50% by HPLC/MS) was seen, similar to that observed by Mootz et. al. for the split SspDnaB intein. (41) For these constructs, this species appears to accumulate during protein expression resulting in a mixture of "trapped" (dehydrated) and "free" (native, hydrated) fusion protein. Upon addition of MESNa at neutral pH, the "free" protein rapidly undergoes thiolysis to yield the desired product, and the "trapped" protein slowly rehydrates and is also thiolyzed to yield the same desired product. Thus, in the reaction progress curves, a "burst" phase was observed followed by a slower phase. Importantly, the accumulation of dehydrated fusion protein could be reduced by expression at lower temperatures (18° C. instead of 37° C.), and these reactions could be driven faster and closer to completion by increasing the MESNa concentration from 100 mM to 200 mM MESNa. In addition, it is noteworthy that for the SH3 thiolysis reaction, the MchtDnaE intein was substantially more efficient that the AvaDnaE intein, suggesting that different fused DnaE inteins may be preferable depending on the protein of interest.

Numerous modifications and variations in the invention as set forth in the above illustrative examples are expected to occur to those skilled in the art. Consequently only such limitations as appear in the appended claims should be placed on the invention.

REFERENCES (1) Mills, K. V.; Perler, F. B. *Protein Pept. Lett.* 2005, 12, 751-5.
(2) Vila-Perelló, M.; Muir, T. W. Cell 2010, 143, 191-200.
(3) Southworth, M.; Amaya, K.; Evans, T.; Xu, M.; Perler, F. *Biotechniques* 1999, 27, 110-120.
(4) Amitai, G.; Callahan, B. P.; Stanger, M. J.; Belfort, G.; Belfort, M. *Proc. Natl. Acad. Sci. USA* 2009, 106, 11005-10.
(5) Zettler, J.; Schütz, V.; Mootz, H. D. *FEBS Lett.* 2009, 583, 909-14.
(6) Iwai, H.; Züger, S.; Jin, J.; Tam, P.-H. *FEBS Lett.* 2006, 580, 1853-8.
(7) Perler, F. B. *Nucleic Acids Res.* 2002, 30, 383-4.
(8) Caspi, J.; Amitai, G.; Belenkiy, O.; Pietrokovski, S. *Mol. Microbiol.* 2003, 50, 1569-77.
(9) Dassa, B.; Amitai, G.; Caspi, J.; Schueler-Furman, O.; Pietrokovski, S. *Biochemistry* 2007, 46, 322-330.
(10) Chen, L.; Zhang, Y.; Li, G.; Huang, H.; Zhou, N. *Anal. Biochem.* 2010, 407, 180-7.
(11) Martin, D. D.; Xu, M. Q.; Evans, T. C. *Biochemistry* 2001, 40, 1393-402.
(12) Lockless, S. W.; Muir, T. W. *Proc. Natl. Acad. Sci. USA* 2009, 106, 10999-1004.
(13) Shah, N. H.; Vila-Perelló, M.; Muir, T. W. *Angew. Chem. Int. Ed. Engl.* 2011, 50, 6511-5.
(14) Oeemig, J. S.; Aranko, A. S.; Djupsjöbacka, J.; Heinämäki, K.; Iwaï, H. *FEBS Lett.* 2009, 583, 1451-1456.
(15) Du, Z.; Liu, Y.; Ban, D.; Lopez, M. M.; Belfort, M.; Wang, C. *J. Mol. Biol.* 2010, 400, 755-67.
(16) Appleby-Tagoe, J. H.; Thiel, I. V.; Wang, Y.; Wang, Y.; Mootz, H. D.; Liu, X.-Q. *J. Biol. Chem.* 2011, 286, 34440-7.
(17) Busche, A. E. L.; Aranko, A. S.; Talebzadeh-Farooji, M.; Bernhard, F.; Dötsch, V.; Iwai, H. *Angew. Chem. Int. Ed. Engl.* 2009, 48, 6128-31.
(18) Dhar, T.; Mootz, H. D. *Chem. Commun.* 2011, 47, 3063-5.
(19) Pellois J-P, Muir T W: *Current Opinion in Chemical Biology* 2006, 10:487-491.
(20) Cheriyan M, Perler F B: *Adv Drug Deliv Rev* 2009.
(21) Muir T W, Sondhi D, Cole P A: *Proc. Natl. Acad. Sci. U.S.A* 1998, 95:6705-6710.
(22) Dawson P E, Muir T W, Clark-Lewis I, Kent S B: *Science* 1994, 266:776-779.
(23) Evans T C J R T C, Xu M-Q: *Chem Rev* 2002, 102:4869-4884.
(24) Wu Y-W, Oesterlin L K, Tan K-T, Waldmann H, Alexandrov K, Goody R S: *Nat Chem Biol* 2010, 6:534-540.
(25) Frutos S, Goger M, Giovani B, Cowburn D, Muir T W: *Nature chemical biology* 2010, 6:527-533.
(26) Isen S K, Capili A D, Lu X, Tan D S, Lima C D: *Nature* 2010, 463:906-912.
(27) Lu W, Sun Z, Tang Y, Chen J, Tang F, Zhang J, Liu J-N: *Journal of Chromatography A* 2011, 1218:2553-2560.
(28) Zettler J, Schatz V, Mootz H D: *FEBS Letters* 2009, 583:909-914.
(29) Southworth M W, Amaya K, Evans T C, Xu M Q, Perler F B: *BioTechniques* 1999, 27:110-114, 116, 118-120.
(30) Carter P J: *Exp Cell Res* 2011, 317:1261-1269.
(31) Perler, F. B. *Nucleic Acids Res.* 2002, 30, 383-4.
(32) Waterhouse, A. M.; Procter, J. B.; Martin, D. M. A.; Clamp, M.; Barton, G. J. *Bioinformatics* 2009, 25, 1189-91.
(33) Oeemig, J. S.; Aranko, A. S.; Djupsjobacka, J.; Heinämäki, K.; Iwaï, H. *FEBS Lett.* 2009, 583, 1451-1456.
(34) Crooks, G. E.; Hon, G.; Chandonia, J.-M.; Brenner, S. E. *Genome Res.* 2004, 14, 1188-90.
(35) R Development Core Team; R Foundation for Statistical Computing: Vienna, Austria, 2011.
(36) Lockless, S. W.; Muir, T. W. *Proc. Natl. Acad. Sci. USA* 2009, 106, 10999-1004.
(37) Shah, N. H.; Vila-Perelló, M.; Muir, T. W. *Angew. Chem. Int. Ed.* 2011, 50, 6511-5.
(38) Stothard, P. *BioTechniques* 2000, 28, 1102, 1104.
(39) Bryksin, A. V.; Matsumura, I. *BioTechniques* 2010, 48, 463-5.
(40) Reid, B. P.; BPReid: Hanover, N H, 2009.
(41) Schwarzer, D.; Ludwig, C.; Thiel, I. V.; Mootz, H. D. *Biochemistry* 2012, 51, 233-42.
(42) Sun, P.; Ye, S.; Ferrandon, S.; Evans, T. C.; Xu, M.-Q.; Rao, Z. *J. Mol. Biol.* 2005, 353, 1093-105

What is claimed:

1. A fusion protein comprising a split intein N-fragment and a polypeptide, wherein the split intein N-fragment comprises the sequence of SEQ ID NO: 19, or a variant of SEQ ID NO: 19, wherein the variant comprises the sequence of SEQ ID NO: 761.

2. A complex comprising the fusion protein of claim 1 and the split intein C-fragment.

3. A split intein C-fragment comprising a sequence selected from the group consisting of SEQ ID NO: 707 and 708-711.

4. The split intein C-fragment of claim 3, wherein the split intein C-fragment comprises a sequence selected from the group consisting of SEQ ID NO: 712-727 and 728-759.

5. A method for splicing two polypeptides comprising
  (a) contacting (i) a first fusion protein comprising a split intein N-fragment and a first polypeptide, wherein the split intein N-fragment comprises the sequence of SEQ ID NO: 19, or a variant of SEQ ID NO: 19, wherein the variant comprises the sequence of SEQ ID NO: 761 and (ii) a second fusion protein comprising a second polypeptide and a split intein C-fragment comprising the sequence of SEQ ID NO: 707,
  wherein contacting is performed under conditions that permit binding of the split intein N-fragment to the split intein C-fragment to form an intein intermediate; and
  (b) reacting the intein intermediate to form a conjugate of the first polypeptide with the second polypeptide.

6. A method comprising
  (a) contacting (i) the fusion protein of claim 1, and (ii) a split intein C-fragment comprising a sequence selected from the group consisting of SEQ ID NO: 708-711,
  wherein contacting is performed under conditions that permit binding of the split intein N-fragment to the split intein C-fragment to form an intein intermediate; and
  (b) contacting the intein intermediate with a nucleophile to form a conjugate of the fusion protein and the nucleophile.

7. The method of claim 6, wherein the split intein C-fragment is bound to a support, wherein the support comprises a bead, a resin, a particle or a slide.

8. The method of claim 6, wherein the fusion protein is in a whole cell lysate.

9. The method of claim 8, further comprising washing the intein intermediate to separate the intein intermediate from components of the whole cell lysate.

10. The method of claim 6, wherein the fusion protein is from a cell supernatant and wherein the method further comprises washing the intein intermediate to separate the intein intermediate from components of the cell supernatant.

11. The method of claim 6, wherein the polypeptide has a molecular weight of 40 kDa or greater.

12. The method of claim 11, wherein the polypeptide is an antibody, or fragment thereof.

13. The method of claim 6, wherein the polypeptide is secreted from a cell.

14. The method of claim 6, further comprising isolating the conjugate.

15. The method of claim 6, wherein
  the nucleophile comprises a second polypeptide, an oligonucleotide, a nanoparticle, a drug, or a polymer, or
  the nucleophile comprises a thiol and the conjugate comprises a thioester.

16. The method of claim 15, wherein the thiol is 2-mercaptoethansulfonate, an alkyl thiol, or an aryl thiol.

17. The method of claim 15, further comprising reacting the thioester with a second nucleophile to form a second conjugate.

18. The method of claim 17, wherein the second nucleophile comprises an amine, a hydrazine, or an amino-oxy moiety.

19. The method of claim 6, further comprising recombinantly producing the fusion protein and the DnaE split intein C-fragment from a polynucleotide encoding said fusion protein and a polynucleotide encoding said DnaE split intein C-fragment.

* * * * *